United States Patent
Baati et al.

(10) Patent No.: US 11,370,772 B2
(45) Date of Patent: Jun. 28, 2022

(54) 6-SUBSTITUTED 3-FLUORO-2-PYRIDINALDOXIME, 3-FLUORO-2-PYRIDINE HYDROXAMIC ACID, AND 3-FLUORO-2-PYRIDINAMIDOXIME SCAFFOLDS

(71) Applicant: CENTRE NATIONAL DE LA RECHERCHE SCIENTIFIQUE, Paris (FR)

(72) Inventors: Rachid Baati, Strasbourg (FR); Jagadeesh Yerri, Strasbourg (FR); José Dias, Brétigny sur Orge (FR)

(73) Assignees: CENTRE NATIONAL DE LA RECHERCHE SCIENTIFIQUE, Paris (FR); UNIVERSITÉ DE STRASBOURG, Strasbourg (FR)

( * ) Notice: Subject to any disclaimer, the term of this patent is extended or adjusted under 35 U.S.C. 154(b) by 0 days.

(21) Appl. No.: 16/756,240

(22) PCT Filed: Oct. 17, 2018

(86) PCT No.: PCT/EP2018/078421
§ 371 (c)(1),
(2) Date: Apr. 15, 2020

(87) PCT Pub. No.: WO2019/076986
PCT Pub. Date: Apr. 25, 2019

(65) Prior Publication Data
US 2020/0255399 A1  Aug. 13, 2020

(30) Foreign Application Priority Data
Oct. 17, 2017  (EP) .................... 17306407

(51) Int. Cl.
*C07D 401/06* (2006.01)
*A61P 39/02* (2006.01)
*C07D 213/53* (2006.01)
*C07D 213/81* (2006.01)
*C07D 401/12* (2006.01)
*C07D 405/06* (2006.01)
*C07D 519/00* (2006.01)

(52) U.S. Cl.
CPC ............ *C07D 401/06* (2013.01); *A61P 39/02* (2018.01); *C07D 213/53* (2013.01); *C07D 213/81* (2013.01); *C07D 401/12* (2013.01); *C07D 405/06* (2013.01); *C07D 519/00* (2013.01); *C07B 2200/05* (2013.01)

(58) Field of Classification Search
CPC .. C07D 401/06; C07D 401/12; C07D 213/53; C07D 213/81; C07D 405/06; C07D 519/00; C07B 2200/05
See application file for complete search history.

(56) References Cited

U.S. PATENT DOCUMENTS

| | | |
|---|---|---|
| 5,438,033 A | 8/1995 | Drumm et al. |
| 2016/0108056 A1 | 4/2016 | Park et al. |
| 2016/0272620 A1 | 9/2016 | Baati et al. |

FOREIGN PATENT DOCUMENTS

| | | | |
|---|---|---|---|
| EP | 2873663 A1 | | 5/2015 |
| WO | 92/22203 | * | 12/1992 |
| WO | 9222203 A1 | | 12/1992 |
| WO | 2014196793 A1 | | 12/2014 |
| WO | 2017021319 A1 | | 2/2017 |

OTHER PUBLICATIONS

Kliachyna, E J Med CHem, vol. 78, 455-467, 2014. (Year: 2014).*
International Search Report and Written Opinion, dated Jan. 17, 2019, from corresponding PCT application No. PCT/EP2018/078421.
Database Registry, Chemical Abstracts Service, Columbus, Ohio, US, Mar. 6, 2016, XP002779826.
Kliachyna et al., "Design, synthesis and biological evaluation of novel tetrahydroacridine pyridine-aldoxime and -amidoxime hybrids as efficient uncharged reactivators of nerve agent-inhibited human acetylcholinesterase", European Journal of Medicinal Chemistry, vol. 78, Mar. 15, 2014,pp. 455-467, XP028847852.
Kuduk et al., "Bradykinin B'1 antagonists: Biphenyl SAR studies in the cyclopropanecarboxamide series", Bioorganic & Medicinal Chemistry Letters, Amsterdam, NL, vol. 17, No. 13, Jul. 1, 2007, pp. 3608-3612, XP022114547.
European Search Report, dated Apr. 20, 2018, from EP application No. 17306407.2.

* cited by examiner

*Primary Examiner* — D Margaret M Seaman
(74) *Attorney, Agent, or Firm* — Nixon & Vanderhye

(57) ABSTRACT

Disclosed is a compound of formula (II), as well as to a process for preparing the compounds of formula (II) by a chemoselective Sonogashira reaction. It also relates to a pharmaceutical composition including at least one compound of formula (II) and at least one pharmaceutically acceptable support. Finally, it relates to the use of such a compound as a medicine, preferably in the treatment of a nervous and/or respiratory failure due to intoxication with at least one organophosphorous nerve agent; in the treatment of neurological diseases such as Alzheimer's disease; and/or in the treatment of cancer; and/or for use as antiviral drug.

14 Claims, No Drawings

6-SUBSTITUTED 3-FLUORO-2-PYRIDINALDOXIME, 3-FLUORO-2-PYRIDINE HYDROXAMIC ACID, AND 3-FLUORO-2-PYRIDINAMIDOXIME SCAFFOLDS

The present invention relates to novel compounds having a 6-Substituted 3-Fluoro-2-Pyridinaldoxime, 3-Fluoro-2-pyridine hydroxamic acid or 3-Fluoro-2-Pyridinamidoxime scaffold. Such compounds may be useful for many therapeutic and non-therapeutic applications. The invention also relates to compositions, notably pharmaceutical compositions, comprising said compounds, and their use.

Organophosphorous nerve agents (OPNA) are extremely toxic compounds that comprise chemical warfare agents (CWA) including sarin, soman, cyclosarin, tabun, methylphosphonothioate (VX) and pesticides such as paraoxon, parathion and tetraethyl pyrophosphate (TEPP). Their acute toxicity results from the irreversible inhibition of acetylcholinesterase (AChE) through phosphylation of its catalytic serine, which results in the inability of the enzyme to hydrolyze acetylcholine (ACh). Accumulation of this neurotransmitter at cholinergic synapses occurs, leading to a permanent saturation of the muscarinic and nicotinic receptors which ultimately results in seizure and respiratory arrest. Depending on the class of OPNA and on the administrated dose, death can occur within a few minutes.

Due to the similarity between the chemical precursors of CWA and pesticides, and to the relatively simple chemistry involved in their synthesis, efforts to control the proliferation of these agents have proved of limited success. Therefore, the development of effective measures to counteract OPNA poisoning remains a challenging issue to protect and treat both civilian and military populations. The current treatment for OPNA poisoning consists in the administration of a combination of atropine (antimuscarinic agent) and diazepam (anticonvulsant drug), to limit convulsions, and of a standard pyridinium oxime (pralidoxime, trimedoxime, HI-6, obidoxime, or HLö-7) to reactivate AChE. Oximes exert their action on OPNA-inhibited AChE by attacking the phosphorous atom of the phosphylated serine, leading to the removal of the phosphonate and restoration of the enzyme's catalytic activity. Some of these known compounds have a pyridinium oxime-based structure coupled to a potential ligand for the peripheral site of the enzyme (PSL), the purpose of which is to increase the affinity of the reactivator for AChE (Mercey G. et al., Accounts of Chemical Research, 756-766, 2012, Vol. 45, No. 5).

The efficiency of reactivators may be estimated by the second-order rate constant for reactivation kr2, which is the ratio of the maximal reactivation rate constant (kr) to the apparent dissociation constant of the reactivator-inhibited AChE complex (KD).

As of today, none of the known oximes has proven equally effective against all types of OPNA-inhibited AChE.

Recently, WO2017021319 discloses bifunctional compounds comprising a specific peripheral site ligand (PSL) moiety of the amino-quinoline type which had improved affinity for poisoned hAChE (thus, a lower KD), which allowed them to be potent reactivators of human AChE inhibited with any type of organophosphorous compounds.

However, there still remains a need for chemical compounds efficient in therapeutic applications, particularly against OPNA intoxications. These compounds have to be quick and easy to synthetize, with a good yield, and at a high scale.

Surprisingly, the inventors have now discovered that specific compounds, having a 3-fluoro-pyridin scaffold substituted in the 6-position and having an oxime, hydroxamic acid or amidoxime radical in the 2-position, fulfills these needs.

Indeed, such compounds are quick and very easy to produce thanks to a Sonogashira coupling step optionally followed by a reduction step. This one- or two-step(s) process allows obtaining compounds with a high variability, and which may be used in human therapy.

Notably, these compounds may be used as antidotes against OPNA intoxications or as detoxifying agents against organophosphorus compounds, thanks to their effective and fast reactivation of hAChE without denaturing the same. They may also be used in the treatment of neurodegenerative diseases such as Alzheimer's disease. Finally, particularly the oxime compounds of the invention may be used as histone deacetylases (HDAC) inhibitors; consequently, they may be used in the treatment of cancer. They may also be used as antiviral drugs. Indeed thanks to the fluoride atom in position 3 of the pyridine ring, the compounds of the invention show an increased lipophilicity, and may pass through the hemato-encephalic barrier easily.

Thus, a first object of the present invention is a compound of formula (II):

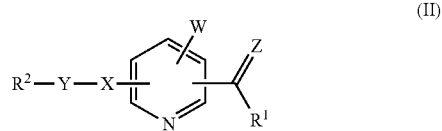

wherein the different groups are as defined in the detailed description below.

Preferably, an object of the present invention is a compound of formula (I):

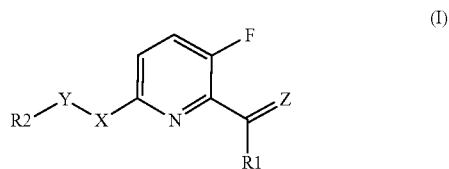

wherein the different groups are as defined in the detailed description below.

Another object of the present invention is a process for preparing the compounds of formula (II) or (I), especially by a Sonogashira reaction, as detailed below.

Another object of the present invention is a pharmaceutical composition comprising at least one compound of formula (II) or (I) and at least one pharmaceutically acceptable support.

Another object of the invention is a compound according to the invention, for use as a medicine.

A further object of the invention is a compound according to the invention for use in the treatment of a nervous and/or respiratory failure due to intoxication with at least one organophosphorous nerve agent.

Still a further object of this invention is a compound according to the invention for use in the treatment of neurological diseases such as Alzheimer's disease.

Still a further object of this invention is a compound according to the invention for use in the treatment of cancer.

Still a further object of this invention is a compound according to the invention for use as an antiviral drug.

A first object of the present invention is a compound of formula (II), or one of its pharmaceutically acceptable salts:

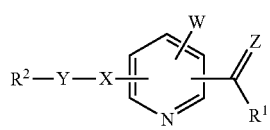

(II)

wherein:

W is F or Cl;

—X—Y— is —CH2-CH2-, —C≡C—, —CH═CH—, or —X—Y— is Br and R2 does not exist;

R1 is H, NHOH or —NH2;

Z is O or ═N—OH;

R2 is a group chosen from alkyl, haloalkyl, hydroxyalkyl, aryl, aralkyl, heteroaryl, heterocyclyl, halogen, cyano; R—O—CO—R'— wherein R and R' are both independently alkyl groups; —R3-N(R4)(R5), alkylsulfonamide, alkenyl, a biomolecule, a fluorescent probe, radical A and radical B, wherein radical A or radical B may be linked to —Y—X— by an alkyl group, preferably an ethyl group:

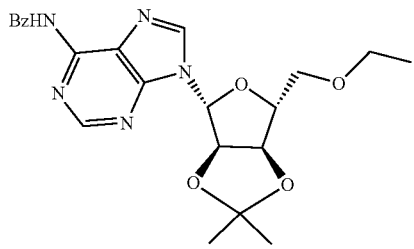

A

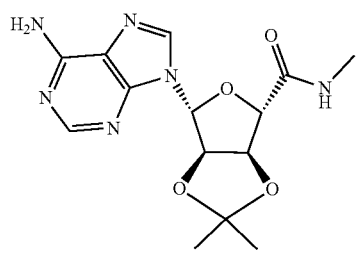

B or R2 is an alkyl group linked to the following radical:

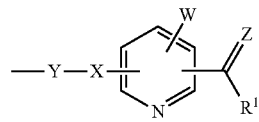

R3 is an alkyl group, and

R4 and R5 are identical or different and each independently represent H, R6-O—CO— with R6 being an alkyl group, a carboxybenzyl group, a pyridine group (preferably a 4-pyridino), a 7-chloro-2,3-dihydro-1H-cyclopenta[b]quinolin-9-yl radical, a quinolin-4-yl radical, an acridin-9-yl radical or R4 and R5 form together with the nitrogen atom a 1,3-dioxoisoindolin-2-yl, with the exception of 6-bromo-3-fluoro-2-pyridine hydroxamic acid.

By "pharmaceutically acceptable salt", it is meant any salt of a compound of formula (II) with an acid or a base. The pharmaceutically acceptable salt may be the chlorhydrate salt. For example, when R4 and/or R5 are identical or different and each independently represent a pyridine group (preferably a 4-pyridino), a quinolin-4-yl radical or an acridin-9-yl radical, said radical may be complexed with HCl, in order to give the pyridinium, the 4-quinolinium or 9-acridinium radical, respectively. Preferred pharmaceutically acceptable salts are the pyridinium, the 4-quinolinium and 9-acridinium radicals.

More specifically, the present invention relates to a compound of formula (I), or one of its pharmaceutically acceptable salts:

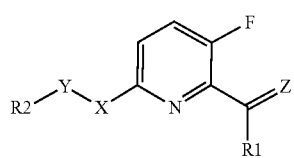

(I)

wherein:

—X—Y— is —CH2-CH2-, —C≡C—, —CH═CH—, or —X—Y— is Br and R2 does not exist;

R1 is H, NHOH or —NH2;

Z is O or ═N—OH;

R2 is a group chosen from alkyl, haloalkyl, hydroxyalkyl, aryl, aralkyl, heteroaryl, heterocyclyl, halogen, cyano; R—O—CO—R'— wherein R and R' are both independently alkyl groups; —R3-N(R4)(R5), alkylsulfonamide, alkenyl, a biomolecule, a fluorescent probe, radical A and radical B, wherein radical A or radical B may be linked to —Y—X— by an alkyl group, preferably an ethyl group:

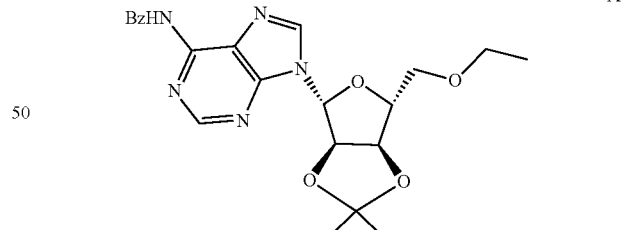

A

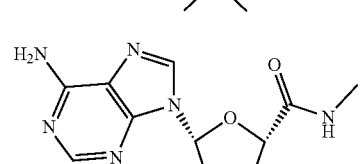

B or R2 is an alkyl group linked to the following radical:

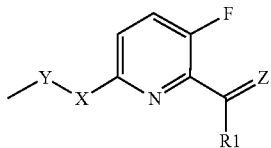

R3 is an alkyl group, and
R4 and R5 are identical or different and each independently represent H, R6-O—CO— with R6 being an alkyl group, a carboxybenzyl group, a pyridine group (preferably a 4-pyridino), a 7-chloro-2,3-dihydro-1H-cyclopenta[b]quinolin-9-yl radical, a quinolin-4-yl radical, an acridin-9-yl radical or
R4 and R5 form together with the nitrogen atom a 1,3-dioxoisoindolin-2-yl, with the exception of 6-bromo-3-fluoro-2-pyridine hydroxamic acid.

Preferably, the compound of the invention of formula (I) or (II) is different from 6-bromo-3-fluoropicolinaldehyde and from 6-bromo-3-fluoro-2-pyridinecarboxamide.

6-bromo-3-fluoropicolinaldehyde corresponds to formula (I) in which Z is O, R1 is H, and —X—Y— is Br and R2 does not exist.

6-bromo-3-fluoro-2-pyridinecarboxamide corresponds to formula (I) in which Z is O, R1 is —NH2, and —X—Y— is Br and R2 does not exist.

The compound of formula (II) or (I) may be labeled with one or more isotopes such as $^{15}N$, $^{18}O$, $^{2}H$ or $^{3}H$. Preferably the compound is labeled at Z, notably when Z is =N—OH, with $^{15}N$. Indeed, such a stable, non-toxic and non-radioactive isotope would allow in vivo and in vitro biological studies.

The carboxybenzyl group (also called Cbz) is the following group Ph-CH2-O—CO—.

By "alkyl", it is meant a linear hydrocarbon group preferably comprising from 1 to 20 carbon atoms, in particular from 1 to 15 carbon atoms, or a branched or cyclic hydrocarbon group comprising from 3 to 20 carbon atoms. Examples of alkyl groups include methyl, ethyl, n-propyl, isopropyl, n-butyl, isobutyl, tert-butyl, n-pentyl, isopentyl, n-hexyl, n-tridecyl, cyclohexyl and cyclohexylmethyl groups, and preferably ethyl, propyl, n-hexyl, n-tridecyl, cyclohexyl or cyclohexylmethyl group. The alkyl group may comprise a substitution of one hydrogen by one amino group (—NH2) or by —CO—O—C(CH3)3.

Preferably, when the alkyl group comprises said substitution, the alkyl group is 1-aminocyclohexyl or 2-methoxycarbonyl-2-tert-butoxycarbonylaminoethyle.

By "haloalkyl", it is meant an alkyl group as defined above, in which at least one hydrogen atom has been replaced by a halogen. The halogen may be F, Br, I or Cl. Examples of haloalkyl groups include 2-chloroethyl or 3-bromopropyl, and preferably 2-chloroethyl.

By "hydroxyalkyl", it is meant an alkyl group as defined above, in which at least one hydrogen atom has been substituted by a hydroxy group (OH). Preferably the hydroxyalkyl group is a C1-6 hydroxyalkyl. Examples of hydroxyalkyl groups include 4-hydroxybutyl, 5-hydroxypentyl, 6-hydroxyhexyl, and preferably 4-hydroxybutyl.

By "aryl", it is meant a monocyclic or polycyclic aromatic hydrocarbon group, which may be optionally substituted. Preferably, the aryl group is a phenyl, or a polycyclic aromatic hydrocarbon (PAH). A preferred PAH is pyrene. The aryl may be substituted by at least one alkyl group and/or by at least a cyano group (—CN). Examples of aryl groups include 4-ethylphenyl, 4-cyanophenyl or pyrenyl.

By "aralkyl", it is meant an aryl group as described above, linked to the compound of formula (I) by an alkyl group. Preferably, the aralkyl group is a phenylpropyl. The aralkyl may be substituted on the aryl group by at least one alkyl group and/or by at least a cyano group (—CN). Preferably the aralkyl is phenylpropyl.

By "heteroaryl", it is meant an aryl group in which at least one carbon atom of the aromatic ring is substituted by a heteroatom, and which may be optionally substituted. The heteroatom may be nitrogen, oxygen, phosphorus or sulfur. Preferably the heteroatom is nitrogen. Examples of heteroaryl groups include pyrrole, thiophene, furane, pyridine, pyrimidine, pyrazine, triazine, imidazole, thiazole, oxazole, and isoxazole groups. Preferably, the heteroaryl group is a pyridine group such as 4- or 3-pyridino. The heteroaryl may be substituted by at least one alkyl group and/or by at least a cyano group (—CN). Preferably, the heteroaryl group is in salt form, preferably a pyridinium group such as 4- or 3-pyridininium.

A "heterocyclyl" is refers to a monocyclic or polycyclic saturated hydrocarbon group in which at least one carbon atom of the ring is substituted by a heteroatom, and which may be optionally substituted. The heterocyclyl may be linked to the radical —Y—X— of formula (I) or (II) by an alkyl group, preferably an ethyl group. The heteroatom may be nitrogen, oxygen, or sulfur. Preferably, the heterocyclic group is morpholino, tetrahydropyrane, oxetane or azetidine, such as 4-tetrahydropyrano or 3-oxetano or 3-azetidino. The heterocyclyl may be substituted by at least one alkyl group and/or by at least a hydroxyl and/or by at least a carboxybenzyl group (i.e. Ph-CH2-O—CO—). Preferably the heterocyclyl is morpholino-N-ethyl, 4-hydroxy-4-tetrahydropyrano, 3-hydroxy-3-oxetano or 1-carboxybenzyl-3-azetidino.

By "alkylsulfonamide", it is meant a radical —R'''—SO2-NH2, in which R''' is an alkyl radical as described above, preferably an ethyl group.

By "alkenyl", it is meant a linear hydrocarbon group from 1 to 20 carbon atoms comprising at least one insaturation. Example of alkenyl group includes 2-vinylethyl.

By "biomolecule", it is meant a sugar moiety, a peptide moiety, a protein moiety, or a nucleic acid moiety such as a DNA or RNA moiety. The sugar moiety may be for example a glucose, fructose or sucrose moiety. A peptide moiety is a moiety typically comprising 1 to 50 amino acids. A protein moiety is a moiety typically comprising at least 51 amino acids, preferably from 60 to 500 amino acids.

By "fluorescent probe" it is meant a chemical function or a fluorophore endowed with fluorescent properties. The fluorescent moiety may be for example a fluoresceine, boron dipyrromethene (BODIPY), a coumarine, a cyanine, an anthracene or rhodamine moiety.

According to a first embodiment, it is preferred in formula (II) or (I) that —X—Y— is Br and R2 does not exist.

Thus, the compounds of formula (II) or (I) have scaffold 1 below:

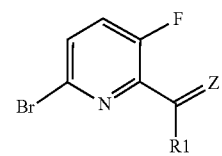

Scaffold 1 wherein R1 and Z are as defined above, with the exception of 6-bromo-3-fluoro-2-pyridine hydroxamic acid. Preferably, 6-bromo-3-fluoropicolinaldehyde and from 6-bromo-3-fluoro-2-pyridinecarboxamide are further excluded from scaffold 1.

According to a second embodiment, it is preferred in formula (II) or (I) that —X—Y— is —CH2-CH2-, —C≡C— or —CH═CH. Preferably, —X—Y— is —C≡C— (scaffold 2).

It may then be hydrogenated, so that —X—Y— is —CH═CH (scaffold 3) or —CH2-CH2- (scaffold 4).

Preferably, R1 is H and Z is ═N—OH. In such a case, the compounds of formula (I) are 6-substituted 3-fluoro-2-pyridinaldoximes.

Preferably, R1 is —NHOH and Z is O. In such a case, the compounds of formula (I) are 6-substituted 3-fluoro-2-pyridinhydroxamic acid, with the exception of 6-bromo-3-fluoro-2-pyridine hydroxamic acid.

Preferably, R1 is —NH2 and Z is ═N—OH. In such a case, the compounds of formula (I) are 6-substituted 3-fluoro-2-pyridinamidoximes.

Preferably, the compound of formula (II) is a compound of formula (I) or one of its pharmaceutically acceptable salts, and is such that: —X—Y— is —CH2-CH2-, —C≡C— or —CH═CH;
R1 is H;
Z is ═N—OH;
R2 is a group chosen from alkyl, haloalkyl, hydroxyalkyl, aryl, aralkyl, heteroaryl, heterocyclyl, halogen, cyano; R—O—CO—R'— wherein R and R' are both independently alkyl groups; —R3-N(R4)(R5), alkylsulfonamide, alkenyl, radical A and radical B, wherein radical A or radical B may be linked to —Y—X— by an alkyl group, preferably an ethyl group:

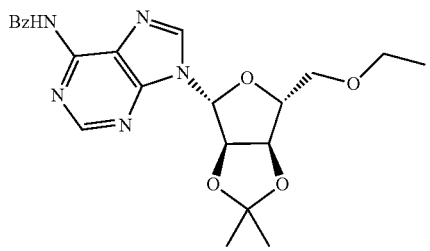

A

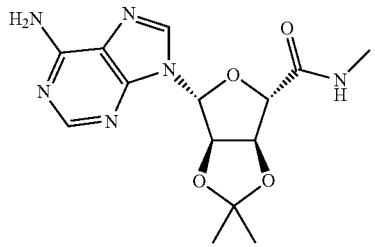

B or R2 is an alkyl group linked to the following radical:

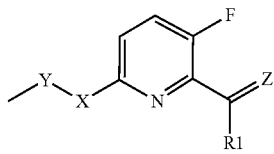

R3 is an alkyl group, and
R4 and R5 are identical or different and each independently represent H, R6-O—CO— with R6 being an alkyl group, a carboxybenzyl group, a pyridine group (preferably a 4-pyridino), a 7-chloro-2,3-dihydro-1H-cyclopenta[b]quinolin-9-yl radical, a quinolin-4-yl radical, an acridin-9-yl radical or
R4 and R5 form together with the nitrogen atom a 1,3-dioxoisoindolin-2-yl.

Preferred pharmaceutically acceptable salts are the ones for which R2 is a heteroaryl optionally in salt form such as a 3- or 4-pyridine or 3- or 4-pyridinium; or —R3-N(R4)(R5), with R5 being a pyridinium, a 4-quinolinium or a 9-acridinium radical.

Preferably, the compound of formula (II) or (I) is such that:
—X—Y— is —CH2-CH2-, —C≡C— or —CH═CH;
R1 is —NHOH;
Z is O;
R2 is a group chosen from alkyl, haloalkyl, hydroxyalkyl, aryl or aralkyl.

Preferably, the compound of formula (II) or (I) is such that:
—X—Y— is —CH2-CH2-, —C≡C— or —CH═CH;
R1 is —NH2;
Z is ═N—OH;
R2 is a group chosen from alkyl, haloalkyl, hydroxyalkyl, aryl or aralkyl.

Preferably, the compound of formula (II) is such that:
W is F or Cl;
—X—Y— is —C≡C or —X—Y— is Br and R2 does not exist;
R1 is H;
Z is ═N—OH;
R2 is a group chosen from aralkyl, preferably phenylpropyl.

Preferably, the compound of formula (II) is such that:
W is 2-fluoro;
the group —C(Z)—R1 is in position 3 and R1 is H, Z is ═N—OH; and
—X—Y— is Br and R2 does not exist, in position 5; or
—X—Y— is in position 5 and is —C≡C and R2 is a group chosen from aralkyl, preferably phenylpropyl.

Preferably, the compound of formula (II) is such that:
W is 3-fluoro;
the group —C(Z)—R1 is in position 2 and R1 is H, Z is ═N—OH; and
—X—Y— is Br and R2 does not exist, in position 5; or
—X—Y— is in position 5 and is —C≡C and R2 is a group chosen from aralkyl, preferably phenylpropyl.

Preferably, the compound of formula (II) is such that:
W is 6-chloro;
the group —C(Z)—R1 is in position 2 and R1 is H, Z is ═N—OH; and
—X—Y— is Br and R2 does not exist, in position 3; or
—X—Y— is in position 3 and is —C≡C and R2 is a group chosen from aralkyl, preferably phenylpropyl.

Preferably, the compound of formula (II) is such that:
W is 4-chloro;
the group —C(Z)—R1 is in position 3 and R1 is H, Z is ═N—OH; and
—X—Y— is Br and R2 does not exist, in position 6; or
—X—Y— is in position 6 and is —C≡C and R2 is a group chosen from aralkyl, preferably phenylpropyl.

Preferably, the compound of formula (II) is chosen among the following:

(Z)-6-bromo-3-fluoropicolinaldehyde oxime 2:

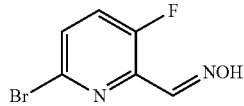

3-fluoro-6-(5-phenylpent-1-yn-1-yl)picolinaldehyde oxime 3a:

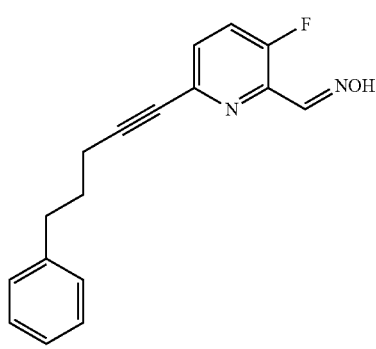

3-fluoro-6-(pentadec-1-yn-1-yl)picolinaldehyde oxime 3b:

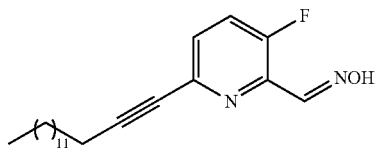

6-(3-cyclohexylprop-1-yn-1-yl)-3-fluoropicolinaldehyde oxime 3c:

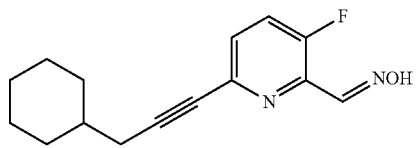

3-fluoro-6-(6-hydroxyhex-1-yn-1-yl)picolinaldehyde oxime 3d:

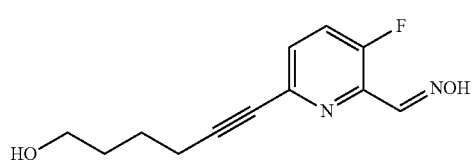

Methyl 6-(5-fluoro-6-((hydroxyimino)methyl)pyridin-2-yl)hex-5-ynoate 3e:

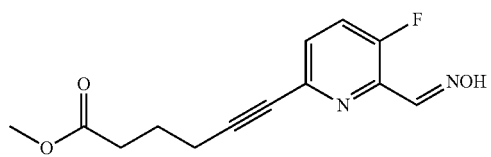

6-((1-aminocyclohexyl)ethynyl)-3-fluoropicolinaldehyde oxime 3f:

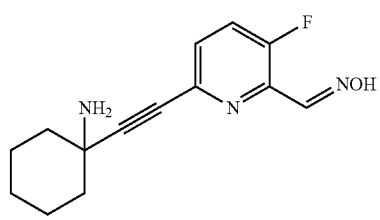

3-fluoro-6-(hex-5-en-1-yn-1-yl)picolinaldehyde oxime 3g:

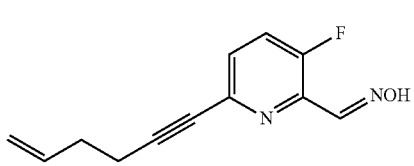

6-((4-ethylphenyl)ethynyl)-3-fluoropicolinaldehyde oxime 3h:

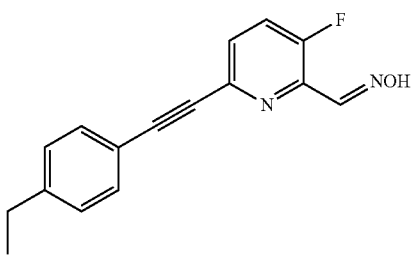

6-(4-chlorobut-1-yn-1-yl)-3-fluoropicolinaldehyde oxime 3i:

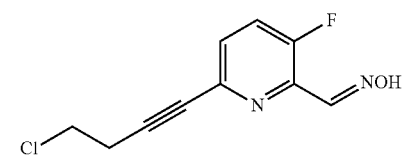

6-((3,6-dihydropyren-4-yl)ethynyl)-3-fluoropicolinaldehyde oxime 3j:

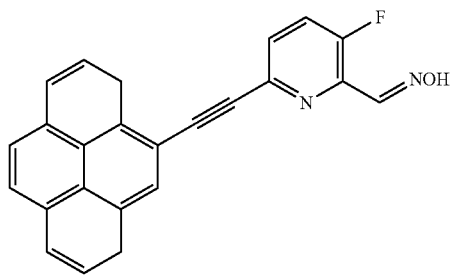

4-(5-fluoro-6-((hydroxyimino)methyl)pyridin-2-yl)but-3-yne-1-sulfonamide 3k:

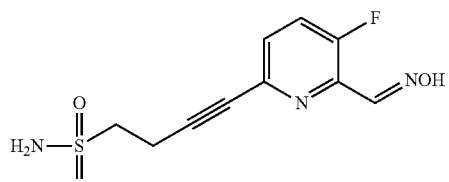

tert-butyl (4-(5-fluoro-6-((hydroxyimino)methyl)pyridin-2-yl)but-3-yn-1-yl)carbamate 3l:

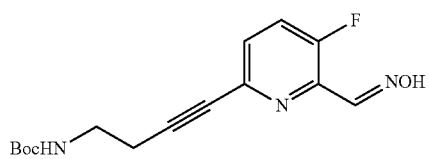

4-((5-fluoro-6-((hydroxyimino)methyl)pyridin-2-yl)ethynyl)benzonitrile 3m:

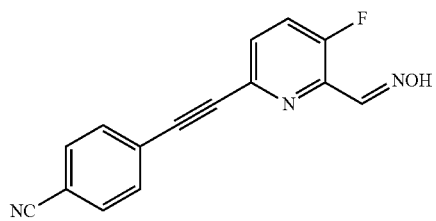

6-(5-(1,3-dioxoisoindolin-2-yl)pent-1-yn-1-yl)-3-fluoropicolinaldehyde oxime 3n:

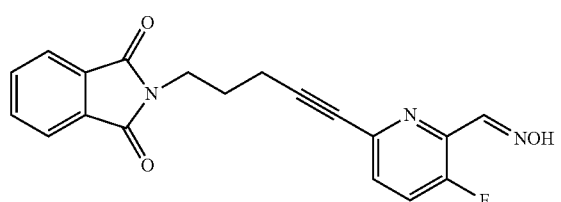

3-fluoro-6-((4-hydroxytetrahydro-2H-pyran-4-yl)ethynyl)picolinaldehyde oxime 3o:

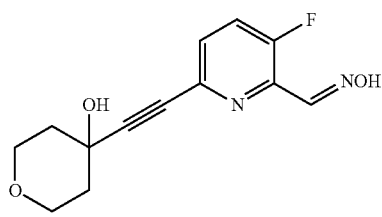

3-fluoro-6-((3-hydroxyoxetan-3-yl)ethynyl)picolinaldehyde oxime 3p:

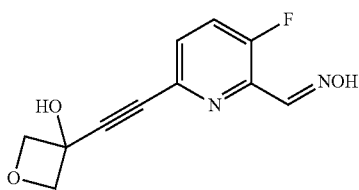

Benzyl 3-((5-fluoro-6-((hydroxyimino)methyl)pyridin-2-yl)ethynyl)azetidine-1-carboxylate 3q:

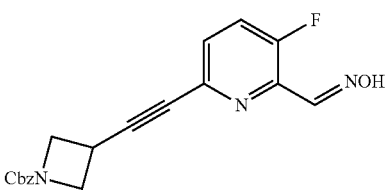

3-fluoro-6-(pyridin-3-ylethynyl)picolinaldehyde oxime 3r:

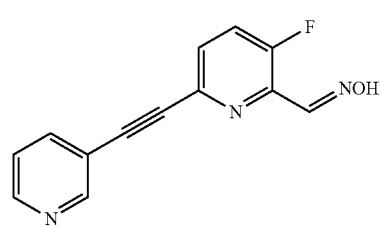

Benzyl (3-(5-fluoro-6-((hydroxyimino)methyl)pyridin-2-yl)prop-2-yn-1-yl)(pyridin-4-yl)carbamate 3s:

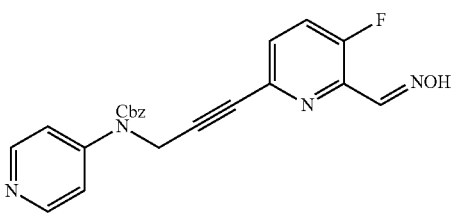

Methyl (S)-2-((tert-butoxycarbonyl)amino)-5-(5-fluoro-6-((hydroxyimino)methyl)pyri-din-2-yl)pent-4-ynoate 3t:

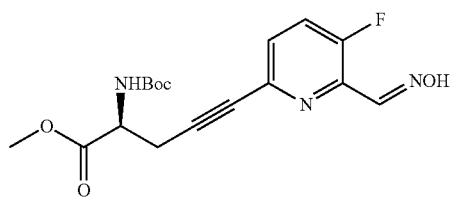

N-(9-((3aR,4R,6R,6aR)-6-(((3-(5-fluoro-6-((hydroxyimino)methyl)pyridin-2-ylprop-2-yn-1-yl)oxy)methyl)-2,2-dimethyltetrahydrofuro[3,4-d][1,3]dioxol-4-yl)-9H-purin-6-yl)benzamide 3u:

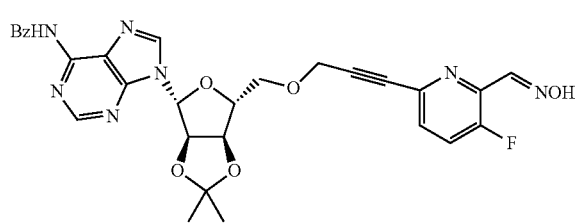

(3aS,4S,6R,6aR)-6-(6-amino-9H-purin-9-yl-N-(4-(5-fluoro-6-((Z)-(hydroxyimino)me-thyl)pyridin-2-yl)but-3-yn-1-yl)-2,2-dimethyltetrahydrofuro[3,4-d][1,3]dioxole-4-carboxamide 3v:

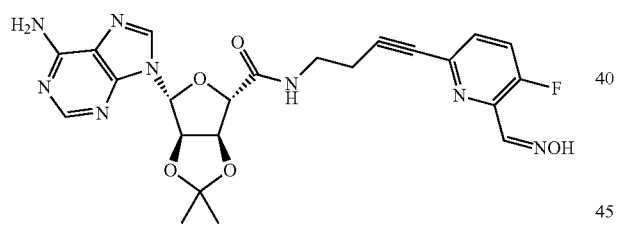

3-fluoro-6-(10-(5-fluoro-6-((E)-(hydroxyimino)methyl)pyridin-2-yl)deca-1,9-diyn-1-yl)picolinaldehyde oxime 3w:

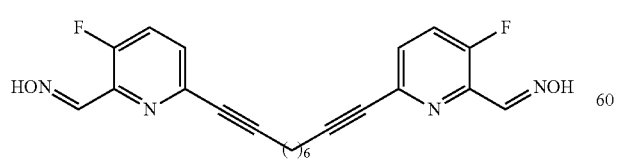

6-(4-((7-chloro-2,3-dihydro-1H-cyclopenta[b]quinolin-9-yl)amino)but-1-yn-1-yl)-3-fluoropicolinaldehyde oxime 3λ:

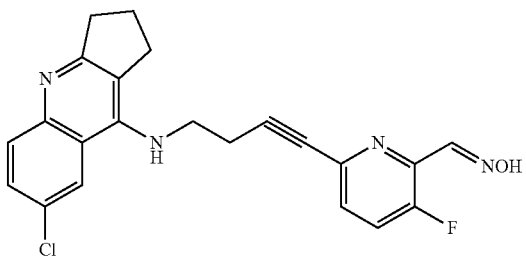

3-fluoro-6-(4-(quinolin-4-ylamino)but-1-yn-1-yl)picolinaldehyde oxime 3y:

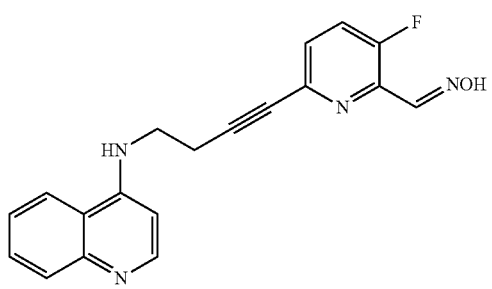

6-(4-(1,2,3,4-tetrahydroacridin-9-ylamino)but-1-yn-1-yl)-3-fluoropicolinaldehyde oxime 3z:

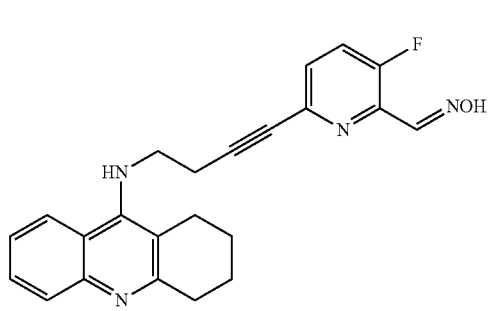

6-bromo-3-fluoropicolinaldehyde oxime (Labelled) 4:

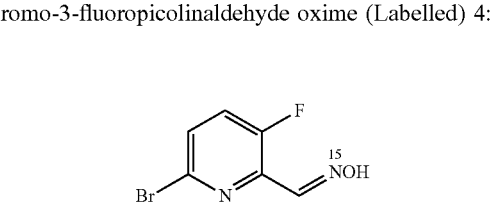

3-fluoro-6-(5-phenylpent-1-yn-1-yl)picolinaldehyde oxime 5 (labelled):

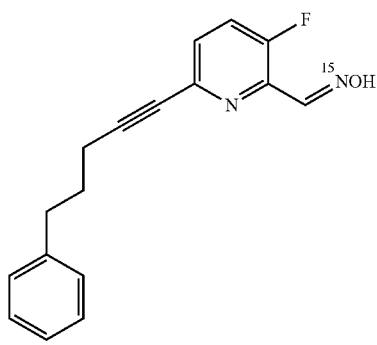

6-bromo-3-fluoro-N'-hydroxypicolinimidamide 7:

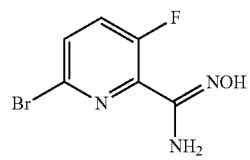

6-bromo-3-fluoro-N'-hydroxypicolinimidamide (Labelled) 8:

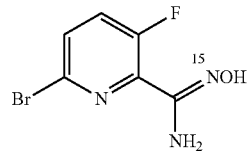

3-fluoro-6-(5-phenylpent-1-yn-1-yl)picolinonitrile 9:

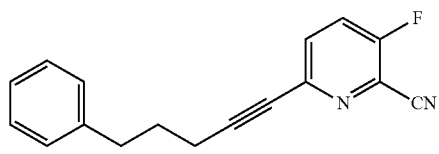

3-fluoro-N'-hydroxy-6-(5-phenylpent-1-yn-1-yl)picolinimidamide 10:

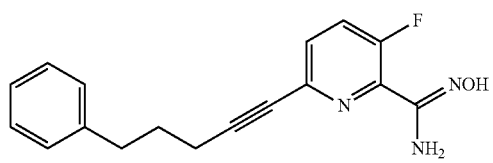

3-fluoro-N-hydroxy-6-(5-phenylpent-1-yn-1-yl)picolinamide 12:

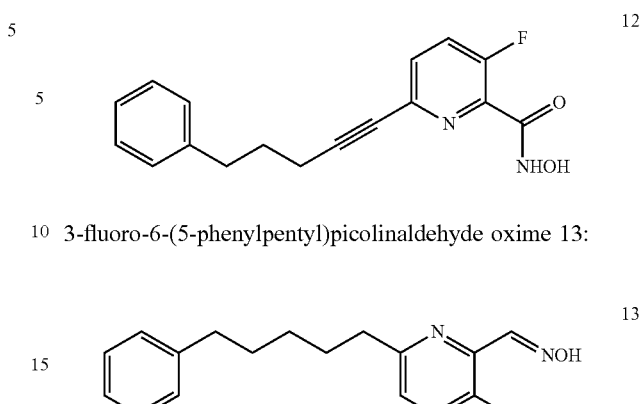

3-fluoro-6-(5-phenylpentyl)picolinaldehyde oxime 13:

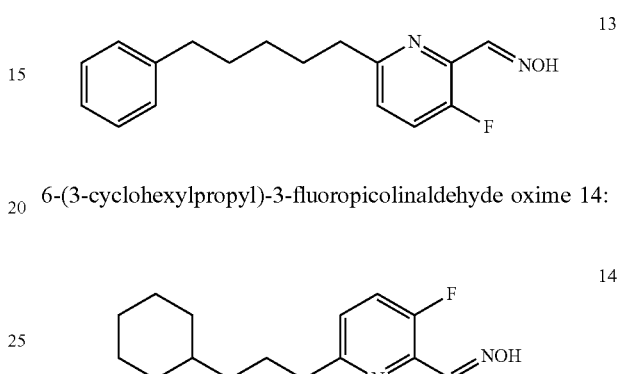

6-(3-cyclohexylpropyl)-3-fluoropicolinaldehyde oxime 14:

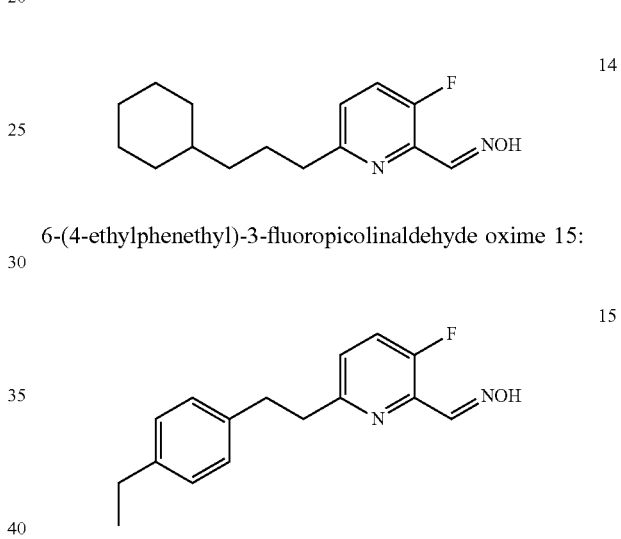

6-(4-ethylphenethyl)-3-fluoropicolinaldehyde oxime 15:

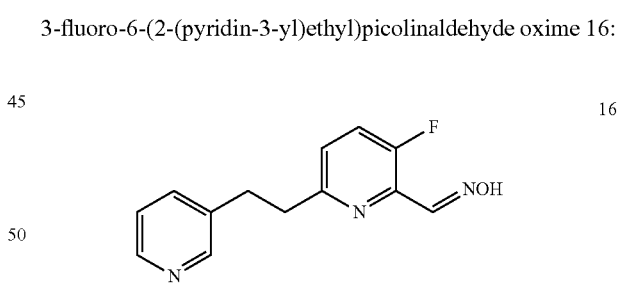

3-fluoro-6-(2-(pyridin-3-yl)ethyl)picolinaldehyde oxime 16:

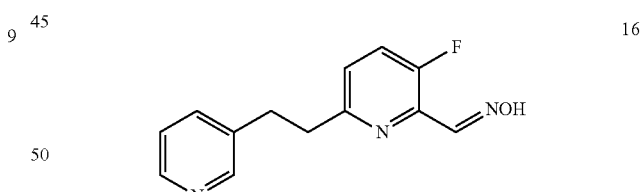

3-fluoro-6-(2-(3-hydroxyoxetan-3-yl)ethyl)picolinaldehyde oxime 17:

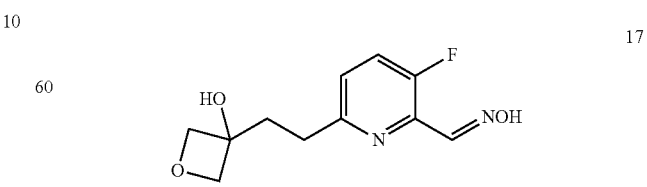

3-fluoro-6-(2-(4-hydroxytetrahydro-2H-pyran-4-yl)ethyl)picolinaldehyde oxime 18:

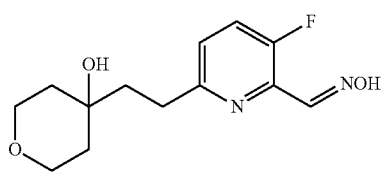

3-fluoro-6-(10-(5-fluoro-6-((hydroxyimino)methyl)pyridin-2-yl)decyl)picolin-aldehyde oxime 19:

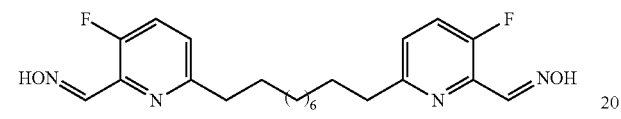

N-(9-((3aR,4R,6R,6aR)-6-((3-(5-fluoro-6-((hydroxyimino)methyl)pyridin-2-yl)propoxy)methyl)-2,2-dimethyltetrahydrofuro[3,4-d][1,3]dioxol-4-yl)-9H-purin-6-yl)benzamide 20:

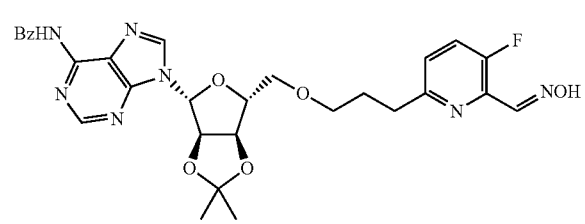

3-fluoro-6-((E)-6-hydroxyhex-1-en-1-yl)picolinaldehyde oxime 21:

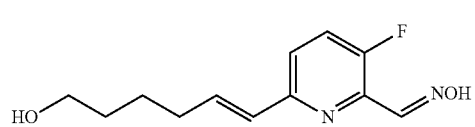

Methyl (E)-6-(5-fluoro-6-((hydroxyimino)methyl)pyridin-2-yl)hex-5-enoate 22:

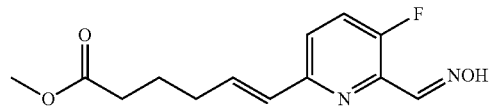

3-fluoro-6-((E)-2-(pyren-4-yl)vinyl)picolinaldehyde oxime 23:

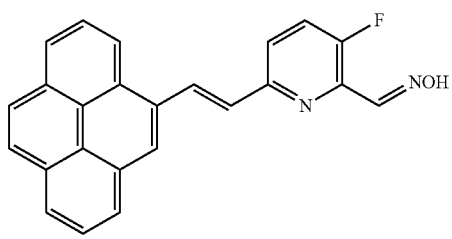

3-fluoro-6-(4-((1,2,3,4-tetrahydroacridin-9-yl)amino)butyl) picolinaldehyde oxime 24:

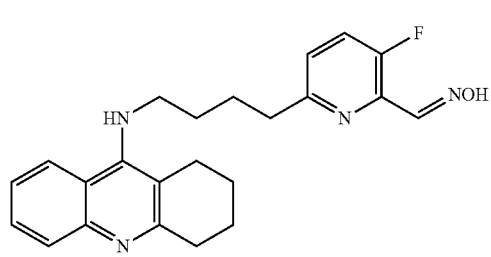

9-((4-(5-fluoro-6-((hydroxyimino)methyl)pyridin-2-yl) butyl)amino)-1,2,3,4-tetrahydroacridin-10-ium chloride 25:

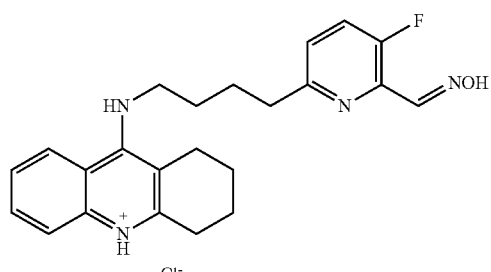

3-fluoro-6-(4-(quinolin-4-ylamino)but-1-yn-1-yl)picolinaldehyde oxime 26:

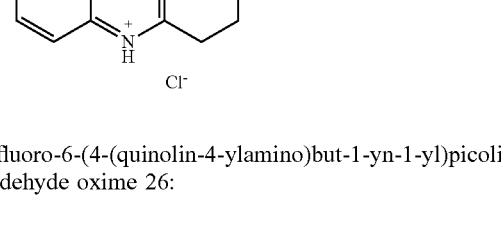

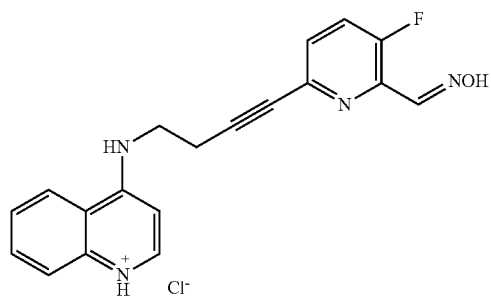

3-fluoro-6-(4-(quinolin-4-ylamino)butyl)picolinaldehyde oxime 27:

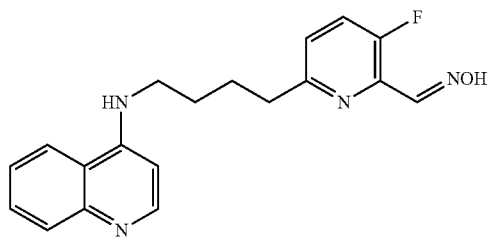

4-((4-(5-fluoro-6-((hydroxyimino)methyl)pyridin-2-yl)butyl)ammonio)quinolin-1-ium chloride 28:

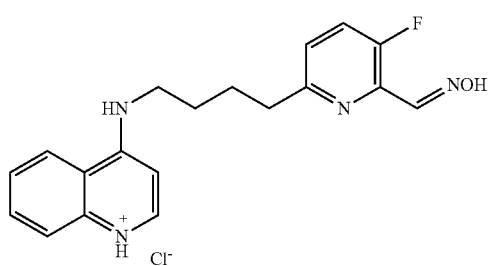

3-((5-fluoro-6-((hydroxyimino)methyl)pyridin-2-yl)ethynyl)pyridin-1-ium chloride 29:

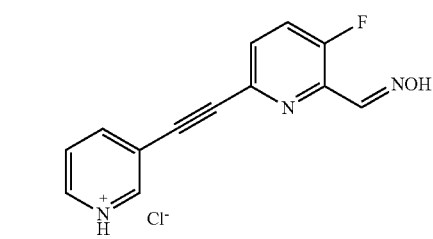

3-(2-(5-fluoro-6-((hydroxyimino)methyl)pyridin-2-yl)ethyl)pyridin-1-ium-chloride 30:

5-bromo-3-fluoropicolinaldehyde oxime 31:

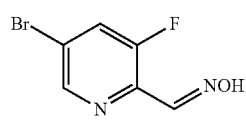

3-fluoro-5-(5-phenylpent-1-yn-1-yl)picolinaldehyde oxime 32:

5-bromo-2-fluoronicotinaldehyde oxime 33:

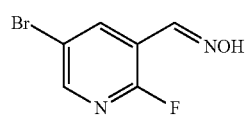

2-fluoro-5-(5-phenylpent-1-yn-1-yl)nicotinaldehyde oxime 34:

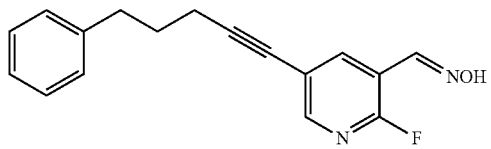

3-bromo-6-chloropicolinaldehyde oxime 35:

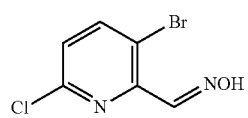

6-chloro-3-(5-phenylpent-1-yn-1-yl)picolinaldehyde oxime 36:

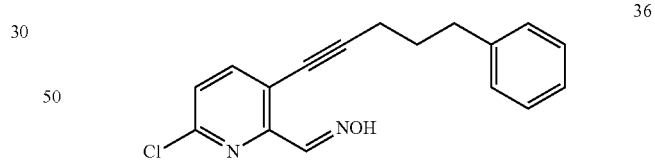

6-bromo-4-chloronicotinaldehyde oxime 37:

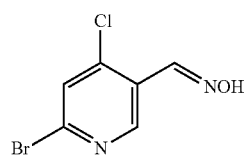

4-chloro-6-(5-phenylpent-1-yn-1-yl)nicotinaldehyde oxime 38:

3-fluoro-N'-hydroxy-6-(pentadec-1-yn-1-yl)picolinimidamide 46:

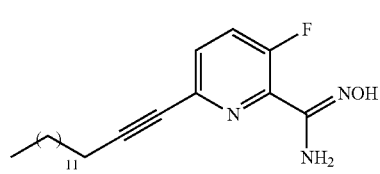

6-((4-ethylphenyl)ethynyl)-3-fluoro-N'-hydroxypicolinimidamide 47:

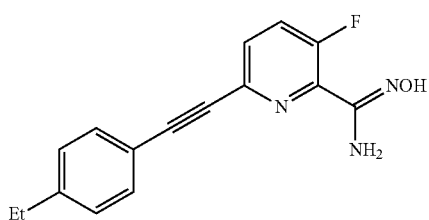

3-fluoro-N'-hydroxy-6-(4-morpholinobut-1-yn-1-yl)picolinimidamide 48:

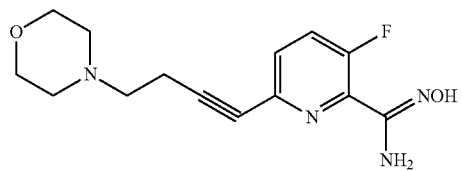

3-fluoro-N'-hydroxy-6-((3-hydroxyoxetan-3-yl)ethynyl)picolinimidamide 49:

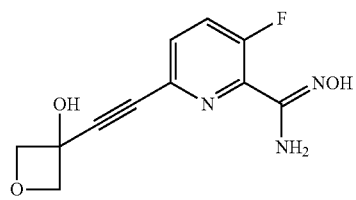

6-((1-aminocyclohexyl)ethynyl)-3-fluoro-N'-hydroxypicolinimidamide 50:

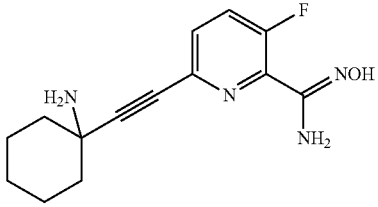

(3aS,4S,6R,6aR)-6-(6-amino-9H-purin-9-yl)-N-(4-(5-fluoro-6-((E)-N'-hydroxycarbamimidoyl)pyridin-2-yl)but-3-yn-1-yl)-2,2-dimethyltetrahydrofuro[3,4-d][1,3]dioxole-4-carboxamide 51:

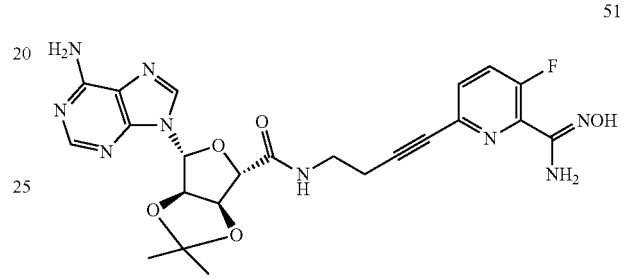

Preferably, the compound of formula (II) is a compound of formula (I).

Preferably, the compound of formula (II) or (I) is chosen among the following:

(Z)-6-bromo-3-fluoropicolinaldehyde oxime 2:

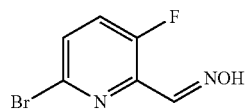

3-fluoro-6-(5-phenylpent-1-yn-1-yl)picolinaldehyde oxime 3a:

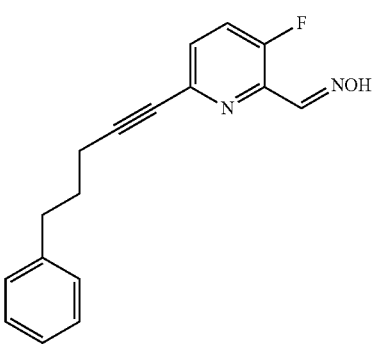

3-fluoro-6-(pentadec-1-yn-1-yl)picolinaldehyde oxime 3b:

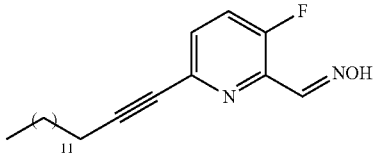

6-(3-cyclohexylprop-1-yn-1-yn)-3-fluoropicolinaldehyde oxime 3c:

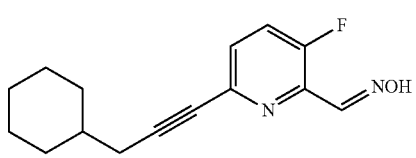

3-fluoro-6-(6-hydroxyhex-1-yn-1-yl)picolinaldehyde oxime 3d:

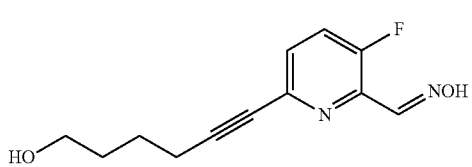

Methyl 6-(5-fluoro-6-((hydroxyimino)methyl)pyridin-2-yl)hex-5-ynoate 3e:

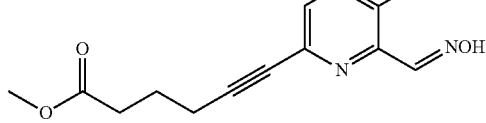

6-((1-aminocyclohexyl)ethynyl)-3-fluoropicolinaldehyde oxime 3f:

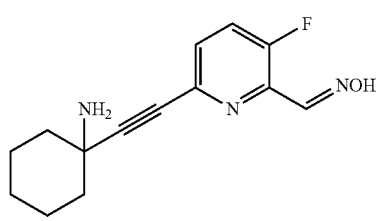

3-fluoro-6-(hex-5-en-1-yn-1-yl)picolinaldehyde oxime 3g:

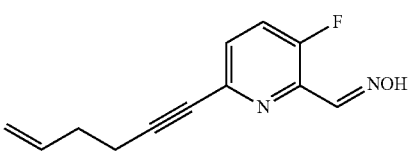

6-((4-ethylphenyl)ethynyl)-3-fluoropicolinaldehyde oxime 3h:

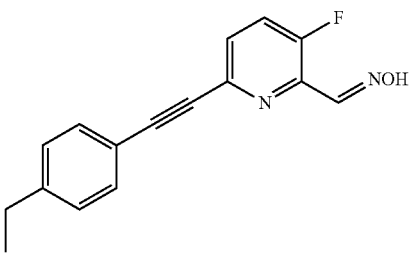

6-((4-chlorobut-1-yn-1-yl)-3-fluoropicolinaldehyde oxime 3i:

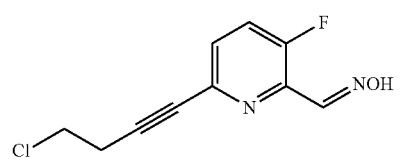

6-((3,6-dihydropyren-4-yl)ethynyl)-3-fluoropicolinaldehyde oxime 3j:

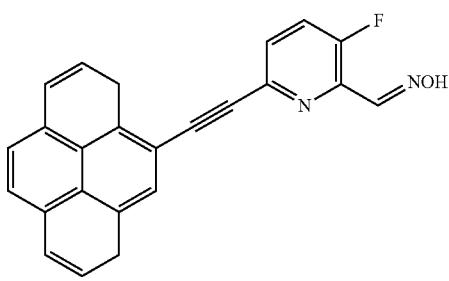

4-(5-fluoro-6-((hydroxyimino)methyl)pyridin-2-yl)but-3-yne-1-sulfonamide 3k:

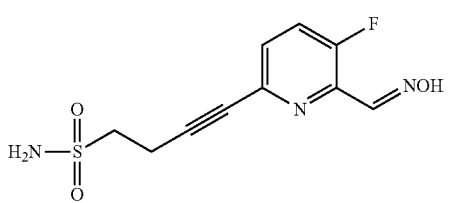

tert-butyl (4-(5-fluoro-6-((hydroxyimino)methyl)pyridin-2-yl)but-3-yn-1-yl)carbamate 3l:

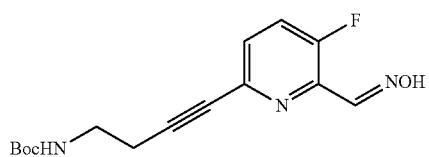

4-((5-fluoro-6-((hydroxyimino)methyl)pyridin-2-yl)ethynyl)benzonitrile 3m:

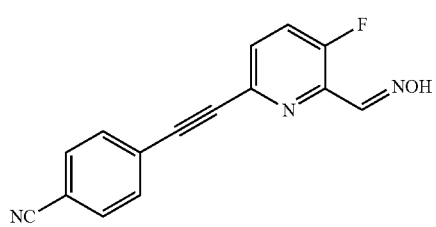

6-(5-(1,3-dioxoisoindolin-2-yl)pent-1-yn-1-yl)-3-fluoropicolinaldehyde oxime 3n:

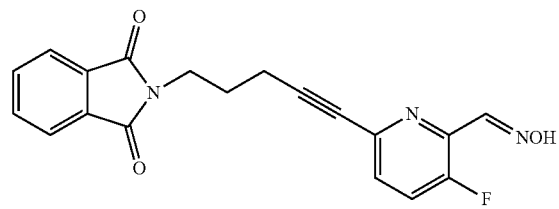

3-fluoro-6-((4-hydroxytetrahydro-2H-pyran-4-yl)ethynyl)picolinaldehyde oxime 3o:

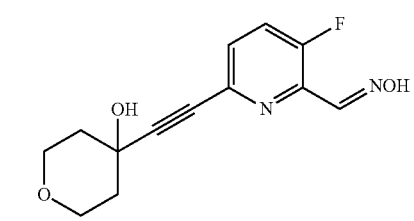

3-fluoro-6-((3-hydroxyoxetan-3-yl)ethynyl)picolinaldehyde oxime 3p:

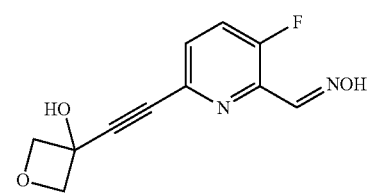

Benzyl 3-((5-fluoro-6-((hydroxyimino)methyl)pyridin-2-yl)ethynyl)azetidine-1-carboxylate 3q:

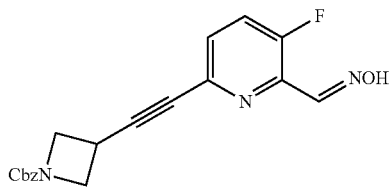

3-fluoro-6-(pyridin-3-ylethynyl)picolinaldehyde oxime 3r:

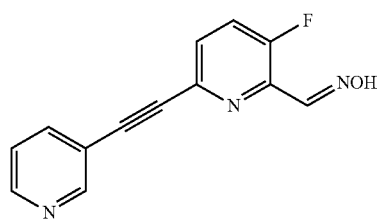

Benzyl (3-(5-fluoro-6-((hydroxyimino)methyl)pyridin-2-yl)prop-2-yn-1-yl)(pyridin-4-yl)carbamate 3s:

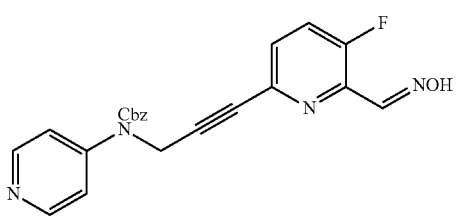

Methyl (S)-2-((tert-butoxycarbonyl)amino)-5-(5-fluoro-6-((hydroxyimino)methyl)pyri-din-2-yl)pent-4-ynoate 3t:

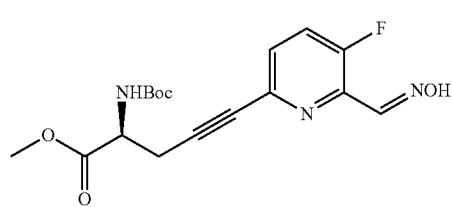

N-(9-((3aR,4R,6R,6aR)-6-(((3-(5-fluoro-6-((hydroxyimino)methyl)pyridin-2-ylprop-2-yn-1-yl)oxy)methyl)-2,2-dimethyltetrahydrofuro[3,4-d][1,3]dioxol-4-yl)-9H-purin-6-yl)benzamide 3u:

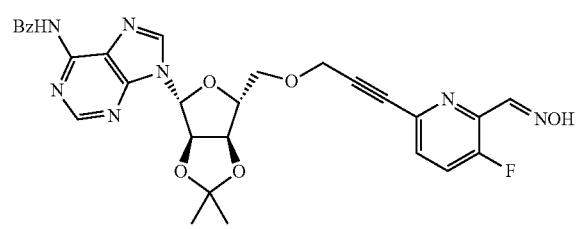

(3aS,4S,6R,6aR)-6-(6-amino-9H-purin-9-yl-N-(4-(5-fluoro-6-((Z)-(hydroxyimino)me-thyl)pyridin-2-yl)but-3-yn-1-yl)-2,2-dimethyltetrahydrofuro[3,4-d][1,3]dioxole-4-carboxamide 3v:

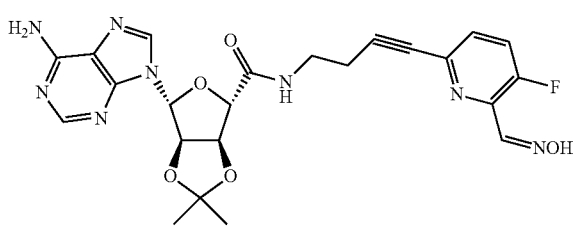

3v 3-fluoro-6-(10-(5-fluoro-6-((E)-(hydroxyimino)methyl)pyridin-2-yl)deca-1,9-diyn-1-yl)picolinaldehyde oxime 3w:

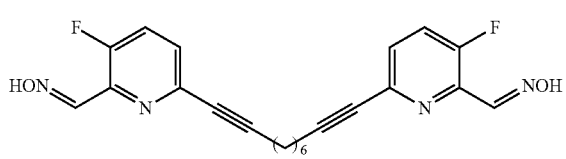

3w

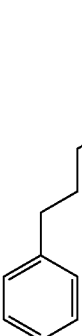

6-(4-((7-chloro-2,3-dihydro-1H-cyclopenta[b]quinolin-9-yl)amino)but-1-yn-1-yl)-3-flu-oropicolinaldehyde oxime 3λ:

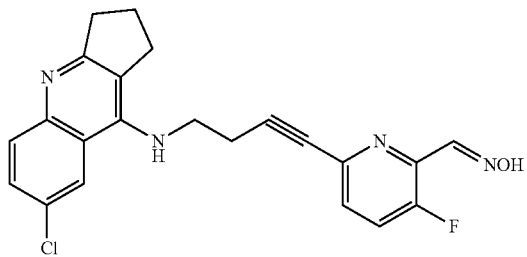

3x 3-fluoro-6-(4-(quinolin-4-ylamino)but-1-yn-1-yl)picolinaldehyde oxime 3y:

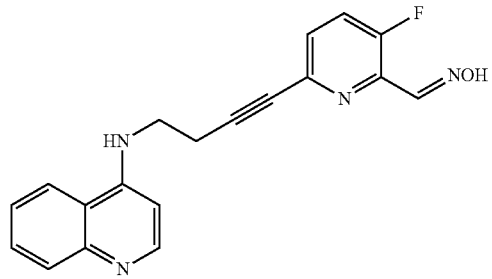

3y 6-(4-(1,2,3,4-tetrahydroacridin-9-ylamino)but-1-yn-1-yl)-3-fluoropicolinaldehyde oxime 3z:

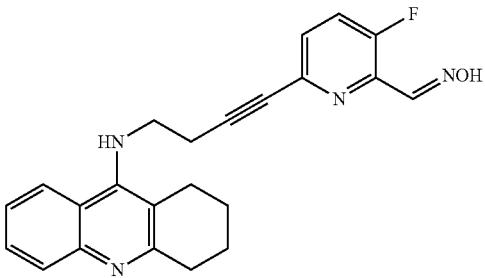

3z 6-bromo-3-fluoropicolinaldehyde oxime (Labelled) 4:

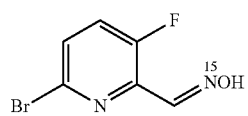

4

3-fluoro-6-(5-phenylpent-1-yn-1-yl)picolinaldehyde oxime 5 (labelled):

5

6-bromo-3-fluoro-N'-hydroxypicolinimidamide 7:

7

6-bromo-3-fluoro-N'-hydroxypicolinimidamide (Labelled) 8:

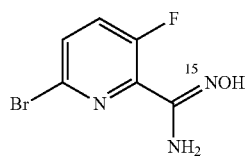

8

3-fluoro-6-(5-phenylpent-1-yn-1-yl)picolinonitrile 9:

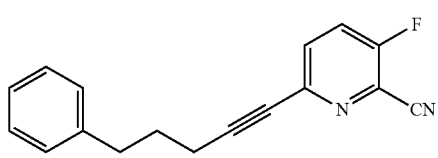

3-fluoro-N'-hydroxy-6-(5-phenylent-1-yn-1-yl)picolinimidamide 10:

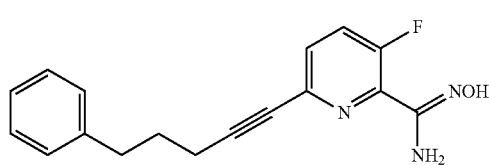

3-fluoro-N-hydroxy-6-(5-phenylpent-1-yn-1-yl)picolinamide 12:

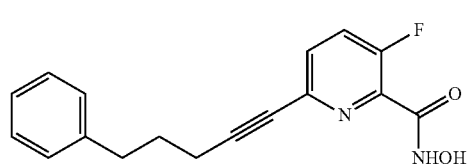

3-fluoro-6-(5-phenylpentyl)picolinaldehyde oxime 13:

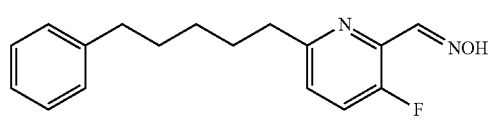

6-(3-cyclohexylpropyl)-3-fluoropicolinaldehyde oxime 14:

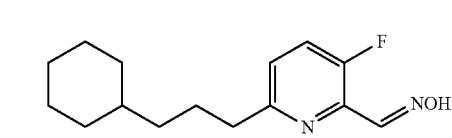

6-(4-ethylphenethyl)-3-fluoropicolinaldehyde oxime 15:

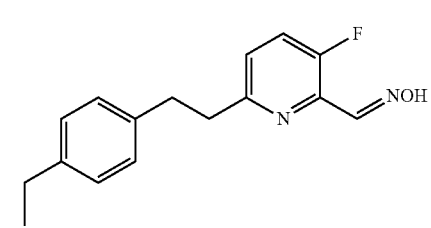

3-fluoro-6-(2-(pyridin-3-yl)ethyl)picolinaldehyde oxime 16:

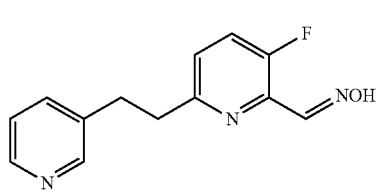

3-fluoro-6-(2-(3-hydroxyoxetan-3-yl)ethyl)picolinaldehyde oxime 17:

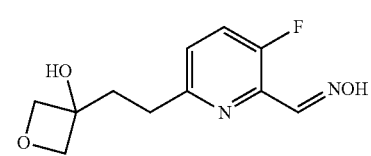

3-fluoro-6-(2-(4-hydroxytetrahydro-2H-pyran-4-yl)ethyl)picolinaldehyde oxime 18:

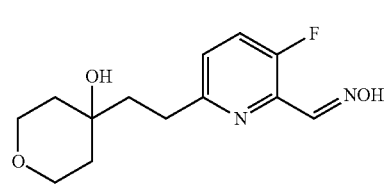

3-fluoro-6-(10-(5-fluoro-6-((hydroxyimino)methyl)pyridin-2-yl)decyl)picolin-aldehyde oxime 19:

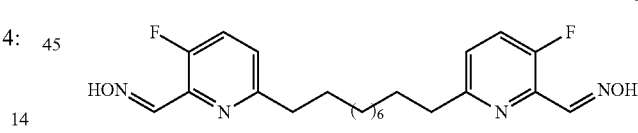

N-(9-((3aR,4R,6R,6aR)-6-((3-(5-fluoro-6-((hydroxyimino)methyl)pyridin-2-yl)propoxy)methyl)-2,2-dimethyltetrahydrofuro[3,4-d][1,3]dioxol-4-yl)-9H-purin-6-yl)benzamide 20:

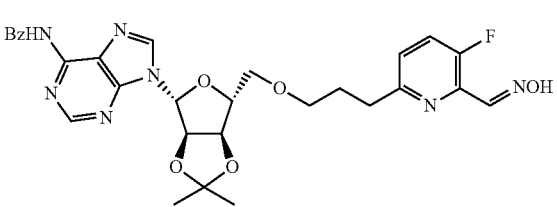

3-fluoro-6-((E)-6-hydroxyhex-1-en-1-yl)picolinaldehyde oxime 21:

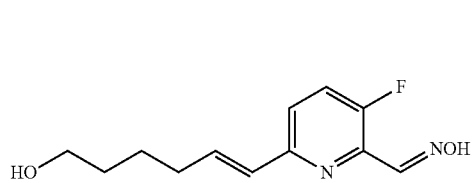

Methyl (E)-6-(5-fluoro-6-((hydroxyimino)methyl)pyridin-2-yl)hex-5-enoate 22:

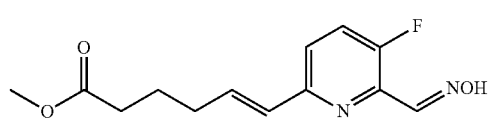

3-fluoro-6-((E)-2-(pyren-4-yl)vinyl)picolinaldehyde oxime 23:

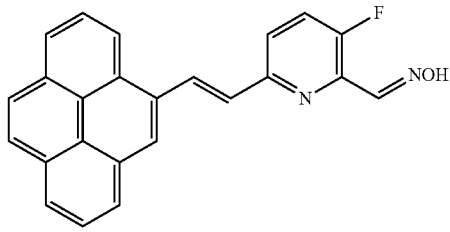

3-fluoro-6-(4-((1,2,3,4-tetrahydroacridin-9-yl)amino)butyl)picolinaldehyde oxime 24:

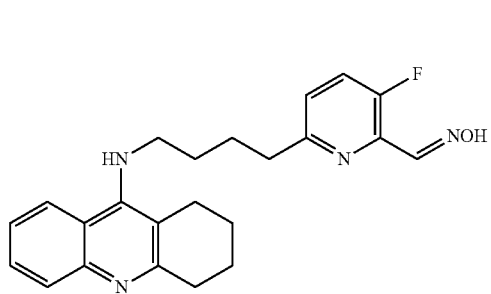

9-((4-(5-fluoro-6-((hydroxyimino)methyl)pyridin-2-yl)butyl)amino)-1,2,3,4-tetrahydroacridin-10-ium chloride 25:

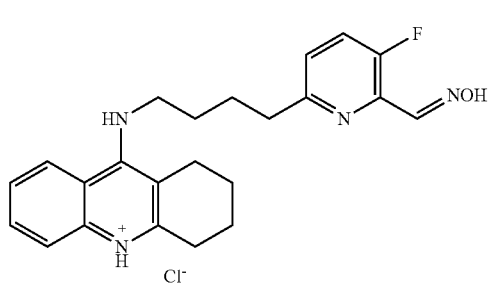

3-fluoro-6-(4-(quinolin-4-ylamino)but-1-yn-1-yl)picolinaldehyde oxime 26:

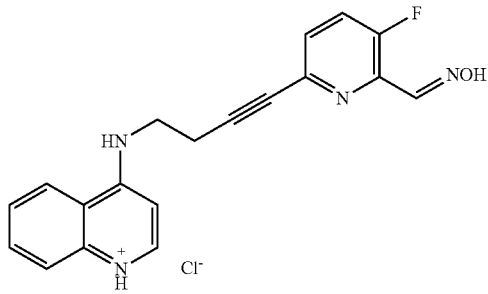

3-fluoro-6-(4-(quinolin-4-ylamino)butyl)picolinaldehyde oxime 27:

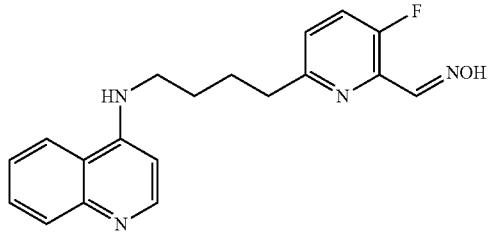

4-((4-(5-fluoro-6-((hydroxyimino)methyl)pyridin-2-yl)butyl)ammonio)quinolin-1-ium chloride 28:

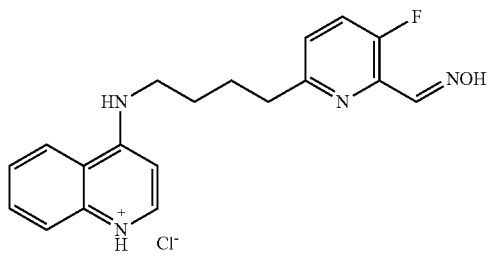

3-((5-fluoro-6-((hydroxyimino)methyl)pyridin-2-yl)ethynyl)pyridin-1-ium chloride 29:

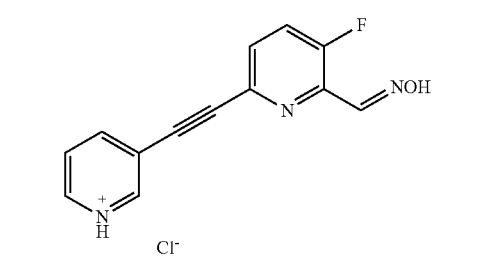

and 3-(2-(5-fluoro-6-((hydroxyimino)methyl)pyridin-2-yl)ethyl)pyridin-1-ium-chloride 30:

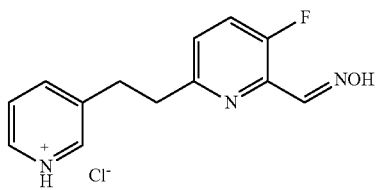

3-fluoro-N'-hydroxy-6-(pentadec-1-yn-1-yl)picolinimidamide 46:

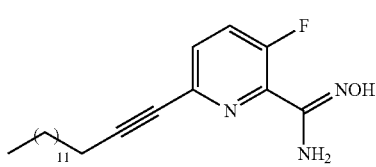

6-((4-ethylphenyl)ethynyl)-3-fluoro-N'-hydroxypicolinimidamide 47:

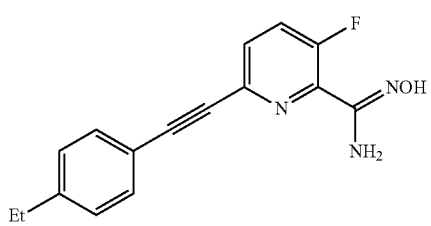

3-fluoro-N'-hydroxy-6-(4-morpholinobut-1-yn-1-yl)picolinimidamide 48:

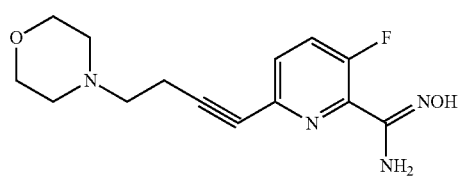

3-fluoro-N'-hydroxy-6-((3-hydroxyoxetan-3-yl)ethynyl)picolinimidamide 49:

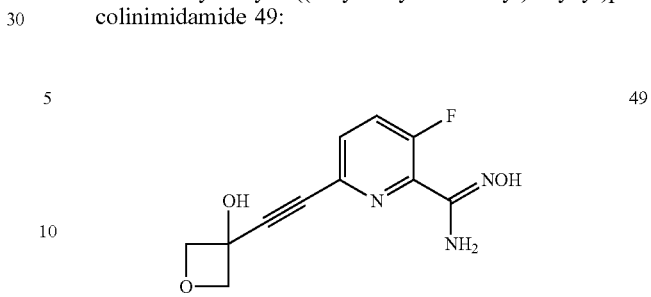

6-((1-aminocyclohexyl)ethynyl)-3-fluoro-N'-hydroxypicolinimidamide 50:

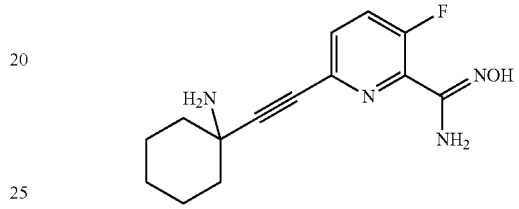

(3aS,4S,6R,6aR)-6-(6-amino-9H-purin-9-yl)-N-(4-(5-fluoro-6-((E)-N'-hydroxycarbamimidoyl)pyridin-2-yl)but-3-yn-1-yl)-2,2-dimethyltetrahydrofuro[3,4-d][1,3]dioxole-4-carboxamide 51:

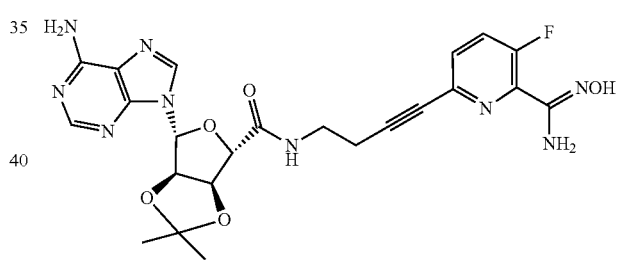

Preparation of the Compounds of Formula (II)

A compound of formula (II) according to the invention may be synthesized by any appropriate method. For example, the compounds of formula (II) may be prepared according to the following scheme:

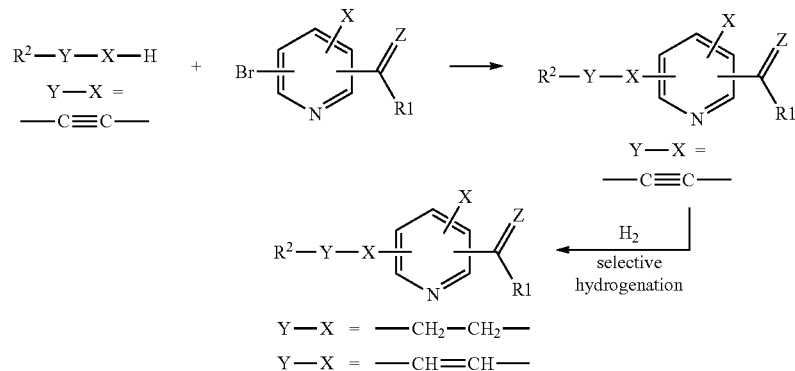

The compound of formula (II), wherein X—Y is Br, is reacted with R2-X—Y—H (wherein X—Y is —C≡C—), in order to obtain the compound of formula (II) wherein X—Y is —C≡C—.

Then, by selective hydrogenation (thanks to H2), one can easily obtain either the compound of formula (II) wherein X—Y is —CH═CH—, or the compound of formula (II) wherein X—Y is —CH2-CH2-.

Such methods are exemplified in the following examples.

Preparation of the Compounds of Formula (I)

A compound of formula (I) according to the invention may be synthesized by any appropriate method known by anyone of ordinary skill in the art.

Preferably, the compounds of formula (I) are synthetized as described below. Such a process is chemoselective. Particularly, it does not necessitate any previous protection step of the oxime, amidoxime or hydroxamic acid. Said process comprises a minimal number of steps (one or two), is quickly performed, at ambient temperature.

Scaffold 1

Particularly, the compounds of Scaffold 1:

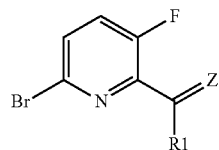

Scaffold 1, wherein R1 and Z are as follows: R1 is H and Z is ═NOH; or R1 is NH2 and Z is ═NOH, may be obtained by reacting the picolinaldehyde precursor with hydroxylamine hydrochloride or by reacting the picolinonitrile derivative with hydroxylamine hydrochloride, preferably in an organic solvent. In all cases hydroxylamine hydrochloride may be labelled with $^{15}$N element.

Such synthesis are illustrated for 6-bromo-3-fluoropicolinaldehyde oxime 2 and 4 (i.e. R1 is H and Z is ═NOH or ═$^{15}$NOH), and for 6-bromo-3-fluoro-N'-hydroxypicolinimidamide 7 and 8 (i.e. R1 is NH2 and Z is ═NOH or ═$^{15}$NOH) in the examples.

The compound of Scaffold 1, wherein R1 is —NHOH and Z is O, is 6-bromo-3-fluoro-2-pyridinhydroxamic acid and was purchased from Aldrich.

Scaffold 2

In particular, the process for the synthesis of compounds of formula (I), scaffold (2), may comprise, preferably consists in, a late step of Sonogashira coupling reaction between a compound of scaffold 1, i.e. a 6-bromo-3-fluoro-2-pyridinaldoxime, a 6-bromo-3-fluoro-2-pyridinhydroxamic acid or a 6-bromo-3-fluoro-2-pyridinamidoxime, and a compound comprising a terminal alkyne. This corresponds to the following scheme:

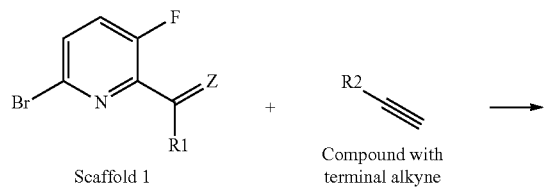

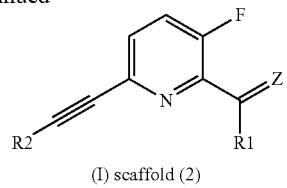

(I) scaffold (2)

Such a Sonogashira coupling reaction may be performed in the presence of a solvent such as tetrahydrofurane (THF), triethylamine (Et$_3$N), preferably a mixture thereof; in the presence of a catalyst such as Pd[PPh$_3$]$_4$ and CuI.

When Z is ═N—OH and R1 is H (i.e. thus forming an oxime moiety), such a Sonogashira step is performed without any protection of the oxime moiety.

In the particular case where R2 is an alkyl group linked to the following radical:

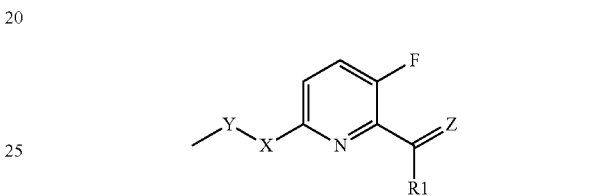

the compounds of formula (I) may be obtained by the step of Sonogashira coupling reaction between two compounds of scaffold 1, identical or different, i.e. a 6-bromo-3-fluoro-2-pyridinaldoxime, a 6-bromo-3-fluoro-2-pyridinhydroxamic acid or a 6-bromo-3-fluoro-2-pyridinamidoxime, and a dialkyne compound having two terminal alkyne groups HC≡C—R'2-C≡CH wherein R'2 is an alkyl group.

Scaffolds 3 and 4

Then, the resulting alkyne (scaffold 2) may be reduced by reaction with hydrogen, for instance in presence of Pd/C catalyst, to obtain the corresponding alkene (scaffold 3) or alkyl (scaffold 4); this is the selective hydrogenation step.

Again, for this hydrogenation step, when Z is ═N—OH and R1 is H (i.e. thus forming an oxime moiety), the hydrogenation step is performed without any protection of the oxime moiety.

Thus, an object of the invention is a process for preparing a compound of formula (I), wherein —X—Y— is —CH2-CH2-, —C≡C— or —CH═CH— and R1, R2 and Z are as defined above, comprising a Sonogashira coupling reaction between a 6-bromo-3-fluoro-2-pyridinaldoxime, a 6-bromo-3-fluoro-2-pyridinhydroxamic acid or a 6-bromo-3-fluoro-2-pyridinamidoxime and a compound comprising a terminal alkyne or a dialkyne compound having two terminal alkyne groups, optionally followed by a reduction step by reaction with hydrogen.

Pharmaceutical Uses of the Compounds of the Invention

The compounds of this invention, and 6-bromo-3-fluoro-2-pyridine hydroxamic acid, may be used in the treatment of a nervous and/or respiratory failure due to intoxication with at least one organophosphorous nerve agent which may preferably be selected from warfare agents such as O-ethyl S-[2-(diisopropylamino)ethyl] methylphosphonothioate (VX), tabun, sarin, cyclosarin and soman and pesticides such as paraoxon, parathion and tetraethyl pyrophosphate (TEPP). The compounds of the invention may be used in the treatment of a nervous and/or respiratory failure due to intoxication with at least one organophosphorous nerve agent, by virtue of their reactivation potency of organophosphorous inhibited cholinesterases, including acetylcholinesterase and butyrylcholinesterase. These compounds may alternatively be used in the treatment of diseases, which involve a reduced production of acetylcholine that may be overcome by the administration of acetylcholinesterase inhibitors. Examples of such diseases include in particular neurological diseases such as Alzheimer's disease.

These compounds may alternatively be used in the treatment of cancer, thanks to their action as inhibitors of histone deacetylases (HDAC).

These compounds may alternatively be used as antiviral drugs.

The compound of this invention is usually included in a pharmaceutical composition comprising at least one compound according to the invention and a pharmaceutically acceptable support.

The amount of compound of formula (II) or (I) in the composition according to the invention may vary in a broad range depending upon the patient, the mode of administration and the expected effect.

The compound or composition according to the invention can be administered orally or non-orally, for instance via topical, parenteral, intramuscular, intravenous, cutaneous, nasal or rectal route.

The pharmaceutical composition of the invention can present different forms including granules, powders, tablets, capsules, syrups, emulsions, suspensions, and forms used for non-oral administration, for instance injections, sprays, transdermal patches or suppositories. These pharmaceutical forms can be prepared via known conventional techniques.

The preparation of an orally administered solid pharmaceutical form can be for instance performed by the following process: an excipient (for example lactose, sucrose, starch or mannitol), a desintegrant (for example calcium carbonate, calcium carboxymethylcellulose, alginic acid, sodium carboxymethylcellulose, colloidal silicon dioxide, sodium croscarmellose, crospovidone, guar gum, magnesium aluminium silicate, microcrystalline cellulose, cellulose powder, pregelatinised starch, sodium alginate or starch glycolate), a binder (for example alpha-starch, gum arabic, carboxymethylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose or guar gum) and a lubricant (for example talc, magnesium stearate or polyethylene 6000) are added to the active principle and the mixture obtained is then tabletted. If necessary, the tablet can be coated via the known techniques, in order to mask the taste (for example with cocoa powder, mint, borneol or cinnamon powder) or to allow enteric dissolution or sustained release of the active principles. Coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide or quinoline yellow lake).

Liquid pharmaceutical forms for oral administration include solutions, suspensions and emulsions. The aqueous solutions can be obtained by dissolving the active principle in water, followed by addition of flavourings, colorants, stabilisers and/or thickeners, if necessary. In order to improve the solubility, it is possible to add ethanol, propylene glycol or any other pharmaceutically acceptable non-aqueous solvent. The aqueous suspensions for oral use can be obtained by dispersing the finely divided active principle in water with a viscous product, such as a natural or synthetic gum or resin, methylcellulose or sodium carboxymethylcellulose.

The pharmaceutical forms for injection can be obtained, for example, by the following process. The active principle is dissolved, suspended or emulsified either in an aqueous medium (for example distilled water, physiological saline or Ringer's solution) or in an oily medium (for example olive oil, sesame seed oil, cottonseed oil, corn oil or propylene glycol), with a dispersant (for example Tween® 80, HCO® 60 (Nikko Chemicals), polyethylene glycol, carboxymethylcellulose or sodium alginate), a preserving agent (for example methyl p-hydroxybenzoate, propyl p-hydroxybenzoate, benzyl alcohol, chlorobutanol or phenol), an isotonicity agent (for example sodium chloride, glycerol, sorbitol or glucose) and optionally other additives, such as, if desired, a solubilizing agent (for example sodium salicylate or sodium acetate) or a stabilizer (for example human serum albumin).

Pharmaceutical forms for external use (topical use) can be obtained from a solid, semi-solid or liquid composition containing the active principle. For example, to obtain a solid form, the active principle can be treated with excipients (for example lactose, mannitol, starch, microcrystalline cellulose or sucrose) and a thickener (for example natural gums, cellulose derivatives or acrylic polymers) so as to convert them into powder. The liquid pharmaceutical compositions are prepared in substantially the same way as the forms for injection, as indicated previously. The semi-solid pharmaceutical forms are preferably in the form of aqueous or oily gels or in the form of pomades. These compositions may optionally contain a pH regulator (for example carbonic acid, phosphoric acid, citric acid, hydrochloric acid or sodium hydroxide) and a preserving agent (for example a p-hydroxybenzoic acid ester, chlorobutanol or benzalkonium chloride).

A method for the treatment of a nervous and/or respiratory failure due to intoxication with at least one organophosphorous nerve agent, comprising administering at least one compound according to the invention is also described herein.

A method for the treatment of a neurological disease such as Alzheimer's disease, comprising administering at least one compound according to the invention is also described herein.

A method for the treatment of a cancer, comprising administering at least one compound according to the invention is also described herein.

A method for the treatment of a virus, comprising administering at least one compound according to the invention is also described herein.

Within the context of the invention, the term treatment denotes curative, symptomatic, and/or preventive treatments. In particular, it can refer to reducing the progression of the disease, reducing or suppressing at least one of its symptoms or complications, or improving in any way the state of health of patients.

The administration of the compounds or of the composition according to the invention may be performed before, during or after the exposition of the subject to the organophosphorous nerve agent.

In the present invention, the terms "subject" and "patient" are used indifferently and designate a human subject.

The amount of compound of formula (II) or (I) to be administered according to the invention may vary in a broad range depending upon the patient, the mode of administration and the expected effect. In particular, the amount of compound of formula (II) or (I) may be comprised between 200 mg and 4000 mg, with up to 3 daily intakes.

The compound or composition according to the invention may be co-administered with at least one other active agent, such as an antimuscarinic agent, in particular atropine, an anticonvulsant, in particular diazepam or one of its prodrugs, such as avizafone, and/or a bioscavenger able to capture and/or degrade OPNAs in blood, such as human butyrylcholinesterase.

The term co-administered means that the administration of the compound or composition according to the invention and that of the other active agent can be simultaneous, sequential and/or separate.

Other Uses of the Compounds of the Invention

The compounds of this invention may further be used as tools for in vivo and/or in vitro biological studies. In this application, the compounds of formula (II) or (I) may include one or more isotopes, which will allow for their detection.

The following examples are provided as illustrative, and not limitative, of the present invention.

EXAMPLES

Example 1: Synthesis of Compounds of the Invention

I—General Methods

All starting materials and reagents were purchased from commercial sources, and used as received without further purification. Air and $H_2O$ sensitive reactions were performed in flame dried glassware under Ar atmosphere. Moisture sensitive reagents were introduced via a dry syringe. Anhydrous solvents were supplied over molecular sieves, and used as received. Petroleum ether (PE) refers to the 40-60° C. boiling fraction. Reactions were monitored by thin-layer chromatography (TLC) with silica gel 60 $F_{254}$ 0.25 mm pre-coated glass plates. Compounds were visualized by using $UV_{254}$ and/or phosphomolybdic acid stain [3 g $12MoO_3.H_3PO_4.xH_2O$ in 100 mL EtOH] followed by heating with a heat gun. Flash column chromatography was performed using Macherey-Nagel silica gel 60 (15-40 µm). NMR experiments were recorded with a Bruker Avance 400 spectrometer at 400 MHz for $^1H$ nuclei and at 100 MHz for $^{13}C$ nuclei. The chemical shifts are expressed in part per million (ppm) relative to TMS ($\delta$=0 ppm) and the coupling constant J in Hertz (Hz). NMR multiplicities are reported using the following abbreviations: br=broad, s=singlet, d=doublet, t=triplet, q=quadruplet, m=multiplet. HRMS were recorded on a Bruker micrOTOF spectrometer.

II—Experimental Procedures

A) With 6-bromo-3-fluoropicolinaldehyde oxime (Compound 2)

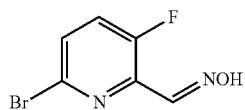

2

A solution of picolinaldehyde (2 g, 9.804 mmol, 1 equiv), hydroxylamine hydrochloride (2.7 g, 19.61 mmol, 2 equiv), and $CH_3CO_2Na$ (2.4 g, 29.412 mmol, 3 equiv) in dry ethanol (75 mL) was stirred at reflux during 16 h. After completion (checked by TLC), the reaction mixture was filtered through a small celite pad. The filtrate was concentrated under reduced pressure and the residue was purified by column chromatography (EtOAc/PE 1:9) to afford the oxime 2 as a white solid (2.1 g, quant. yield). $R_f$ (20% EA+PE) 0.50; IR (neat) $v_{max}$ cm$^{-1}$ 3248, 1579, 1442, 1287, 1236, 1187, 1108, 985, 937, 825, 720, 669, 620, 521; $^1H$ NMR (400 MHz, $CD_3OD$) $\delta$ (ppm) 8.18 (s, 1H, $H_7$), 7.61-7.55 (m, 2H, $H_4$, $H_5$); $^{13}C$ NMR (100 MHz, $CD_3OD$) $\delta$ (ppm) 160.21, *157.60 (C3), 144.54, *144.50 (C13), 142.24, *142.12 (C2), 136.78, *136.75 (C6), 131.05, *131.0 (C5), 128.95, *128.74 (C4) (* doubling of the peaks were observed due to the coupling of carbons with fluorine atom); HRMS (ESI$^+$) m/z calcd for $C_6H_5Br_1F_1N_2O_1{}^+$ 218.9564 found 218.9564.

a) Synthesis 3-fluoro-6-(5-phenylpent-1-yn-1-yl) picolinaldehyde oxime (Compound 3a)

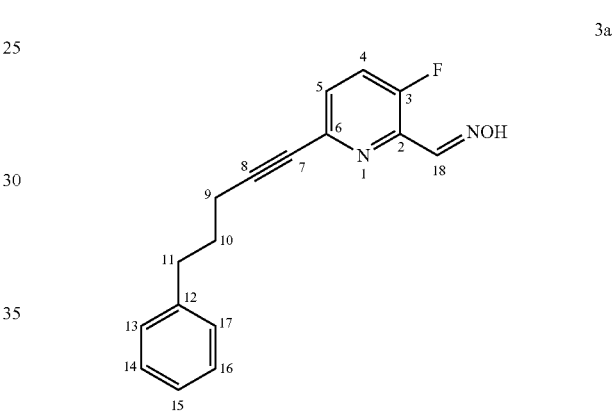

3a

Method 1:

To a degassed solution of oxime 2 (249 mg, 1.144 mmol, 1.1 equiv) in THF/$Et_3N$ (8 mL/3 mL), Pd[PPh$_3$]$_4$ (180 mg, 0.156 mmol, 0.15 equiv) and CuI (60 mg, 0.312 mmol, 0.3 equiv) were added. After degassing the reaction mixture for 5 min at room temperature, the alkyne 1a (5-phenyl-1-pentyne, 150 mg, 1.04 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 3a as a white solid (270 mg, 92%). $R_f$ (20% EA+PE) 0.40; IR (neat) $v_{max}$ 3246, 2943, 2228, 1466, 1238, 973, 849, 693, 707, 653, 567, 463 cm$^{-1}$; $^1H$ NMR (400 MHz, CDCl$_3$) $\delta$ (ppm) 9.46 (br s, 1H, OH), 8.26 (s, 1H, $H_{18}$), 7.36-7.11 (m, 7H, Ar), 2.71 (t, J=7.5 Hz, 2H, $H_{11}$), 2.37 (t, J=7.1 Hz, 2H, $H_9$), 1.88 (quintet, J=7.1, 7.5 Hz, 2H, $H_{10}$); $^{13}C$ NMR (100 MHz, CDCl$_3$) $\delta$ (ppm) 158.04, *155.39 (C3), 145.78, *145.73 (C18), 141.27 (C12), 140.04, *139.99 (C2), 139.53, *139.42 (C6), 128.47, 128.39, 128.34 (C5, C13, C14, C16, C17), 125.93 (C15), 124.60, *124.40 (C4), 91.07 (C7), 79.42 (C8), 34.83 (C11), 29.70 (C10), 18.67 (C9) (* doubling of the peaks were observed due to the coupling of carbons with fluorine atom); $^{19}F$ NMR (400 MHz, CDCl$_3$) $\delta$ (ppm) −122.42; HRMS (ESI$^+$) m/z calcd for $C_{17}H_{16}F_1N_2O_1{}^+$ 283.1210 found 283.1241.

Method 2:

To a degassed solution of oxime 2 (83 mg, 0.381 mmol, 1.1 equiv) in THF/Et$_3$N (2 mL/1 mL), Pd[PPh$_3$]$_4$ (40 mg, 0.035 mmol, 0.1 equiv) and CuI (13 mg, 0.070 mmol, 0.2 equiv) were added. After degassing the reaction mixture for 2 min at room temperature, the alkyne 1a (5-phenyl-1-pentyne, 50 mg, 0.348 mmol, 1 equiv) was added dropwise and the reaction mixture was subjected to microwave irradiation for 30 min. After completion (monitored by TLC), the reaction mixture was concentrated under reduced pressure and the residue was purified by column chromatography (EtOAc/PE 1:9) to afford the desired coupled fluoro oxime 3a as a white solid (90 mg, 92%).

b) 3-fluoro-6-(pentadec-1-yn-1-yl)picolinaldehyde oxime (Compound 3b)

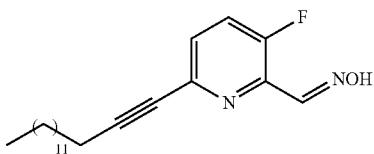

3b

To a degassed solution of oxime 2 (60 mg, 0.240 mmol, 1.1 equiv) in THF/Et$_3$N (4 mL/2 mL), Pd[PPh$_3$]$_4$ (42 mg, 0.036 mmol, 0.15 equiv) and CuI (14 mg, 0.072 mmol, 0.3 equiv) were added. After degassing the reaction mixture for 5 min at room temperature, the alkyne 1b (1-pentadecyne, 50 mg, 0.240 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 6:94) to afford the desired coupled fluoro oxime 3b as a white solid (64 mg, 77%). R$_f$ (20% EA+PE) 0.70; IR (neat) v$_{max}$ 3293, 2918, 2850, 2225, 1580, 1465, 1243, 1186, 997, 986, 835, 717, 652, 562 cm$^{-1}$; $^1$H NMR (400 MHz, CDCl$_3$) δ (ppm) 9.04 (br s, 1H, OH), 8.31 (s, 1H, H$_{22}$), 7.41-7.32 (m, 2H, Ar), 2.40 (t, J=7.1 Hz, 2H, H$_9$), 1.60 (quintet, J=7.1, 7.4 Hz, 2H, H$_{10}$), 1.41 (m, 2H, H$_{11}$), 1.23 (s, 1H, H$_{12}$—H$_{20}$), 0.85 (t, J=6.7 Hz, 1H, H$_{21}$); $^{13}$C NMR (100 MHz, CDCl$_3$) δ (ppm) 158.09, *155.44 (C3), 146.18, *146.13 (C22), 140.29, *140.24 (C2), 139.48, *139.37 (C6), 128.51, *128.46 (C5), 124.60, *124.40 (C4), 91.80 (C7), 79.00 (C8), 31.94, 29.67, 29.52, 29.37, 29.16, 29.03, 28.28, 22.71, 19.36, 14.14 (C9-C21), 29.70 (C10), 18.67 (C9) (* doubling of the peaks were observed due to the coupling of carbons with fluorine atom); $^{19}$F NMR (400 MHz, CDCl$_3$) δ (ppm) -122.58; HRMS (ESI$^+$) m/z calcd for C$_{21}$H$_{32}$F$_1$N$_2$O$_1$$^+$ 347.2461 found 347.2493.

c) 6-(3-cyclohexylprop-1-yn-1-yl)-3-fluoropicolinaldehyde oxime (Compound 3c)

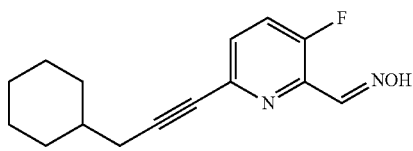

3c

To a degassed solution of oxime 2 (89 mg, 0.409 mmol, 1 equiv) in THF/Et$_3$N (5 mL/2 mL), Pd[PPh$_3$]$_4$ (71 mg, 0.061 mmol, 0.15 equiv) and CuI (23 mg, 0.123 mmol, 0.3 equiv) were added. After degassing the reaction mixture for 5 min at room temperature, the alkyne 1c (3-cyclohexyl-1-propyne, 50 mg, 0.409 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 3c as a white solid (60 mg, 56%). R$_f$ (20% EA+PE) 0.55; IR (neat) v$_{max}$ 3282, 2921, 2849, 2229, 1579, 1460, 1239, 1179, 983, 835, 711, 655, 557, 464 cm$^{-1}$; $^1$H NMR (400 MHz, CDCl$_3$) δ (ppm) 9.50 (s, 1H, OH), 8.30 (s, 1H, H$_{16}$), 7.42-7.31 (m, 2H, H$_4$, H$_5$), 2.30 (d, J=6.6 Hz, 2H, H$_9$), 1.84 (d, J=12.7 Hz, 2H, Cyhexyl), 1.71-1.51 (m, 4H, Cyhexyl), 1.33-0.95 (m, 5H, Cyhexyl); $^{13}$C NMR (100 MHz, CDCl$_3$) δ (ppm) 158.01, *155.36 (C3), 146.08, *146.03 (C16), 140.24, *140.20 (C2), 139.45, 139.34 (C6), 128.46, *128.41 (C5), 124.56, *124.36 (C4), 90.74 (C7), 79.84 (C8), 37.12, 32.80, 27.07, 26.15, 26.06 (C9-C15) (* doubling of the peaks were observed due to the coupling of carbons with fluorine atom); $^{19}$F NMR (400 MHz, CDCl$_3$) δ (ppm) -122.60; HRMS (ESI$^+$) m/z calcd for C$_{15}$H$_{18}$F$_1$N$_2$O$_1$$^+$ 261.1427 found 261.1398.

d) 3-fluoro-6-(6-hydroxyhex-1-yn-1-yl)picolinaldehyde oxime (Compound 3d)

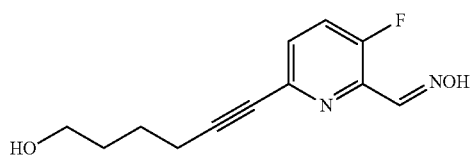

3d

To a degassed solution of oxime 2 (111 mg, 0.51 mmol, 1 equiv) in THF/Et$_3$N (5 mL/2 mL), Pd[PPh$_3$]$_4$ (89 mg, 0.077 mmol, 0.15 equiv) and CuI (29 mg, 0.153 mmol, 0.3 equiv) were added. After degassing the reaction mixture for 5 min at room temperature, the alkyne 1d (5-hexyne-1-ol, 50 mg, 0.51 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:1) to afford the desired coupled fluoro oxime 3d as a white solid (100 mg, 83%). R$_f$ (pure EA) 0.65; IR (neat) v$_{max}$ 3245, 3077, 2937, 2424, 2235, 1723, 1584, 1472, 1463, 1270, 1251, 1191, 1056, 1026, 992, 972, 861, 730, 714, 653, 545 cm$^{-1}$; $^1$H NMR (400 MHz, CD$_3$OD) δ (ppm) 8.21 (s, 1H, H$_{13}$), 7.60 (dd, J=8.6, 9.8 Hz, 1H, H$_4$), 7.45 (dd, J=3.8, 8.6 Hz, 1H, H$_5$), 3.62 (t, J=6.1 Hz, 2H, H$_{12}$), 2.49 (t, J=6.6 Hz, 2H, H$_9$), 1.71 (m, 4H, H$_{10}$, H$_{11}$); $^{13}$C NMR (100 MHz, CD$_3$OD) δ (ppm) 159.53, *156.89 (C3), 145.01, *144.97 (C13), 141.54, *141.42 (C2), 141.30, *141.25 (C6), 129.97, *129.92 (C5), 126.39, *126.19 (C4), 92.21 (C7), 80.30 (C8), 62.52 (C12), 32.93 (C11ss), 26.01 (C10), 19.78 (C9) (* doubling of the peaks were observed due to the coupling of carbons with fluorine atom); $^{19}$F NMR (400 MHz, CDCl$_3$) δ (ppm) -125.01; HRMS (ESI$^+$) m/z calcd for C$_{12}$H$_{14}$F$_1$N$_2$O$_2$$^+$ 237.1009 found 237.1034.

e) Methyl 6-(5-fluoro-6-((hydroxyimino)methyl)pyridin-2-yl)hex-5-ynoate (Compound 3e)

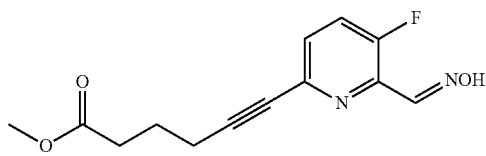

To a degassed solution of oxime 2 (86 mg, 0.396 mmol, 1 equiv) in THF/Et$_3$N (5 mL/2 mL), Pd[PPh$_3$]$_4$ (69 mg, 0.059 mmol, 0.15 equiv) and CuI (23 mg, 0.119 mmol, 0.3 equiv) were added. After degassing the reaction mixture for 5 min at room temperature, the alkyne 1e (methyl 5-hexynoate, 50 mg, 0.396 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:3) to afford the desired coupled fluoro oxime 3e as a white solid (90 mg, 86%). R$_f$ (50% EA+PE) 0.55; IR (neat) v$_{max}$ 3291, 2951, 2235, 1728, 1582, 1480, 1250, 1239, 1171, 1107, 973, 834, 717, 654, 568, 461 cm$^{-1}$; $^1$H NMR (400 MHz, CDCl$_3$) δ (ppm) 9.05 (s, 1H, OH), 8.31 (s, 1H, H$_{15}$), 8.42-8.31 (m, 2H, H$_4$, H$_5$), 3.66 (s, 1H, H$_{14}$), 2.49 (t, J=7.2 Hz, 4H, H9, H$_{11}$), 1.93 (quintet, J=7.2 Hz, 2H, H$_{10}$); $^{13}$C NMR (100 MHz, CDCl$_3$) δ (ppm) 173.46 (C14), 158.12, *155.47 (C3), 145.81, *145.75 (C15), 139.88, *139.83 (C2), 139.56, *139.46 (C6), 128.54, *128.49 (C5), 124.56, *124.40 (C4), 89.98 (C7), 79.75 (C8), 51.64 (C14), 32.83 (C11), 23.37 (C10), 18.73 (C9) (* doubling of the peaks were observed due to the coupling of carbons with fluorine atom); $^{19}$F NMR (400 MHz, CDCl$_3$) δ (ppm) -122.46; HRMS (ESI$^+$) m/z calcd for C$_{13}$H$_{14}$F$_1$N$_2$O$_3^+$ 265.0968 found 265.0983.

f) 6-((1-aminocyclohexyl)ethynyl)-3-fluoropicolinaldehyde oxime (Compound 3f)

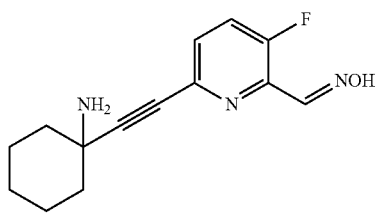

To a degassed solution of oxime 2 (88 mg, 0.406 mmol, 1.1 equiv) in THF/Et$_3$N (4 mL/2 mL), Pd[PPh$_3$]$_4$ (47 mg, 0.041 mmol, 0.1 equiv) and CuI (15 mg, 0.081 mmol, 0.2 equiv) were added. After degassing the reaction mixture for 5 min at room temperature, the alkyne 3f (1-ethynyl-cyclohexylamine, 50 mg, 0.406 mmol, 1 equiv) was added dropwise and the reaction mixture was stirred at the room temperature for 16 h. After completion (checked by TLC), the reaction mixture was concentrated under reduced pressure and the residue was purified by column chromatography (pure EtOAc to MeOH/EtOAc 5:95) to afford the desired coupled fluoro oxime 4f as a light yellowish solid (90 mg, 85%). R$_f$ (5% MeOH+EA) 0.30; IR (neat) v$_{max}$ 3280, 3323, 2936, 2858, 2561, 1812, 1579, 1523, 1459, 1245, 1164, 1058, 1006, 973, 931, 840, 677, 622, 529, 453 cm$^{-1}$; H NMR (400 MHz, DMSO-d6) δ (ppm) 12.00 (s, 1H, OH), 8.13 (s, 1H, H$_{15}$), 8.06 (t, J=91 Hz, 1H, H$_4$), 7.51 (dd, J=3.2, 9.1 Hz, 1H, H$_5$), 1.93-1.08 (m, 11H, Cyhexyl); $^{13}$C NMR (100 MHz, DMSO-d6) δ (ppm) 157.42, *154.77 (C3), 145.09, *145.02 (C15), 140.03, *139.92 (C2), 138.93, *138.88 (C6), 128.46, *128.41 (C5), 125.32, *125.13 (C4), 96.53 (C8), 80.55 (C7), 49.38, 25.01, 22.76 (Cyhexyl) (* doubling of the peaks were observed due to the coupling of carbons with fluorine atom); $^{19}$F NMR (400 MHz, DMSO-d6) δ (ppm) -121.43; HRMS (ESI$^+$) m/z calcd for C$_{14}$H$_{17}$F$_1$N$_3$O$_1^+$ 262.1387 found 262.1350.

g) 3-fluoro-6-(hex-5-en-1-yn-1-yl)picolinaldehyde oxime (Compound 3g)

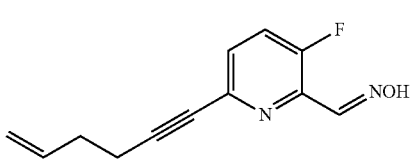

To a degassed solution of oxime 2 (136 mg, 0.624 mmol, 1 equiv) in THF/Et$_3$N (4 mL/2 mL), Pd[PPh$_3$]$_4$ (72 mg, 0.062 mmol, 0.1 equiv) and CuI (24 mg, 0.125 mmol, 0.2 equiv) were added. After degassing the reaction mixture for 5 min at room temperature, the alkyne 1g (1-hexene-5-yne, 50 mg, 0.624 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 3g as a white solid (110 mg, 81%). R$_f$ (20% EA+PE) 0.30; IR (neat) V$_{max}$ 3160, 3068, 2920, 2849, 2231, 1579, 1487, 1459, 1248, 1187, 1114, 982, 915, 842, 815, 700, 629, 525 cm$^{-1}$; H NMR (400 MHz, CDCl$_3$) δ (ppm) 9.30 (br s, 1H, OH), 8.31 (s, 1H, H$_{13}$), 7.41-7.31 (m, 2H, H$_4$, H$_5$), 5.88 (m, 1H, H$_{11}$), 5.07 (m, 1H, H$_{12}$), 2.50 (t, J=7.2 Hz, 1H, H$_9$), 2.37 (q, J=7.2 Hz, 1H, H$_{10}$), 1.88 (quintet, J=7.1, 7.5 Hz, 2H, H$_{10}$); $^{13}$C NMR (100 MHz, CDCl$_3$) δ (ppm) 158.08, *155.43 (C3), 146.09, *146.04 (C13), 140.03, *139.98 (C2), 139.53, *139.42 (C6), 136.53 (C11), 128.48, *128.39 (C5), 124.59, *124.39 (C4), 115.91 (C12), 90.66 (C7), 79.35 (C8), 32.31 (C10), 19.09 (C9) (* doubling of the peaks were observed due to the coupling of carbons with fluorine atom); $^{19}$F NMR (400 MHz, CDCl$_3$) δ (ppm) -122.20. HRMS (ESI$^+$) m/z calcd for C$_{12}$H$_{12}$F$_1$N$_2$O$_1^+$ 219.0951 found 219.0928.

h) 6-((4-ethylphenyl)ethynyl)-3-fluoropicolinaldehyde oxime (Compound 3h)

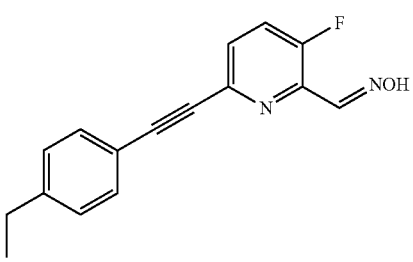

To a degassed solution of oxime 2 (84 mg, 0.384 mmol, 1 equiv) in THF/Et$_3$N (4 mL/2 mL), Pd[PPh$_3$]$_4$ (45 mg, 0.038 mmol, 0.1 equiv) and CuI (15 mg, 0.077 mmol, 0.2 equiv) were added. After degassing the reaction mixture for 5 min at room temperature, the alkyne 1h (4-ethylphenylacetylene, 50 mg, 0.384 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 15:85) to afford the desired coupled fluoro oxime 3h as a light yellowish solid (95 mg, 92%). R$_f$ (20% EA+PE) 0.45; IR (neat) v$_{max}$ 3284, 2963, 2928, 2216, 1578, 1510, 1456, 1270, 1242, 1196, 993, 936, 828, 722, 677, 625, 546, 496 cm$^{-1}$; H NMR (400 MHz, Acetone-d6) δ (ppm) 11.09 (br s, 1H, OH), 8.23 (s, 1H, H$_{17}$), 7.71 (dd, J=8.6, 9.7 Hz, 1H, H$_4$), 7.65 (dd, J=3.8, 8.6 Hz, 1H, H$_5$), 7.53 (d, J=8.1 Hz, 2H, H$_{10}$, H$_{14}$), 7.29 (d, J=8.1 Hz, 2H, H$_{11}$, H$_{13}$), 2.68 (q, J=7.4 Hz, 2H, H$_{15}$), 1.22 (q, J=7.4 Hz, 2H, H$_{16}$); $^{13}$C NMR (100 MHz, Acetone-d6) δ (ppm) 159.09, *156.43 (C3), 146.85, 146.76, 146.70 (C12, C17), 141.71, *141.56 (C2), 140.26, *140.21 (C6), 132.80 (C10, C14), 129.53, *129.45 (C5), 129.17 (C11, C13), 125.86, *125.66 (C4), 120.14 (C9), 89.51 (C7), 88.04 (C8), 29.44 (C15), 15.79 (C16) (* doubling of the peaks were observed due to the coupling of carbons with fluorine atom); $^{19}$F NMR (400 MHz, Acetone-d6) δ (ppm) −121.63; HRMS (ESI$^+$) m/z calcd for C$_{16}$H$_{14}$F$_1$N$_2$O$_1$$^+$ 269.1084 found 269.1085.

i) 6-(4-chlorobut-1-yn-1-yl)-3-fluoropicolinaldehyde oxime (Compound 3i)

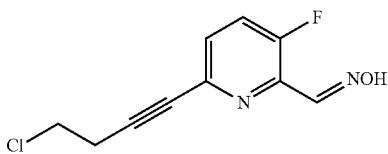

To a degassed solution of oxime 2 (123 mg, 0.565 mmol, 1 equiv) in THF/Et$_3$N (4 mL/2 mL), Pd[PPh$_3$]$_4$ (65 mg, 0.057 mmol, 0.1 equiv) and CuI (22 mg, 0.113 mmol, 0.2 equiv) were added. After degassing the reaction mixture for 5 min at room temperature, the alkyne ii (4-chloro-1-butyne, 50 mg, 0.565 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:3) to afford the desired coupled fluoro oxime 3i as a white solid (100 mg, 78%). R$_f$ (30% EA+PE) 0.45; IR (neat) v$_{max}$ 3271, 2245, 1579, 1455, 1293, 1240, 1178, 984, 940, 838, 726, 693, 658, 639, 535, 465 cm$^{-1}$; $^1$H NMR (400 MHz, CDCl$_3$) δ (ppm) 9.38 (br s, 1H, OH), 8.31 (s, 1H, H$_{13}$), 7.46-7.34 (m, 2H, H$_4$, H$_5$), 3.67 (t, J=7.2 Hz, 2H, H$_{10}$), 2.89 (t, J=7.2 Hz, 2H, H$_9$); $^{13}$C NMR (100 MHz, CDCl$_3$) δ (ppm) 158.30, *155.65 (C3), 145.77, 145.72 (C11), 139.72, *139.60 (C2), 139.38, *139.33 (C6), 128.72, *128.67 (C5), 124.69, *124.49 (C4), 86.62 (C8), 80.61 (C7), 41.49 (C9), 23.65 (C10) (* doubling of the peaks were observed due to coupling of carbons with fluorine atom); $^{19}$F NMR (400 MHz, CDCl$_3$) δ (ppm) −121.60. HRMS (ESI$^+$) m/z calcd for C$_{10}$H$_9$Cl$_1$F$_1$N$_2$O$_1$$^+$ 219.0951 found 219.0928.

j) 6-((3,6-dihydropyren-4-yl)ethynyl)-3-fluoropicolinaldehyde oxime (Compound 3j)

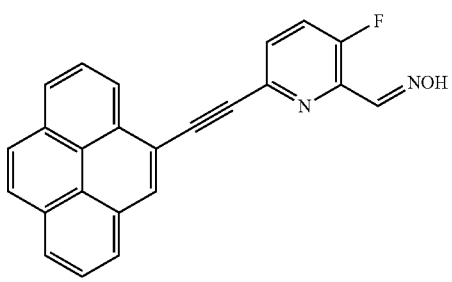

To a degassed solution of oxime 2 (53 mg, 0.240 mmol, 1.1 equiv) in THF/Et$_3$N (4 mL/2 mL), Pd[PPh$_3$]$_4$ (38 mg, 0.033 mmol, 0.15 equiv) and CuI (13 mg, 0.066 mmol, 0.3 equiv) were added. After degassing the reaction mixture for 5 min at room temperature, the alkyne 1j (1-ethynylpyren, 50 mg, 0.221 mmol, 1 equiv) was added dropwise and the reaction mixture was stirred at the room temperature for 16 h. After completion (checked by TLC), the reaction mixture was concentrated under reduced pressure and the residue was purified by column chromatography (pure EtOAc to MeOH/EtOAc 5:95) to afford the desired coupled fluoro oxime 3j as a light yellowish solid (60 mg, 81%). R$_f$ (20% EA+PE) 0.50; IR (neat) v$_{max}$ 3252, 3047, 2436, 2207, 1581, 1464, 1251, 1205, 1119, 997, 836, 713, 692, 677, 635, 609, 539, 459 cm$^{-1}$; $^1$H NMR (400 MHz, DMSO-d6) δ (ppm) 12.09 (s, 1H, OH), 8.62 (d, J=9.2 Hz, 1H, Ar), 8.44-8.23 (m, 8H, Ar), 8.16 (t, J=7.8 Hz, 1H, Ar), 7.99-7.91 (m, 2H, Ar) 7.71 (dd, J=3.8, 8.9 Hz, 1H), 7.53 (t, J=8.6 Hz, 1H); $^{13}$C NMR (100 MHz, DMSO-d6) δ (ppm) 157.86, *155.20 (C3), 145.10, *145.04 (C25), 140.60, *140.19 (C2), 138.49, *138.44 (C6), 131.56, 130.71, 130.42, 129.97, 129.21, 128.85, 127.21, 126.88, 126.28, 126.24, 125.60, 125.40, 124.99, 124.61, 123.55, 123.27, 115.33, (Ar), 93.40 (C7), 87.39 (C8) (* doubling of the peaks were observed due to the coupling of carbons with fluorine atom); $^{19}$F NMR (400 MHz, DMSO-d6) δ (ppm) −120.05; HRMS (ESI$^+$) m/z calcd for C$_{24}$H$_{14}$F$_1$N$_2$O$_1$$^+$ 365.1123 found 365.1085.

k) 4-(5-fluoro-6-((hydroxyimino)methyl)pyridin-2-yl)but-3-yne-1-sulfonamide (Compound 3k)

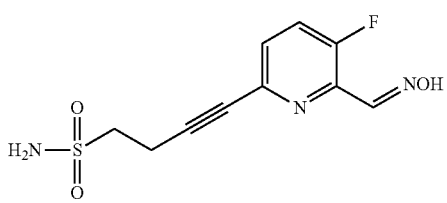

To a degassed solution of oxime 2 (82 mg, 0.375 mmol, 1 equiv) in THF/Et$_3$N (4 mL/2 mL), Pd[PPh$_3$]$_4$ (43 mg, 0.038 mmol, 0.1 equiv) and CuI (14 mg, 0.075 mmol, 0.2 equiv) were added. After degassing the reaction mixture for 5 min at room temperature, the alkyne 1k (but-3-yne-1-sulfonamide, 50 mg, 0.375 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 3:1) to afford the desired coupled fluoro oxime 3k as a light yellowish solid (55 mg, 54%). $R_f$ (80% EA+PE) 0.35; IR (neat) $v_{max}$ 3347, 3266, 3001, 2237, 1557, 1462, 1327, 1248, 1140, 983, 852, 716, 699, 642, 587, 492 cm$^{-1}$; $^1$H NMR (400 MHz, Acetone-d6) δ (ppm) 11.08 (br s, 1H, OH), 8.20 (s, 1H, H$_{11}$), 7.68 (t, J=8.8 Hz, 1H, H$_4$), 7.54 (dd, J=3.4, 8.8 Hz, 1H, H$_5$), 6.28 (2s, 3H, —NH$_2$), 3.41 (t, J=7.4 Hz, 2H, H$_{10}$), 3.29 (t, J=7.5 Hz, 2H, H$_{10}$), 2.99 (t, J=7.4 Hz, 2H, H$_9$), 2.83 (t, J=7.5 Hz, 2H, H$_9$) (* doubling of the alkyne moiety signals were observed due to the resolution); $^{13}$C NMR (100 MHz, Acetone-d6) δ (ppm) 159.08, *156.43 (C3), 146.61, *146.56, (C11), 141.44, *141.33 (C2), 140.10, *140.05 (C6), 129.45, *129.40 (C5), 125.81, *125.61 (C4), 87.35, 81.34 (C8), 75.48, 67.05 (C7), 53.72, 53.48 (C10), 15.60, 15.53 (C9) (* doubling of the peaks were observed due to the coupling of carbons with fluorine atom); $^{19}$F NMR (400 MHz, Acetone-d6) δ (ppm) –121.98; HRMS (ESI$^+$) m/z calcd for C$_{10}$H$_{11}$F$_1$N$_{31}$S$_1^+$ 272.0481 found 275.0500.

l) tert-butyl (4-(5-fluoro-6-((hydroxyimino)methyl)pyridin-2-yl)but-3-yn-1-yl)carbam-ate (Compound 3l)

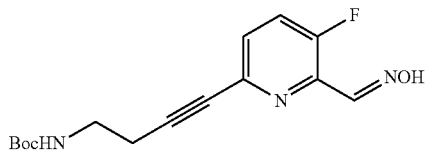

To a degassed solution of oxime 2 (64 mg, 0.295 mmol, 1 equiv) in THF/Et$_3$N (4 mL/2 mL), Pd[PPh$_3$]$_4$ (34 mg, 0.029 mmol, 0.1 equiv) and CuI (11 mg, 0.059 mmol, 0.2 equiv) were added. After degassing the reaction mixture for 5 min at room temperature, the alkyne 3l (4-(NHBoc)-1-butyne, 50 mg, 0.295 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 35:65) to afford the desired coupled fluoro oxime 4l as a light yellowish solid (50 mg, 55%). $R_f$ (50% EA+PE) 0.70; IR (neat) $v_{max}$ 3301, 2925, 2240, 1675, 1511, 1464, 1404, 1348, 1243, 1165, 1144, 987, 839, 788, 639, 577, 463 cm$^{-1}$; $^1$H NMR  (400 MHz, CDCl$_3$) δ (ppm) 11.20, 9.66 (2br s, 1.5H, OH), 8.32, 8.20 (2s, 1.5H, H$_{11}$), 7.44-7.23 (m, 3H, H$_4$, H$_5$), 6.78, 5.22 (2s, 1.5H, —NH), 3.38 (q, J=6.4 Hz, 3H, H$_{10}$), 2.61 (t, J=6.4 Hz, 3H, H$_9$), 1.48, 1.42 (2s, 13.5H, -Boc); $^{13}$C NMR  (100 MHz, CDCl$_3$) δ (ppm) 158.09, 157.51, 155.79, 155.46, 144.95, 144.56, 139.78, 139.67, 139.42, 139.33, 134.71, 129.90, 129.86, 128.47, 128.22, 125.33, 125.14, 124.62, 124.42 (Ar, —C=NOH), 88.59, *88.33 (C8), 80.65 (-Boc), *80.04, 79.66 (C7), *40.35, 39.13 (C10), 28.38 ((-Boc), *21.21, 20.97 (C9); $^{19}$F NMR (400 MHz, CDCl$_3$) δ (ppm) –122.01, –122.68; (rotameric mixture); HRMS (ESI$^+$) m/z calcd for C$_{15}$H$_{19}$F$_1$N$_3$O$_3^+$ 308.1383 found 308.1405.

m) 4-((5-fluoro-6-((hydroxyimino)methyl)pyridin-2-yl)ethynyl)benzonitrile (Compound 3m)

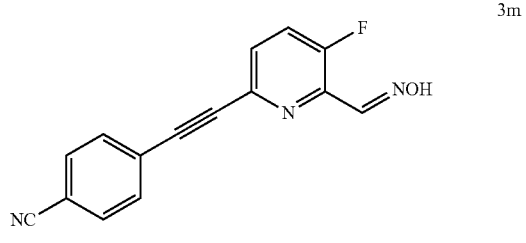

To a degassed solution of oxime 2 (86 mg, 0.393 mmol, 1 equiv) in THF/Et$_3$N (4 mL/2 mL), Pd[PPh$_3$]$_4$ (45 mg, 0.039 mmol, 0.1 equiv) and CuI (15 mg, 0.079 mmol, 0.2 equiv) were added. After degassing the reaction mixture for 5 min at room temperature, the alkyne 1m (4-ethynylbenzonitrile, 50 mg, 0.393 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:4) to afford the desired coupled fluoro oxime 3m as a light yellowish solid (30 mg, 29%). (20% EA+PE) 0.45; IR (neat) $v_{max}$ 3247, 2229, 1602, 1503, 1464, 1284, 1248, 1198, 994, 930, 838, 733, 673, 605, 556 cm$^{-1}$; $^1$H NMR (400 MHz, DMSO) δ (ppm) 12.08 (s, 1H, OH), 8.19 (s, 1H, H$_{16}$), 7.98-7.75 (m, 6H, Ar); $^{13}$C NMR (100 MHz, DMSO) δ (ppm) 158.04, *155.37 (C3), 144.95, *144.89 (C16), 140.72, *140.61 (C2), 137.53, *137.49 (C6), 132.70, 132.51 (C10, C11, C13, C14), 129.38, *129.33 (C5), 125.96 (C9), 125.65, *125.45 (C4), 118.28 (C15), 111.78 (C12), 91.04 (C7), 86.68 (C8) (* doubling of the peaks were observed due to the coupling of carbons with fluorine atom); $^{19}$F NMR (400 MHz, DMSO) δ (ppm) –119.12; HRMS (ESI$^+$) m/z calcd for C$_{15}$H$_9$F$_1$N$_3$O$_1^+$ 266.0689 found 266.0724.

n) 6-(5-(1,3-dioxoisoindolin-2-yl)pent-1-yn-1-yl)-3-fluoropicolinaldehyde oxime (Compound 3n)

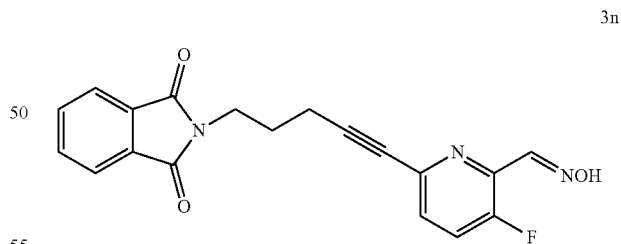

To a degassed solution of oxime 2 (102 mg, 0.469 mmol, 1 equiv) in THF/Et$_3$N (6 mL/3 mL), Pd[PPh$_3$]$_4$ (81 mg, 0.070 mmol, 0.15 equiv) and CuI (27 mg, 0.141 mmol, 0.3 equiv) were added. After degassing the reaction mixture for 5 min at room temperature, the alkyne 1n (N-(4-pentynyl)phthalimide, 100 mg, 0.469 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:1 to EtOAc/PE 6:4) to afford the desired coupled fluoro oxime 3n as a white solid (50 mg, 30%). $R_f$ (50% EA+PE) 0.55; IR (neat) $v_{max}$ 3320, 2941, 2233, 1771, 1762, 1689, 1580, 1460, 1399, 1245, 1184, 1019, 971, 883, 834, 723, 662, 529 cm$^{-1}$; $^1$H NMR (400 MHz, CDCl$_3$) δ (ppm) 9.26 (s, 1H, OH), 8.22 (s, 1H, H$_{15}$), 7.75 (dd, J=3.0, 5.5 Hz, 2H, H$_{16}$, H$_{17}$), 7.61 (dd, J=3.0, 5.5 Hz, 2H, H$_{15}$, H$_{18}$), 7.30 (t, J=8.7 Hz, 1H, H$_4$), 7.23 (dd, J=3.9, 8.7 Hz, 1H, H$_5$), 3.78 (t, J=6.9 Hz, 2H, H$_{11}$), 2.45 (t, J=6.9 Hz, 2H, H$_9$), 1.97 (quintet, J=6.9 Hz, 2H, H$_{10}$); $^{13}$C NMR (100 MHz, CDCl$_3$) δ (ppm) 168.35 (C13, C20), 158.03, *155.38 (C3), 146. 04, *145.99 (C21), 139.74, *139.70 (C2), 139.46, *139.35 (C6), 133.89 (C10, C11), 132.03 (C14, C19), 128.49, *128.44 (C5), 124.47, *124.27 (C4), 123.24 (C15, C18), 89.76 (C7), 79.81 (C8), 37.24 (C11), 26.89 (C10), 17.11 (C9) (* doubling of the peaks were observed due to the coupling of carbons with fluorine atom); $^{19}$F NMR (400 MHz, CDCl$_3$) δ (ppm) −122.10; HRMS (ESI$^+$) m/z calcd for C$_{19}$H$_{15}$F$_1$N$_3$O$_3^+$ 352.1096 found 352.1092.

o) 3-fluoro-6-((4-hydroxytetrahydro-2H-pyran-4-yl)ethynyl)picolinaldehyde oxime (Compound 3o)

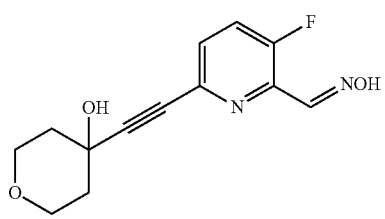

To a degassed solution of oxime 2 (86 mg, 0.396 mmol, 1 equiv) in THF/Et$_3$N (4 mL/2 mL), Pd[PPh$_3$]$_4$ (46 mg, 0.040 mmol, 0.10 equiv) and CuI (15 mg, 0.079 mmol, 0.2 equiv) were added. After degassing the reaction mixture for 5 min at room temperature, the alkyne 1o (4-ethynyltetrahydro-2H-pyran-4-ol, 50 mg, 0.396 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 3:1 to pure EtOAc) to afford the desired coupled fluoro oxime 3o as a light yellowish solid (90 mg, 86%). $R_f$ (50% EA+PE) 0.55; IR (neat) $v_{max}$ 3272, 3075, 2955, 2924, 2858, 1582, 1465, 1243, 1155, 1097, 1001, 982, 845, 727, 679, 637, 555, 475 cm$^{-1}$; $^1$H NMR (400 MHz, Acetone-d6) δ (ppm) 11.07 (br s, 1H, OH), 8.20 (s, 1H, H$_{15}$), 7.68 (dd, J=8.6, 9.6 Hz, 1H, H$_4$), 7.56 (dd, J=3.7, 8.6 Hz, 1H, H$_5$), 4.91 (brs, 1H, OH), 3.85, 3.65 (2m, 4H, H$_{11}$/H$_{13}$), 1.91, 1.81 (2m, 4H, H9/H$_{10}$); $^{13}$C NMR (100 MHz, Acetone-d6) δ (ppm) 159.14, *156.49 (C3), 146.57, *146.51, (C15), 141.56, *141.44 (C2), 139.88, *139.83 (C6), 129.56, *129.51 (C5), 125.81, *125.62 (C4), 93.28 (C8), 83.06 (C7), 65.88 (C9), 65.02 (C11, C13), 40.72 (C10, C14) (* doubling of the peaks were observed due to the coupling of carbons with fluorine atom); $^{19}$F NMR (400 MHz, Acetone-d6) δ (ppm) −121.77; HRMS (ESI$^+$) m/z calcd for O$_{13}$H$_{14}$F$_1$N$_2$O$_3^+$ 265.0974 found 265.0983.

p) 3-fluoro-6-((3-hydroxyoxetan-3-yl)ethynyl)picolinaldehyde oxime (Compound 3p)

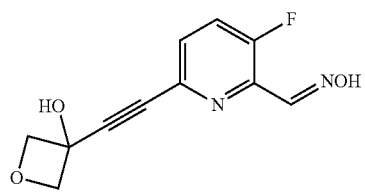

To a degassed solution of oxime 2 (111 mg, 0.51 mmol, 1 equiv) in THF/Et$_3$N (4 mL/2 mL), Pd[PPh$_3$]$_4$ (60 mg, 0.051 mmol, 0.1 equiv) and CuI (20 mg, 0.102 mmol, 0.2 equiv) were added. After degassing the reaction mixture for 5 min at room temperature, the alkyne 1p (3-ethynyloxetan-3-ol 50 mg, 0.51 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 4:1) to afford the desired coupled fluoro oxime 3p as a light yellowish solid (110 mg, 91%). $R_f$(Pure EA) 0.65; IR (neat) $v_{max}$ 3357, 3014, 1622, 1583, 1465, 1384, 1279, 1247, 1176, 1105, 986, 957, 899, 855, 676, 608, 568 cm$^{-1}$; $^1$H NMR (400 MHz, Acetone-d6) δ (ppm) 11.09 (br s, 1H, OH), 8.20 (s, 1H, H$_{13}$), 7.71 (t, J=8.6 Hz, 1H, H$_4$), 7.60 (dd, J=3.5, 8.8 Hz, 1H, H$_5$), 5.69 (s, 1H, —OH), 4.83, 4.69 (d, J=6.4 Hz, 4H, H$_{10}$, H$_{12}$); $^{13}$C NMR (100 MHz, Acetone-d6) δ (ppm) 159.33, *156.67 (C3), 146.55, *146.49, (C11), 141.76, *141.65 (C2), 139.41, *139.36 (C6), 129.45, *129.59 (C5), 125.92, *125.72 (C4), 89.67 (C8), 84.90, (C10, C12), 83.97 (C7), 67.54 (C9) (* doubling of the peaks were observed due to the coupling of carbons with fluorine atom); $^{19}$F NMR (400 MHz, Acetone-d6) δ (ppm) −121.22; HRMS (ESI$^+$) m/z calcd for C$_{10}$H$_{11}$F$_1$N$_3$O$_1$S$_1^+$ 272.0481 found 275.0500.

q) Benzyl 3-((5-fluoro-6-((hydroxyimino)methyl)pyridin-2-yl)ethynyl)azetidine-1-carb-oxylate (Compound 3q)

Benzyl 3-ethynylazetidine-1-carboxylate (Compound 1q)

1q

To a solution of amine (50 mg, 0.425 mmol, 1 equiv) in THF/Water (3 mL/1.5 mL) at 0° C., was added K$_2$CO$_3$ (117 mg, 0.850 mmol, 2 equiv) and benzyl chloroformate (773 μL, 0.51 mmol, 1.2 equiv). The ice bath was removed and the resulting mixture was allowed to warm to room temperature and stirred it for overnight. After completion (checked by TLC), the reaction mixture was concentrated under reduced pressure and the residue was purified by column chromatography (EtOAc/PE 1:9) to afford the protected compound 1q as a light yellowish solid (80 mg, 87%). $R_f$ (20% EA+PE) 0.55; IR (neat) $v_{max}$ 3290, 2962, 2891, 1701, 1449, 1413, 1355, 1293, 1123, 1027, 767, 696, 643, 606, 562, 497, 469 cm$^{-1}$; $^1$H NMR (300 MHz, CDCl$_3$) δ (ppm) 7.37-7.29 (m, 5H, phenyl), 5.08 (s, 1H, —CH$_2$Ph), 4.21 (t, J=8.6 Hz, 2H), 4.01 (dd, J=6.3, 8.3 Hz, 2H) 3.34 (m, 1H), 2.28 (d, J=2.5 Hz); $^{13}$C NMR (75 MHz, CDCl$_3$) δ (ppm) 156.08, 136.45, 128.48, 128.09, 128.01 (Ar), 83.59, 71.88, 66.77, 55.36, 19.49.

Benzyl 3-((5-fluoro-6-((hydroxyimino)methyl)pyridin-2-yl)ethynyl)azetidine-1-carb-oxylate (Compound 3q)

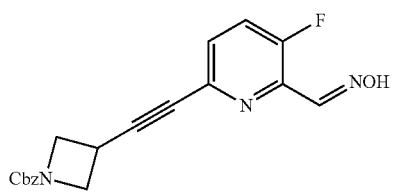

3q

To a degassed solution of oxime 2 (61 mg, 0.279 mmol, 1 equiv) in THF/Et$_3$N (4 mL/2 mL), Pd[PPh$_3$]$_4$ (32 mg, 0.028 mmol, 0.1 equiv) and CuI (11 mg, 0.056 mmol, 0.2 equiv) were added. After degassing the reaction mixture for 5 min at room temperature, the alkyne 1q (50 mg, 0.279 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:3) to afford the desired coupled fluoro oxime 3q as a light yellowish solid (75 mg, 76%). R$_f$ (40% EA+PE) 0.30; IR (neat) v$_{max}$ 3272, 2958, 2924, 2239, 1704, 1682, 1583, 1460, 1419, 1358, 1246, 1128, 978, 837, 733, 697, 633, 606, 562 cm$^{-1}$; $^1$H NMR  (400 MHz, CDCl$_3$) δ (ppm) 9.38 (s, 1H, OH), 8.31, (s, 1H, H$_{13}$), 7.44-7.26 (m, 7H, Ar), 5.09 (s, 2H, —CH$_2$Bn), 4.27 (t, J=8.5 Hz, 2H, H$_{10}$/H$_{12}$), 4.13 (dd, J=6.4, 8.5 Hz, 2H, H$_{10}$/H$_{12}$), 3.59 (m, 1H, H$_9$); $^{13}$C NMR  (100 MHz, CDCl$_3$) δ (ppm) 158.31, 155.65 155.81, 153.17, 145.52, 145.48, 139.95, 139.84, 139.03, 136.33, 136.27, 135.67, 129.89, 129.84, 128.46, 128.01, 128.05, 128.02, 125.42, 125.23, 124.69, 124.45 (Ar), 91.40, 89.34 (C8), 81.93, 80.67 (C7), 66.93, 66.85 (—CH$_2$Bn), 55.19 (C10/C12), 20.08, 19.99 (C9); $^{19}$F NMR (400 MHz, CDCl$_3$) δ (ppm) −121.42, −122.16; ( rotamers); HRMS (ESI$^+$) m/z calcd for C$_{19}$H$_{17}$F$_1$N$_3$O$_3$$^+$ 354.1258 found 354.1248.

r) 3-fluoro-6-(pyridin-3-ylethynyl)picolinaldehyde oxime (Compound 3r)

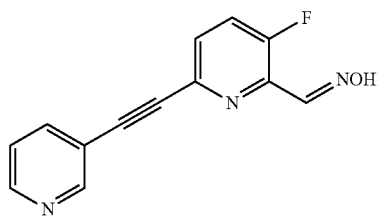

3r

To a degassed solution of oxime 2 (133 mg, 0.611 mmol, 1.05 equiv) in THF/Et$_3$N (4 mL/2 mL), Pd[PPh$_3$]$_4$ (101 mg, 0.087 mmol, 0.15 equiv) and CuI (33 mg, 0.174 mmol, 0.3 equiv) were added. After degassing the reaction mixture for 5 min at room temperature, the alkyne 1r (4-ethynylpyridine, 60 mg, 0.582 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 45:55) to afford the desired coupled fluoro oxime 3r as a white solid (110 mg, 79%). R$_f$ (60% EA+PE) 0.25; IR (neat) v$_{max}$ 3071, 2287, 2126, 1596, 1572, 1482, 1456, 1247, 1201, 1110, 995, 837, 799, 697, 636, 529 cm$^{-1}$; $^1$H NMR (400 MHz, DMSO-d6) δ (ppm) 12.07 (s, 1H, OH), 8.82 (br d, J=1.8 Hz, 1H, H$_{14}$), 8.65 (dd, J=1.5, 4.9 Hz, 1H, H$_{12}$), 8.19 (s, 1H, H$_{15}$), 8.06 (dt, J=1.8, 7.9 Hz, 1H, H$_{10}$), 7.90 (dd, J=8.6, 10.4 Hz, 1H, H$_4$), 7.78 (dd, J=3.7, 8.6 Hz, 1H, H$_5$), 7.50 (m, 1H, H$_{11}$); $^{13}$C NMR (100 MHz, DMSO-d6) δ (ppm) 157.68, *155.55 (C3), 151.92 (C12), 149.74 (C14), 144.99, *144.94 (C15), 140.62, *140.53 (C2), 139.02 (C10), 137.77, *137.73 (C6), 129.14, *129.10 (C5), 125.62, *125.46 (C4), 123.74 (C11), 118.33 (C9), 90.34 (C7), 85.20 (C8) (* doubling of the peaks were observed due to the coupling of carbons with fluorine atom); $^{19}$F NMR (400 MHz, DMSO-d6) δ (ppm) −119.52; HRMS (ESI$^+$) m/z calcd for C$_{13}$H$_9$F$_1$N$_3$O$_1$$^+$ 242.0749 found 242.0724.

s) Benzyl (3-(5-fluoro-6-((hydroxyimino)methyl)pyridin-2-yl)prop-2-yn-1-yl)(pyridin-4-yl)carbamate (Compound 3s)

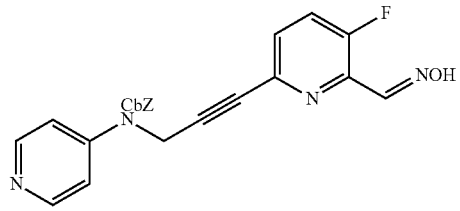

3s

To a degassed solution of oxime 2 (65 mg, 0.30 mmol, 1 equiv) in THF/Et$_3$N (4 mL/2 mL), Pd[PPh$_3$]$_4$ (35 mg, 0.03 mmol, 0.1 equiv) and CuI (11 mg, 0.06 mmol, 0.2 equiv) were added. After degassing the reaction mixture for 5 min at room temperature, the alkyne 1s (80 mg, 0.30 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:3) to afford the desired coupled fluoro oxime 3s as a light yellowish solid (75 mg, 62%). R$_f$(Pure EA) 0.38; IR (neat) v$_{max}$ 2922, 1730, 1595, 1496, 1463, 1389, 1359, 1214, 1146, 1051, 973, 845, 821, 734, 693, 633, 544, 477 cm$^{-1}$; $^1$H NMR  (400 MHz, Acetone-d6) δ (ppm) 11.29 (br s, 1H, OH), 8.56 (br d, J=3.6 Hz, 2H, H$_{13}$, H$_{15}$), 8.18 (s, 1H, H$_{17}$), 7.64-7.42 (m, 9H, Ar), 5.31 (s, 2H, —Cbz), 4.90 (s, 2H, H$_9$) ( more number of peaks observed in aromatic region due to rotamers); **$^{13}$C NMR (100 MHz, Acetone-d6) δ (ppm) 159.31, 156.66, 154.52, 151.38, 149.65, 146.54, 146.47, 141.80, 141.68, 139.36, 139.31, 137.24, 135.07, 135.02, 134.0, 132.80, 132.71, 129.60, 129.57, 129.45, 129.08, 128.85, 128.65, 119.37 (Ar, —C=NOH), 85.31 (C7), 83.39 (C8), 68.87 (-Cbz), 39.86 (C9) (* doubling of the peaks were observed due to the coupling of carbons with fluorine atom and also due to **rotameric nature); $^{19}$F NMR (400 MHz, Acetone-d6) δ (ppm) −121.06; HRMS (ESI$^+$) m/z calcd for $C_{22}H_{18}F_1N_4O_3^+$ 405.1341 found 405.1357.

t) Methyl(S)-2-((tert-butoxycarbonyl)amino)-5-(5-fluoro-6-((hydroxyimino)methyl)pyri-din-2-yl)pent-4-ynoate (Compound 3t)

Methyl (S)-2-((tert-butoxycarbonyl)amino)pent-4-ynoate (Compound 1t)

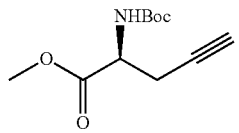

1t

To a solution of amino ester (190 mg, 1.495 mmol, 1 equiv) in DCM (15 mL) at RT (room temperature), was added TEA (625 µL, 4.485 mmol, 3 equiv) and Boc-anhydride (652 mg, 2.99 mmol, 2 equiv). The resulting mixture was stirred for overnight at RT. After completion (checked by TLC), the reaction mixture was concentrated under reduced pressure and the residue was purified by column chromatography (EtOAc/PE 1:9) to afford the protected compound it as a light yellowish solid (80 mg, 87%). $R_f$ (20% EA+PE) 0.65; IR (neat) $v_{max}$ 3294, 2979, 1746, 1709, 1501, 1366, 1355, 1249, 1158, 1061, 1025, 868, 779, 759, 643 cm$^{-1}$; $^1$H NMR (300 MHz, CDCl$_3$) δ (ppm) 5.32 (br d, J=7.3 Hz, 1H, —NH), 4.44 (m, 1H, H$_4$), 3.75 (s, 3H, —CH$_3$), 2.01 (t, J=2.6 Hz, 1H, H$_1$), 1.42 (s, 9H, -Boc); $^{13}$C NMR (75 MHz, CDCl$_3$) δ (ppm) 171.09 (—CO), 155.04 (-Boc), 80.17 (-Boc), 78.48 (C2), 71.57 (C1), 52.61 (C4), 51.88 (C7), 28.25 (-Boc), 22.51 (C3).

Methyl (S)-2-((tert-butoxycarbonyl)amino)-5-(5-fluoro-6-((hydroxyimino)methyl)pyri-din-2-yl)pent-4-ynoate (Compound 3t)

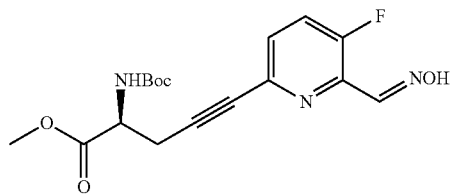

3t

To a degassed solution of oxime 2 (67 mg, 0.308 mmol, 1 equiv) in THF/Et$_3$N (4 mL/2 mL), Pd[PPh$_3$]$_4$ (36 mg, 0.031 mmol, 0.1 equiv) and CuI (12 mg, 0.062 mmol, 0.2 equiv) were added. After degassing the reaction mixture for 5 min at room temperature, the alkyne it (N-(Boc)-L-propargylglycine methyl ester, 70 mg, 0.308 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 3:7) to afford the desired coupled fluoro oxime 3t as a light yellowish solid (75 mg, 76%). $R_f$ (30% EA+PE) 0.25; IR (neat) $v_{max}$ 3331, 2978, 2928, 2242, 1744, 1693, 1504, 1462, 1366, 1247, 1159, 1059, 978, 841, 735, 645, 575 cm$^{-1}$; $^1$H NMR  (400 MHz, CDCl$_3$) δ (ppm) 9.55 (br s, 1H, OH), 8.31, (s, 1H, H$_{14}$), 7.41-7.31 (m, 2H, H$_4$, H$_5$), 5.56 (br d, J=8.2 Hz, 1H, —NH), 4.57 (m, 1H, H$_{10}$), 3.77 (s, 3H, H$_{13}$), 2.96 (m, 2H, H$_9$), 1.42 (s, 9H, -Boc); $^{13}$C NMR  (100 MHz, CDCl$_3$) δ (ppm) 171.13 (C11), 158.23, *155.75 (C3), 155.13 (-Boc), 145.10, *145.06 (C14), 139.83, *139.72 (C2), 139.18, *139.14 (C6), 128.76, *128.72 (C5), 124.59, *124.39 (C4), 85.19 (C8), 81.59 (-Boc), 80.32 (C7), 52.74 (C10), 51.97 (C13), 28.26 (-Boc), 23.76 (C9) (* doubling of the peaks were observed due to the coupling of carbons with fluorine atom); $^{19}$F NMR (400 MHz, CDCl$_3$) δ (ppm) −121.42, −122.16; ( rotamers); HRMS (ESI$^+$) m/z calcd for $C_{17}H_{21}F_1N_3O_5^+$ 366.1449 found 366.1460.

u) N-(9-((3aR,4R,6R,6aR)-6-(((3-(5-fluoro-6-((hydroxyimino)methyl)pyridin-2-yl)prop-2-yn-1-yl)oxy)methyl)-2,2-dimethyltetrahydrofuro[3,4-d][1,3]dioxol-4-yl)-9H-purin-6-yl)benzamide (Compound 3u)

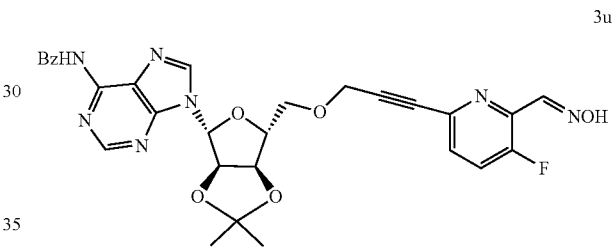

3u

To a degassed solution of oxime 2 (107 mg, 0.490 mmol, 1.1 equiv) in THF/Et$_3$N (6 mL/3 mL), Pd[PPh$_3$]$_4$ (85 mg, 0.074 mmol, 0.15 equiv) and CuI (25 mg, 0.134 mmol, 0.30 equiv) were added. After degassing the reaction mixture for 5 min at room temperature, the alkyne 1u (200 mg, 0.445 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 7:3) to afford the desired coupled fluoro oxime 3u as a light yellowish solid (160 mg, 61%). $R_f$(Pure EA) 0.38; IR (neat) $v_{max}$ 3201, 2926, 1698, 1611, 1582, 1457, 1357, 1246, 1211, 1074, 845, 797, 709, 644, 623, 541 cm$^{-1}$; $^1$H NMR ** (400 MHz, Acetone-d6) δ (ppm) 8.73, 8.60, 8.19 (3s, 3H, Ar, —C=NOH), 8.13 (m, 2H, Ar), 7.66-7.52 (m, 5H, Ar), 6.36 (d, J=2.3 Hz, 1H, —CH), 5.52 (dd, J=2.3, 6.1 Hz, 1H, —CH), 5.16 (dd, J=2.5, 6.1 Hz, 1H, —CH), 4.55-43-0.39 (m, 3H, —CH, —CH$_2$), 3.90 (dd, J=4.5, 10.3 Hz, 1H, —CH$_2$), 3.82 (dd, J=4.5, 10.3 Hz, 1H, —CH$_2$), 1.59 (s, 3H, —CH$_3$), 1.38 (s, 3H, —CH$_3$); $^{13}$C NMR (100 MHz, Acetone-d6) δ (ppm) 166.43, *159.26, 156.61, 152.87, 151.17, 146.04, *145.98, 143.67, 141.60, *141.50, 139.43, *139.38, 135.05, 133.38, 132.81, 132.72, 129.92, *129.87, 129.57, 129.50, 129.27, *125.85, 125.65 (Ar), 114.48 (—C—), 91.82 (—CH), 86.89 (—CH), 85.66 (—C), 85.55 (—CH), 85.42 (—C), 83.1 (—CH), 71.06 (—CH$_2$), 59.46 (—CH$_2$), 27.57 (—CH$_3$), 25.59 (—CH$_3$) (* doubling of the peaks were observed due to the coupling of carbons with fluorine atom and also due to **rotameric nature); $^{19}$F NMR (400 MHz, Acetone-d6) δ (ppm) −121.06; HRMS (ESI⁺) m/z calcd for $C_{15}H_{19}F_1N_3O_3^+$ 308.1383 found 308.1405.

v) (3aS,4S,6R,6aR)-6-(6-amino-9H-purin-9-yl)-N-(4-(5-fluoro-6-((Z)-(hydroxyimino)me-thyl)pyridin-2-yl)but-3-yn-1-yl)-2,2-dimethyltetrahydrofuro[3,4-d][1,3]dioxole-4-carboxamide 3v

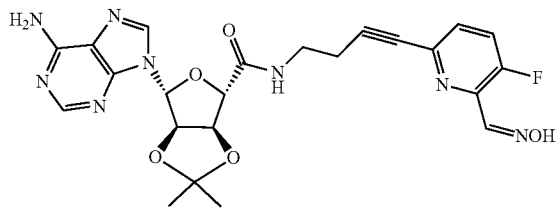

3v

To a degassed solution of oxime 2 (65 mg, 0.296 mmol, 1.1 equiv) in THF/Et₃N (6 mL/2 mL), Pd[PPh₃]₄ (47 mg, 0.040 mmol, 0.15 equiv) and CuI (15 mg, 0.080 mmol, 0.3 equiv) were added. After degassing the reaction mixture for 5 min at room temperature, the alkyne 1v (100 mg, 0.269 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:3) to afford the desired coupled fluoro oxime 3v as a light yellowish solid (75 mg, 55%). $R_f$ (50% EA+PE) 0.70; ¹H NMR  (400 MHz, CD₃OD) δ (ppm) 8.16-8.04 (3s, 3H, Ar, —C═NOH), 7.45 (t, J=8.8, 1H, H₄), 7.23 (dd, J=3.3, 8.8 Hz, 1H, H₅), 6.24 (br d, J=1.2 Hz, 1H, —CH), 5.49 (dd, J=1.8, 6.0 Hz, 1H, —CH), 5.31 (dd, J=1.2, 6.0 Hz, 1H, —CH), 4.59 (d, J=1.8 Hz, 1H, —CH), 3.50 (m, 1H, —CH₂), 2.99 (m, 1H, —CH₂), 2.22 (m, 1H, —CH₂), 2.03 (m, 1H, —CH₂), 1.48 (s, 3H, —CH₃), 1.27 (s, 3H, —CH₃); ¹³C NMR  (100 MHz, CD₃OD) δ (ppm) 172.16, 159.60, 157.27, 156.96, 153.92, 150.32, 144.76, 142.54, 141.45, 141.33, 140.47, 130.03, 130.00, 126.34, 126.14, 120.54, 115.18 (Ar), *92.50 (C16), 88.99 (C8), 88.76 (C15), 85.42 (C14), 85.30 (C13), 80.97 (C7), 38.69 (C10), 27.29 (C28), 25.53 (C29), 20.42 (C9); ¹⁹F NMR (400 MHz, CDCl₃) δ (ppm) −122.54; ( rotamers); HRMS (ESI⁺) m/z calcd for $C_{23}H_{24}F_1N_8O_5^+$ 511.1882 found 511.1848.

w) 3-fluoro-6-(10-(5-fluoro-6-((hydroxyimino)methyl)pyridin-2-yl)deca-1,9-diyn-1-yl)picolinaldehyde oxime (Compound 3w)

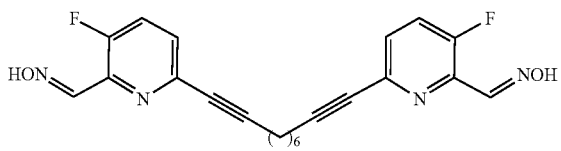

3w

To a degassed solution of oxime 2 (162 mg, 0.745 mmol, 2 equiv) in THF/Et₃N (4 mL/2 mL), Pd[PPh₃]₄ (86 mg, 0.075 mmol, 0.2 equiv) and CuI (28 mg, 0.149 mmol, 0.4 equiv) were added. After degassing the reaction mixture for 5 min at room temperature, the alkyne 1w (1,9-decadiyne, 50 mg, 0.373 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 4:6) to afford the desired coupled fluoro oxime 3w as a white solid (80 mg, 52%). $R_f$ (60% EA+PE) 0.20; IR (neat) $V_{max}$ 3273, 2940, 2859, 2232, 1580, 1464, 1239, 1183, 978, 943, 842, 714, 656, 566, 468 cm⁻¹; ¹H NMR (400 MHz, DMSO) δ (ppm) 11.97 (br s, 1H, OH), 8.12 (s, 1H, H₁₂, H₁₂′), 7.75 (dd, J=8.5, 10.3 Hz, 1H, H₄, H₄′), 7.50 (dd, J=3.7, 8.5 Hz, 1H, H₅, H₅′), 2.46 (t, J=6.9 Hz, 2H, H₉, H₉′), 1.58 (m, 2H, H₁₀, H₁₀′), 1.58 (m, 2H, H₁₁, H₁₁′); ¹³C NMR (100 MHz, DMSO) δ (ppm) 157.41, *154.77 (C3), 145.20, 145.13 (C12), 139.91, *139.88 (C2), 139.93, *139.89 (C6), 128.31, *128.26 (C5), 125.32, *125.12 (C4), 90.67 (C8), 79.46 (C7), 27.81 (C9), 27.65 (C10), 18.33 (C11) (* doubling of the peaks were observed due to the coupling of carbons with fluorine atom); ¹⁹F NMR (400 MHz, DMSO) δ (ppm) −121.33. HRMS (ESI⁺) m/z calcd for $C_{22}H_{21}F_2N_4O_2^+$ 411.1666 found 411.1627.

x) 6-(4-((7-chloro-2,3-dihydro-1H-cyclopenta[b]quinolin-9-yl)amino)but-1-yn-1-yl)-3-flu-oropicolin-aldehyde oxime (Compound 3λ)

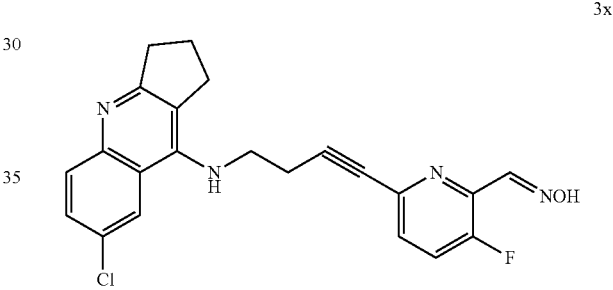

3x

To a degassed solution of oxime 2 (40 mg, 0.185 mmol, 1 equiv) in THF/Et₃N (4 mL/2 mL), Pd[PPh₃]₄ (21 mg, 0.019 mmol, 0.1 equiv) and CuI (7 mg, 0.037 mmol, 0.2 equiv) were added. After degassing the reaction mixture for 5 min at room temperature, the alkyne 1x (50 mg, 0.185 mmol, 1 equiv) was added dropwise and the reaction mixture was stirred at the room temperature for 16 h. After completion (checked by TLC), the reaction mixture was concentrated under reduced pressure and the residue was purified by column chromatography (pure EtOAc to MeOH/EtOAc 5:95) to afford the desired coupled fluoro oxime 3x as a white solid (70 mg, 93%). $R_f$ (10% MeOH+EA) 0.50; IR (neat) $v_{max}$ 3374, 2243, 1567, 1539, 1461, 1417, 1403, 1351, 1248, 1135, 1027, 997, 841, 820, 749, 691, 642, 546, 500, 461 cm⁻¹; ¹H NMR (400 MHz, DMSO) δ (ppm) 11.99 (br s, 1H, OH), 8.32 (s, 1H, H₂₀), 8.09 (s, 1H, H₂₅), 7.76 (dd, J=8.8, 10.0 Hz, 1H, H₄), 7.69 (d, J=8.8 Hz, 1H, H₂₁), 7.51 (dd, J=1.9, 8.8 Hz, 1H, H₂₃), 7.40 (dd, J=3.3, 8.8 Hz, 1H, H₅), 6.86 (t, J=6.6 Hz, 1H, —NH), 3.76 (q, J=6.8 Hz, 2H, H₁₀), 3.20 (t, J=7.2 Hz, 2H, H₁₆), 2.86 (t, J=7.6 Hz, 2H, H₁₄), 2.74 (t, J=6.8 Hz, 2H, H₉), 2.04 (m, 2H, H₁₅); ¹³C NMR (100 MHz, DMSO) δ (ppm) 168.75 (C17), 157.20, *155.09 (C3), 146.59 (C12), 145.21, 145.16 (C25), 140.04, *139.95 (C2), 138.60, *138.56 (C6), 130.36 (C22), 128.31, *128.27 (C5), 128.22 (C21), 127.85 (C19), 125.29, *125.13 (C4), 120.95 (C20, C23), 119.88 (C17), 113.52 (C13), 88.15 (C8), 80.49 (C7), 42.53 (C10), 34.14 (C11), 30.61 (C14), 22.73 (C15), 21.01 (C9) (* doubling of the peaks were observed due to the coupling of carbons with fluorine atom);

$^{19}$F NMR (400 MHz, DMSO) δ (ppm) −120.87; HRMS (ESI$^+$) m/z calcd for $C_{22}H_{19}Cl_1F_1N_4O_1^+$ 409.1242 found 409.1226.

y) 3-fluoro-6-(4-(quinolin-4-ylamino)but-1-yn-1-yl) picolinaldehyde oxime (Compound 3y)

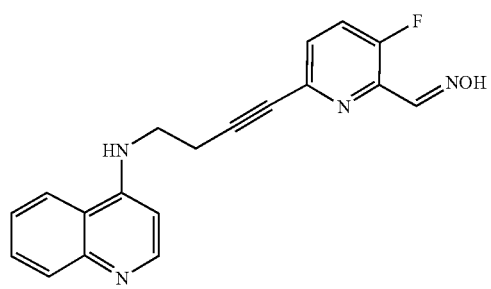

3y

To a degassed solution of oxime 2 (49 mg, 0.224 mmol, 1.1 equiv) in THF/Et$_3$N (4 mL/2 mL), Pd[PPh$_3$]$_4$ (35 mg, 0.031 mmol, 0.15 equiv) and CuI (12 mg, 0.061 mmol, 0.23 equiv) were added. After degassing the reaction mixture for 5 min at room temperature, the alkyne 1y (40 mg, 0.204 mmol, 1 equiv) was added dropwise and the reaction mixture was stirred at the room temperature for 16 h. After completion (checked by TLC), the reaction mixture was concentrated under reduced pressure and the residue was purified by column chromatography (pure EtOAc to MeOH/EtOAc 5:95) to afford the desired coupled fluoro oxime 3y as a yellowish solid (55 mg, 81%). R$_f$ (20% MeOH+EA) 0.30; IR (neat) v$_{max}$ 3335, 2922, 2239, 1584, 1451, 1402, 1343, 1244, 1119, 993, 835, 807, 759, 694, 675, 644, 572 cm$^{-1}$; $^1$H NMR (400 MHz, CD$_3$OD) δ (ppm) 8.39 (d, J=5.5 Hz, 1H, Ar), 8.23 (s, 1H, oxime), 8.13 (dd, J=0.9, 8.5 Hz, 1H, Ar), 7.82 (br d, J=8.5 Hz, 1H, Ar), 7.67-7.58 (m, 2H, Ar), 7.48-7.41 (m, 2H, Ar), 6.65 (d, J=5.5 Hz, 1H, Ar), 3.73 (t, J=6.9 Hz, 2H, H$_{10}$), 2.88 (t, J=6.9 Hz, 2H, H$_9$); $^{13}$C NMR (100 MHz, CD$_3$OD) δ (ppm) 152.61, 151.21, 148.88, 144.71, *144.69, 141.67, 141.58, 140.91, 140.87, 133.27, *133.19, 130.82, 130.18, *130.08, 130.03, *129.97, 128.81, 126.44, 126.28, 125.99, 122.43, 120.45 (Ar), 89.66 (C8), 81.27 (C7), 42.62 (C10), 20.08 (C9) (* doubling of the peaks were observed due to the coupling of carbons with fluorine atom); $^{19}$F NMR (400 MHz, CD$_3$OD) δ (ppm) −125.02; HRMS (ESI$^+$) m/z calcd for $C_{19}H_{16}F_1N_4O_1^+$ 335.1280 found 335.1303.

z) 6-(4-(1,2,3,4-tetrahydroacridin-9-ylamino)but-1-yn-1-yl)-3-fluoropicolinaldehyde oxime (Compound 3z)

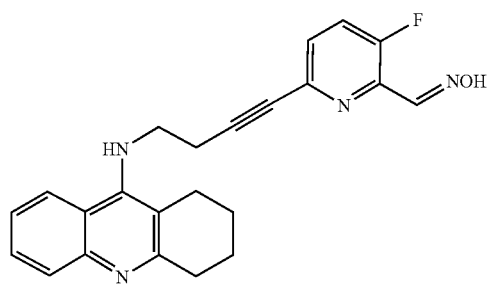

3z

To a degassed solution of oxime 2 (96 mg, 0.439 mmol, 1.1 equiv) in THF/Et$_3$N (6 mL/3 mL), Pd[PPh$_3$]$_4$ (69 mg, 0.060 mmol, 0.15 equiv) and CuI (23 mg, 0.12 mmol, 0.3 equiv) were added. After degassing the reaction mixture for 5 min at room temperature, the alkyne 1z (100 mg, 0.399 mmol, 1 equiv) was added dropwise and the reaction mixture was stirred at the room temperature for 16 h. After completion (checked by TLC), the reaction mixture was concentrated under reduced pressure and the residue was purified by column chromatography (pure EtOAc to MeOH/EtOAc 5:95) to afford the desired coupled fluoro oxime 3z as a yellowish solid (135 mg, 87%). R$_f$ (20% MeOH+EA) 0.35; IR (neat) v$_{max}$ 3063, 2925, 2854, 2237, 1640, 1581, 1456, 1245, 1178, 982, 831, 757, 695, 668, 635, 539 cm$^{-1}$; $^1$H NMR (400 MHz, CD$_3$OD) δ (ppm) 8.36 (s, 1H, oxime), 8.66-7.92 (m, 2H, Ar), 7.51 (m, Ar), 7.40-7.26 (m, 2H, Ar), 7.20 (dd, J=3.8, 8.6 Hz, 1H, Ar), 4.55 (br s, 1H, —NH), 3.72 (t, J=6.1 Hz, 2H, H$_{10}$), 3.05 (t, J=6.1 Hz, 2H, tacrine), 2.76 (t, J=6.1 Hz, 2H, H$_9$), 2.67 (t, J=6.3 Hz, 2H, tacrine), 1.85-1.76 (m, 4H, H$_{10}$, tacrine); $^{13}$C NMR (100 MHz, CD$_3$OD) δ (ppm) 158.18, 158.02, 155.52, 150.72, 144.71, 144.67, 140.59, 140.48, 139.06, 139.01, 132.13, 132.03, 131.92, 128.83, 128.65, 128.55, 128.42, 128.02, 127.98, 127.69, 124.49, 124.29, 124.22, 122.66, 120.17, 117.10 (Ar), 87.41 (C8), 81.42 (C7), 47.08 (C10), 21.93 (C9), 33.02, 24.82, 22.80, 22.39 (tacrine) (* doubling of the peaks were observed due to the coupling of carbons with fluorine atom and ** cis and trans mixture); $^{19}$F NMR (400 MHz, CD$_3$OD) δ (ppm) −125.02; HRMS (ESI$^+$) m/z calcd for $C_{23}H_{22}F_1N_4O_1^+$ 389.1755 found 389.1772.

B) With 6-bromo-3-fluoropicolinaldehyde oxime (Labelled) (Compound 4)

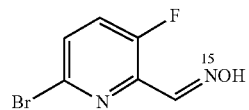

4

A solution of picolinaldehyde (204 mg, 1 mmol, 1 equiv), $^{15}$N labelled hydroxylamine hydrochloride (106 mg, 1.5 mmol, 1.5 equiv), and CH$_3$CO$_2$Na (246 mg, 3 mmol, 3 equiv) in dry ethanol (10 mL) was stirred at reflux during 16 h. After completion (checked by TLC), the reaction mixture was filtered through a small celite pad. The filtrate was concentrated under reduced pressure and the residue was purified by column chromatography (EtOAc/PE 1:9) to afford the oxime 4 as a white solid (230 mg, quant. yield). R$_f$ (20% EA+PE) 0.50; IR (neat) v$_{max}$ 3257, 2859, 1722, 1442, 1187, 1107, 968, 825, 727, 668, 619, 518 cm$^{-1}$; H NMR (400 MHz, CD$_3$OD) δ (ppm) 8.18 (d, J=2.5 Hz, 1H, H$_7$), 7.61-7.55 (m, 2H, H$_4$, H$_5$); $^{19}$F NMR (400 MHz, CDCl$_3$) δ (ppm) 127.91, 127.93.

3-fluoro-6-(5-phenylpent-1-yn-1-yl)picolinaldehyde oxime (compound 5)

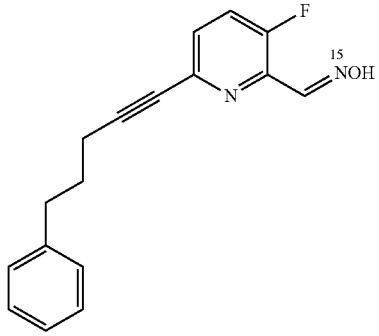

To a degassed solution of oxime 4 (78 mg, 0.364 mmol, 1.05 equiv) in THF/Et$_3$N (1 mL/3 mL), Pd[PPh$_3$]$_4$ (60 mg, 0.052 mmol, 0.15 equiv) and CuI (20 mg, 0.104 mmol, 0.3 equiv) were added. After degassing the reaction mixture for 5 min at room temperature, the alkyne 1a (5-phenyl-1-pentyne, 50 mg, 0.347 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 5 as a white solid (70 mg, 72%). R$_f$ (20% EA+PE) 0.40; IR (neat) v$_{max}$ 3177, 2933, 2876, 2226, 1568, 1445, 1159, 985, 807, 734, 703, 657, 638, 557, 490 cm$^{-1}$; $^1$H NMR (400 MHz, CDCl$_3$) δ (ppm) 9.49-8.90 (br s, 1H, OH), 8.26 (s, 1H, H$_{18}$), 7.39-7.08 (m, 7H, Ar), 2.71 (t, J=7.5 Hz, 2H, H$_{11}$), 2.37 (t, J=7.1 Hz, 2H, H$_9$), 1.88 (quintet, J=7.1, 7.5 Hz, 2H, H$_{10}$); $^{13}$C NMR (100 MHz, CDCl$_3$) δ (ppm) 158. 07, *155.42 (C3), 145.90, *145.86 (C18), 141.28 (C12), 140.09, *140.04 (C2), 139.54, *139.45 (C6), 128.50, 128.37, (C5, C13, C14, C16, C17), 125.95 (C15), 124.60, *124.40 (C4), 91.06 (C7), 79.44 (C8), 34.86 (C11), 29.72 (C10), 18.71 (C9); $^{19}$F NMR (400 MHz, CDCl$_3$) δ (ppm) −122.425, −122.453 (* doubling of the peaks were observed due to the coupling of carbons with fluorine atom); $^{19}$F NMR (400 MHz, CDCl$_3$) δ (ppm) 122.415; ESI MS$^+$ m/z for C$_{17}$H$_{17}$F$_1$N$_2$O$_1{}^+$ 284.1275.

6-bromo-3-fluoro-N'-hydroxypicolinimidamide (Compound 7)

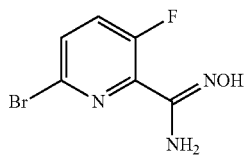

A solution of picolinonitrile 6 (compound purchased from Aldrich, see structure below) (100 mg, 0.498 mmol, 1 equiv), hydroxylamine hydrochloride (52 mg, 0.746 mmol, 1.5 equiv), and Na$_2$CO$_3$ (79 g, 0.746 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (pure EtOAc—MeOH/EtOAc 5:95) to afford the amidoxime 7 as a white solid (110 mg, 95%). R$_f$ (30% EA+PE) 0.35; IR (neat) v$_{max}$ 3473, 3369, 3057, 2923, 1665, 1563, 1450, 1239, 1112, 952, 835, 768, 756, 657, 551 cm$^{-1}$; $^1$H NMR (400 MHz, DMSO-d6) δ (ppm) 10.27 (s, 1H, —OH), 7.82-7.70 (m, 2H, H$_4$, H$_5$), 5.80 (s, 2H, —NH$_2$); $^{13}$C NMR (100 MHz, DMSO-d6) δ (ppm) 157.98, *155.36 (C3), 147.29, *147.20 (C7), 139.41, *139.26 (C2), 133.67, *133.65 (C6), 129.63, *129.57 (C5), 128.93, *128.71 (C4) (* doubling of the peaks were observed due to the coupling of carbons with fluorine atom); $^{19}$F NMR (400 MHz, DMSO-d6) δ (ppm) −199.96; HRMS (ESI$^+$) m/z calcd for C$_6$H$_6$Br$_1$F$_1$N$_3$O$_1{}^+$ 233.9660 found 233.9673.

Picolinonitrile 6 is as follows:

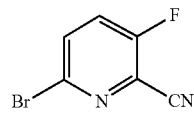

(E)-6-bromo-3-fluoro-N'-hydroxypicolinimidamide (Labelled) (Compound 8)

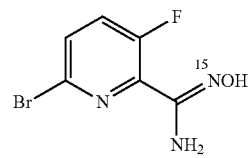

A solution of picolinonitrile 6 (purchased from Aldrich) (100 mg, 0.498 mmol, 1 equiv), $^{15}$N labelled hydroxylamine hydrochloride (52 mg, 0.746 mmol, 1.5 equiv), and Na$_2$CO$_3$ (79 g, 0.746 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (pure EtOAc—MeOH/EtOAc 5:95) to afford the amidoxime 8 as a light yellowish solid (115 mg, quant. yield). R$_f$ (30% EA+PE) 0.35; IR (neat) v$_{max}$ 3473, 3369, 3059, 2925, 1651, 1561, 1450, 1238, 1110, 935, 833, 764, 753, 656, 621, 552 cm$^{-1}$; $^1$H NMR (400 MHz, DMSO-d6) δ (ppm) 10.26 (s, 1H, —OH), 7.82-7.68 (m, 2H, H$_4$, H$_5$), 5.80 (s, 2H, —NH$_2$); $^{13}$C NMR (100 MHz, DMSO-d6) δ (ppm) 157.99, *155.36 (C3), 147.27, *147.18 (C7), 139.46, *139.35 (C2), 133.68, *133.65 (C6), 129.63, *129.58 (C5), 128.93, *128.71 (C4) (* doubling of the peaks were observed due to the coupling of carbons with fluorine atom); $^{19}$F NMR (400 MHz, DMSO-d6) δ (ppm) −199.98; ESI$^+$ m/z for C$_6$H$_6$Br$_1$F$_1$N$_3$O$_1$ is 233.9660.

3-fluoro-6-(5-phenylpent-1-yn-1-yl)picolinonitrile 9

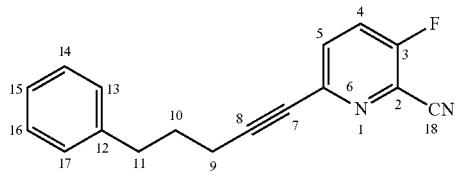 [SMILES: N#Cc1nc(C#CCCCc2ccccc2)ccc1F]

To a degassed solution of picolinonitrile 6 (153 mg, 0.763 mmol, 1.1 equiv) in THF/Et$_3$N (8 mL/3 mL), Pd[PPh$_3$]$_4$ (120 mg, 0.104 mmol, 0.15 equiv) and CuI (40 mg, 0.208 mmol, 0.3 equiv) were added. After degassing the reaction mixture for 5 min at room temperature, the alkyne 1a (100 mg, 0.693 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 95:5) to afford the desired coupled picolinonitrile 9 as a yellowish liquid (170 mg, 93%). R$_f$ (10% EtOAc+PE) 0.40; IR (neat) v$_{max}$ 2934, 2232, 1571, 1461, 1257, 1107, 841, 745, 699, 656, 606, 534, 487 cm$^{-1}$; $^1$H NMR (400 MHz, CDCl$_3$) δ (ppm) 7.58 (dd, J=4.2, 8.9 Hz, 1H), 7.51 (dd, J=7.7, 8.9 Hz, 1H), 7.33-7.12 (m, 5H), 2.76 (t, J=7.5 Hz, 2H), 2.44 (t, J=7.1 Hz, 2H), 1.95 (quintet, J=7.1, 7.5 Hz, 2H); $^{13}$C NMR (100 MHz, CDCl$_3$) δ (ppm) 161.27, *158.57, 141.53, *141.48, 141.01, 131.97, *131.92, 128.44, 128.39, 126.02, 125.05, *124.89, 122.66, *122.45, 112.36, *112.31, 93.19, 78.45, 34.80 29.51, 18.62 (* doubling of the peaks were observed due to the coupling of carbons with fluorine atom); $^{19}$F NMR (400 MHz, CDCl$_3$) δ (ppm) -116.14; HRMS (ESI$^+$) m/z calcd for C$_{17}$H$_{13}$F$_1$N$_2$Na$_1^+$ 287.0949 found 287.0955.

3-fluoro-N'-hydroxy-6-(5-phenylpent-1-yn-1-yl)picolinimidamide (Compound 10)

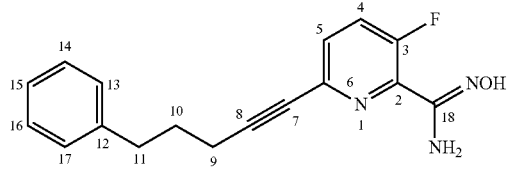

To a degassed solution of amidoxime 7 (36 mg, 0.15 mmol, 1.1 equiv) in THF/Et$_3$N (4 mL/2 mL), Pd[PPh$_3$]$_4$ (24 mg, 0.021 mmol, 0.15 equiv) and CuI (8 mg, 0.042 mmol, 0.3 equiv) were added. After degassing the reaction mixture for 5 min at room temperature, the alkyne 1a (5-phenyl-1-pentyne, 20 mg, 0.14 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 7:3—pure EtOAc) to afford the desired coupled fluoro amidoxime 10 as a light yellowish solid (32 mg, 78%). R$_f$ (50% EA+PE) 0.65; IR (neat) v$_{max}$ 3490, 3381, 3144, 2926, 2235, 1667, 1561, 1470, 1240, 938, 963, 838, 745, 699, 683, 646, 599, 493 cm$^{-1}$; $^1$H NMR (400 MHz, Acetone-d6) δ (ppm) 9.51 (br s, 1H, OH), 7.63 (dd, J=8.5, 10.5 Hz, 1H, H$_4$), 7.53 (dd, J=3.5, 8.5 Hz, 1H, H$_5$), 7.35-7.15 (m, 5H, Ar), 5.72 (s, 2H, —NH$_2$), 2.80 (t, J=7.5 Hz, 2H, H$_{11}$), 2.47 (t, J=7.1 Hz, 2H, H$_9$), 1.94 (quintet, J=7.1, 7.5 Hz, 2H, H$_{10}$); $^{13}$C NMR (100 MHz, CDCl$_3$) δ (ppm) 157.77, *155.09 (C3), 148.56, *148.46 (C18), 141.53 (C12), 138.43, *138.36 (C2), 138.29, *138.19 (C6), 128.48, 128.35 (C5, C13, C14, C16, C17), 125.90 (C15), 125.51, *125.30 (C4), 89.96 (C7), 79.79 (C8), 34.55 (C11), 30.03 (C10), 18.10 (C9) (* doubling of the peaks were observed due to the coupling of carbons with fluorine atom); $^{19}$F NMR (400 MHz, CDCl$_3$) δ (ppm) -116.95; HRMS (ESI$^+$) m/z calcd for C$_{17}$H$_{16}$F$_1$N$_3$O$_1$Na$_1^+$ 320.1160 found 320.1170.

C) With hydroxamic acid 11 (Compound 11)

Hydroxamic acid (compound 11) was purchased from Aldrich:

3-fluoro-N-hydroxy-6-(5-phenylpent-1-yn-1-yl)picolinamide (Compound 12)

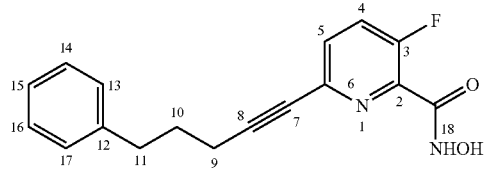

To a degassed solution of hydroxamic acid 11 (108 mg, 0.458 mmol, 1.1 equiv) in THF/Et$_3$N (4 mL/2 mL), Pd[PPh$_3$]$_4$ (72 mg, 0.062 mmol, 0.15 equiv) and CuI (24 mg, 0.125 mmol, 0.3 equiv) were added. After degassing the reaction mixture for 5 min at room temperature, the alkyne 1a (5-phenyl-1-pentyne, 60 mg, 0.416 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:1) to afford the desired coupled fluoro amidoxime 12 as a yellowish solid (32 mg, 25%). R$_f$ (50% EA+PE) 0.65; IR (neat) v$_{max}$ 3264, 2923, 2856, 2231, 1689, 1651, 1455, 1247, 1027, 837, 745, 698, 651, 541 cm$^{-1}$; $^1$H NMR (400 MHz, CDCl$_3$) δ (ppm)) 7.50-7.41 (m, 2H, Ar), 7.31-7.26 (m, 2H, Ar), 7.22-7.16 (m, 3H, Ar), 2.76 (t, J=7.5 Hz, 2H, H$_{11}$), 2.43 (t, J=7.1 Hz, 2H, H$_9$), 1.94 (quintet, J=7.1, 7.5 Hz, 2H, H$_{10}$); $^{13}$C NMR (100 MHz, CDCl$_3$) δ (ppm) 159.70 (C18), 158.67, *156.49 (C3), 141.11 (C15), 138.75, *135.74 (C6), 132.13, *132.06 (C2), 131.96, *131.61 (C5), 128.49 (C14, C16), 128.44 (C13, C17), 126.67, *126.53 (C4), 126.07 (C12), 91.82 (C7), 79.03 (C8), 34.87 (C11), 29.67 (C10), 18.65 (C9) (* doubling of the peaks were observed due to the coupling of carbons with fluorine atom); $^{19}$F NMR (400 MHz, CDCl$_3$) δ (ppm) -116.62; HRMS (ESI$^+$) m/z calcd for C$_{17}$H$_{16}$F$_1$N$_2$O$_2^+$ 299.1177 found 299.1190.

III—Experimental Procedures for Hydrogenations

3-fluoro-6-(5-phenylpentyl)picolinaldehyde oxime (Compound 13)

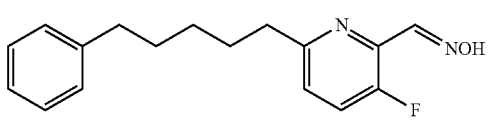

To a degassed solution of fluorooxime 3a (50 mg, 0.177 mmol, 1 equiv) in dry EtOAc (3 mL), 10% Pd/C (4.7 mg, 0.0178 mmol, 0.25 equiv) was added. After flushing with $H_2$ three times, the reaction mixture was stirred at room temperature under $H_2$ (1 atm.) for 90 min. Upon completion (monitored by TLC), the catalyst was removed by filtration through a short column of celite, the solvent was evaporated, and the residue was purified by column chromatography (EtOAc/PE 1:9) to afford oxime 13 as a white solid (50 mg, 99%); $R_f$ (20% EA+PE) 0.50; IR (neat) $v_{max}$ 3281, 3026, 2929, 2856, 1603, 1468, 1454, 1247, 1112, 980, 834, 745, 698, 642, 543, 499 cm$^{-1}$; $^1$H NMR (400 MHz, CDCl$_3$) δ (ppm) 9.94 (br s, 1H, OH), 8.30 (s, 1H), 7.31-6.98 (m, 7H), 2.72 (t, J=7.7 Hz, 2H), 2.52 (t, J=7.7 Hz, 2H), 1.67 (quintet, J=7.7 Hz, 2H), 1.58 (quintet, J=7.7 Hz, 2H); 1.31 (quintet, J=7.3, 7.9 Hz, 2H); $^{13}$C NMR (100 MHz, CDCl$_3$) δ (ppm) 158. 80, *158.67, 157.70, *155.10, 144.98, *144.94, 142.58, 138.26, *138.16, 128.34, 128.23, 128.16, 125.55, 124.36, 124.33, *124.16, 37.37, 35.72, 31.16, 29.64, 28.77 (* doubling of the peaks were observed due to the coupling of carbons with fluorine atom); $^{19}$F NMR (400 MHz, CDCl$_3$) δ (ppm) −128.97; HRMS (ESI$^+$) m/z calcd for $C_{17}H_{20}F_1N_2O_1^+$ 287.1542 found 287.1554.

6-(3-cyclohexylpropyl)-3-fluoropicolinaldehyde oxime (Compound 14)

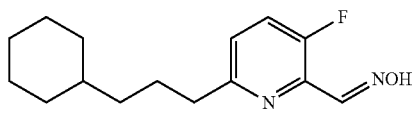

To a degassed solution of fluorooxime 3c (30 mg, 0.115 mmol, 1 equiv) in dry EtOAc (3 mL), 10% Pd/C (6 mg, 0.058 mmol, 0.5 equiv) was added in two portions. After flushing with $H_2$ three times, the reaction mixture was stirred at room temperature under $H_2$ (1 atm.) for 90 min. Upon completion (monitored by TLC), the catalyst was removed by filtration through a short column of celite, the solvent was evaporated, and the residue was purified by preparative TLC (EtOAc/PE 1:4) to afford oxime 14 as a light yellowish solid (29 mg, 95%); $R_f$(20% EA+PE) 0.60; IR (neat) $v_{max}$ 3277, 2923, 2849, 1588, 1472, 1441, 1244, 1124, 987, 947, 841, 805, 754, 736, 719, 666, 585 cm$^{-1}$; $^1$H NMR (400 MHz, CDCl$_3$) δ (ppm) 9.69 (br s, 1H, OH), 8.36 (s, 1H), 7.33 (dd, J=8.6, 10.0 Hz, 1H), 7.12 (dd, J=3.8, 8.6 Hz, 1H), 2.75 (t, J=7.8 Hz, 2H), 1.73-1.57 (m, 7H), 1.25-1.12 (m, 6H), 0.88-0.78 (m, 2H); $^{13}$C NMR (100 MHz, CDCl$_3$) δ (ppm) 158.99, *158.94, 157.74, *155.14, 145.17, *145.14, 138.23, *138.13, 124.34, 124.14, 37.84, 37.50, 37.06, 33.31, 27.25, 26.66, 26.36 (* doubling of the peaks were observed due to the coupling of carbons with fluorine atom); $^{19}$F NMR (400 MHz, CDCl$_3$) δ (ppm) −128.32, −129.07 { 1:15 ratio of cis-trans isomers observed (italic)}; HRMS (ESI$^+$) m/z calcd for $C_{15}H_{22}F_1N_2O_1^+$ 265.1703 found 265.1711.

6-(4-ethylphenethyl)-3-fluoropicolinaldehyde oxime (Compound 15)

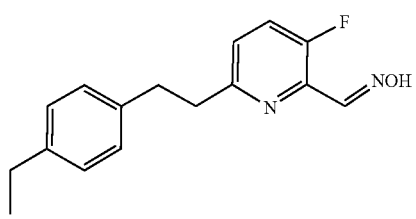

To a degassed solution of fluorooxime 3h (35 mg, 0.130 mmol, 1 equiv) in dry EtOAc (3 mL), 10% Pd/C (7 mg, 0.065 mmol, 0.5 equiv) was added. After flushing with $H_2$ three times, the reaction mixture was stirred at room temperature under $H_2$ (1 atm.) for 2 h. Upon completion (monitored by TLC), the catalyst was removed by filtration through a short column of celite, the solvent was evaporated, and the residue was purified by preperative TLC (EtOAc/PE 1:4) to afford oxime 15 as a light yellowish solid (35 mg, quant. yield); $R_f$ (20% EA+PE) 0.45; IR (neat) $v_{max}$ 3273, 2961, 2926, 2864, 1512, 1472, 1455, 1241, 1180, 984, 836, 724, 657, 577, 512, 467 cm$^{-1}$; $^1$H NMR (400 MHz, CDCl$_3$) δ (ppm) 8.41 (s, 1H), 7.31 (dd, J=8.6, 9.8 Hz, 1H), 7.15-6.99 (m, 6H), 3.10 (m, 2H), 3.01 (m, 2H), 2.60 (q, J=7.6 Hz, 2H), 1.21 (t, J=7.6 Hz, 3H); $^{13}$C NMR (100 MHz, CDCl$_3$) δ (ppm) 157.82, *155.22, 157.72, *157.68, 145.01, *144.98, 141.85, 138.47, *138.37, 138.31, 128.39, 127.81, 124.70, *124.66, 124.30, *124.11, 39.27, 35.39, 28.39, 15.58 (* doubling of the peaks were observed due to the coupling of carbons with fluorine atom); $^{19}$F NMR (400 MHz, CDCl$_3$) δ (ppm) −128.62; HRMS (ESI$^+$) m/z calcd for $C_{16}H_{18}F_1N_2O_1^+$ 273.1388 found 273.1398.

3-fluoro-6-(2-(pyridin-3-yl)ethyl)picolinaldehyde oxime (Compound 16)

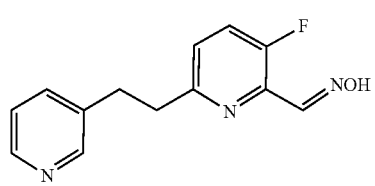

To a degassed solution of fluorooxime 3r (30 mg, 0.124 mmol, 1 equiv) in dry EtOAc (3 mL), 10% Pd/C (10 mg, 0.093 mmol, 0.75 equiv) was added in three portions. After flushing with $H_2$ three times, the reaction mixture was stirred at room temperature under $H_2$ (1 atm.) for 30 h. Upon completion (monitored by TLC), the catalyst was removed by filtration through a short column of celite, the solvent was evaporated, and the residue was purified by preperative TLC (EtOAc/PE 4:1) to afford oxime 16 as a white solid (25 mg, 82%); $R_f$ (80% EA+PE) 0.20; IR (neat) $v_{max}$ 2925, 2853, 2713, 1738, 1579, 1469, 1244, 1176, 1119, 979, 823, 809, 709, 669, 642, 506 cm$^{-1}$; $^1$H NMR (400 MHz, CDCl$_3$) δ (ppm) 11.04 (br s, 1H, OH), 8.45 (br d, J=1.8 Hz, 1H), 8.30 (dd, J=1.5, 4.5 Hz, 1H), 8.22 (s, 1H), 7.62 (dt, J=1.8, 7.8 Hz, 1H), 7.53 (dd, J=8.5, 10.4 Hz, 1H), 7.31-7.20 (m, 2H), 3.16-3.07 (m, 4H); $^{13}$C NMR (100 MHz, CDCl$_3$) δ (ppm) 158.61, *156.0, 157.54, *157.49, 150.97, 148.32, 147.22, *147.16, 137.76, 136.70, 125.42, *125.33, 125.29, 125.*23, 124.14, 39.08, 33.03 (* doubling of the peaks were observed due to the coupling of carbons with fluorine atom); $^{19}$F NMR (400 MHz, CDCl$_3$) δ (ppm) -127.24; HRMS (ESI$^+$) m/z calcd for $C_{13}H_{13}F_1N_3O_1^+$ 246.1032 found 246.1037.

3-fluoro-6-(2-(3-hydroxyoxetan-3-yl)ethyl)picolinaldehyde oxime (Compound 17)

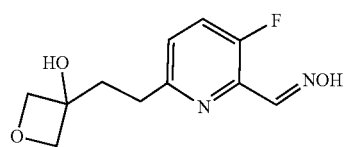

17

To a degassed solution of fluorooxime 3p (45 mg, 0.191 mmol, 1 equiv) in dry EtOAc (3 mL), 10% Pd/C (20 mg, 0.076 mmol, 1 equiv) was added in two portions. After flushing with H$_2$ three times, the reaction mixture was stirred at room temperature under H$_2$ (1 atm.) for 42 h. Upon completion (monitored by TLC), the catalyst was removed by filtration through a short column of celite, the solvent was evaporated, and the residue was purified by preperative TLC (pure EtOAc) to afford oxime 17 as a light yellowish solid (40 mg, 85%); $R_f$(pure EA) 0.35; IR (neat) $v_{max}$ 3352, 2948, 2876, 1592, 1472, 1450, 1311, 1260, 1223, 1110, 948, 964, 833, 643, 542, 526, 469 cm$^{-1}$; $^1$H NMR (400 MHz, CDCl$_3$) δ (ppm) 11.38 (br s, 1H, OH), 8.39 (s, 1H), 7.39 (dd, J=8.6, 9.4 Hz, 1H), 7.21 (dd, J=3.8, 8.6 Hz, 1H), 7.06 (br s, 1H, OH), 4.69 (d, J=6.7 Hz, 2H), 4.40 (d, J=6.8 Hz, 2H), 3.0 (t, J=6.2 Hz, 2H), 2.36 (t, J=6.2 Hz, 2H); $^{13}$C NMR (100 MHz, CDCl$_3$) δ (ppm) 157.55, *154.96, 157.12, *157.08, 141.61, 138.22, *138.11, 125.26, *125.13, 125.08, 83.88, 73.82, 36.23, 31.50 (* doubling of the peaks were observed due to the coupling of carbons with fluorine atom); $^{19}$F NMR (400 MHz, CDCl$_3$) δ (ppm) -127.36, -131.22 { 1:10 ratio of cis-trans isomers observed (italic)}; HRMS (ESI$^+$) m/z calcd for $C_{11}H_{14}F_1N_2O_3^+$ 241.0971 found 241.0983.

3-fluoro-6-(2-(4-hydroxytetrahydro-2H-pyran-4-yl)ethyl)picolinaldehyde oxime (Compound 18)

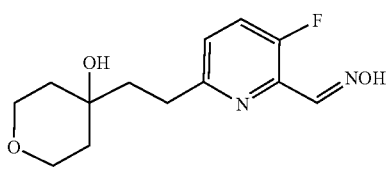

18

To a degassed solution of fluorooxime 30 (40 mg, 0.151 mmol, 1 equiv) in dry EtOAc (3 mL), 10% Pd/C (8 mg, 0.076 mmol, 0.5 equiv) was added. After flushing with H$_2$ three times, the reaction mixture was stirred at room temperature under H$_2$ (1 atm.) for 74 h. Upon completion (monitored by TLC), the catalyst was removed by filtration through a short column of celite, the solvent was evaporated, and the residue was purified by preperative TLC (MeOH/EtOAc 5:95) to afford oxime 18 as a light yellowish liquid (32 mg, 79%); $R_f$ (5% MeOH+EA) 0.40; IR (neat) $v_{max}$ 3271, 2948, 2866, 1591, 1469, 1239, 1180, 1095, 982, 840, 730, 645, 543, 493 cm$^{-1}$; $^1$H NMR (400 MHz, CDCl$_3$) δ (ppm) 11.41 (br s, 1H, OH), 8.39 (s, 1H), 7.35 (dd, J=8.6, 9.5 Hz, 1H), 7.17 (dd, J=3.8, 8.6 Hz, 1H), 5.34 (br s, 1H, OH), 3.85 (td, J=3.4, 10.2 Hz, 2H), 3.74 (m, 2H), 3.0 (t, J=6.9 Hz, 2H), 1.98 (t, J=6.9 Hz, 2H), 1.69-1.61 (m, 4H); $^{13}$C NMR (100 MHz, CDCl$_3$) δ (ppm) 157.96, *157.92, 157.50, *154.92, 155.97, *155.92, 155.26, *152.65, 141.93, 139.04, *138.93, 138.22, *138.11, 135.39, *135.37, 126.05, *126.00, 125.57, *125.39, 125.01, *124.98, 124.86, *124.67, 68.62, 68.19, 63.96, 63.70, 42.31, 41.01, 38.17, 37.57, 30.56, 30.07 (* doubling of the peaks were observed due to the coupling of carbons with fluorine atom); $^{19}$F NMR (400 MHz, CDCl$_3$) δ (ppm) -127.74, -131.68 { 1:5 ratio of cis-trans isomers observed (italic)}; HRMS (ESI$^+$) m/z calcd for $C_{13}H_{18}F_1N_2O_3^+$ 269.1285 found 269.1296.

3-fluoro-6-(10-(5-fluoro-6-((E)-(hydroxyimino)methyl)pyridin-2-yl)decyl)picolinaldehyde oxime (Compound 19)

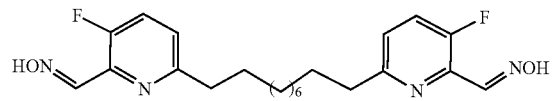

19

To a degassed solution of fluorooxime 3w (40 mg, 0.098 mmol, 1 equiv) in dry EtOAc/MeOH (2/1 mL), 10% Pd/C (10.4 mg, 0.098 mmol, 0.25 equiv) was added. After flushing with H$_2$ three times, the reaction mixture was stirred at room temperature under H$_2$ (1 atm.) for 20 h. Upon completion (monitored by TLC), the catalyst was removed by filtration through a short column of celite, the solvent was evaporated, and the residue was purified by preperative TLC (EtOAc/PE 4:1) to afford oxime 19 as a white solid (35 mg, 86%); $R_f$ (40% EA+PE) 0.55; IR (neat) $v_{max}$ 3072, 2927, 2851, 1583, 1253, 1119, 994, 844, 830, 725, 669, 648, 544 cm$^{-1}$; $^1$H NMR (400 MHz, CD$_3$OD) δ (ppm) 8.26 (s, 1H), 7.53 (dd, J=8.6, 10.2 Hz, 1H), 7.28 (dd, J=3.8, 8.6 Hz, 1H), 2.27 (t, J=7.5 Hz, 2H), 1.69 (p, J=7.5 Hz, 2H), 1.5-1.27 (m, 6H); $^{13}$C NMR (100 MHz, CD$_3$OD) δ (ppm) 160.31, *160.26, 159.19, *156.61, 145.44, *145.40, 140.15, *140.04, 126.15, *126.00, 125.96, 38.23, 31.31, 30.69, 30.60, 30.45 (* doubling of the peaks were observed due to the coupling of carbons with fluorine atom); $^{19}$F NMR (400 MHz, CD$_3$OD) δ (ppm) -130.58; HRMS (ESI$^+$) m/z calcd for $C_{22}H_{29}F_2N_4O_2^+$ 419.2241 found 419.2253.

N-(9-((3aR,4R,6R,6aR)-6-((3-(5-fluoro-6-((hydroxyimino)methyl)pyridin-2-yl)propoxy)methyl)-2,2-dimethyltetrahydrofuro[3,4-d][1,3]dioxol-4-yl)-9H-purin-6-yl)benzamide (Compound 20)

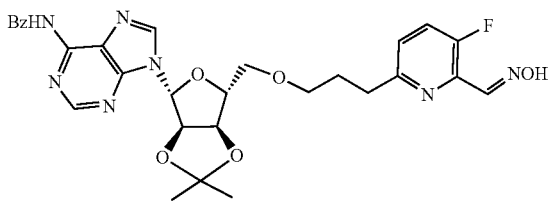

To a degassed solution of fluorooxime 3u (40 mg, 0.068 mmol, 1 equiv) in dry EtOAc (3 mL), 10% Pd/C (7.2 mg, 0.068 mmol, 1 equiv) was added in two portions. After flushing with $H_2$ three times, the reaction mixture was stirred at room temperature under $H_2$ (1 atm.) for 42 h. Upon completion (monitored by TLC), the catalyst was removed by filtration through a short column of celite, the solvent was evaporated, and the residue was purified by preparative TLC (pure EtOAc) to afford oxime 20 as a light yellowish thick syrup (30 mg, 75%); $R_f$ (pure EA) 0.55; IR (neat) $v_{max}$ 3260, 2925, 2857, 1698, 1612, 1582, 1456, 1248, 1211, 1073, 849, 709, 643, 623, 511 cm$^{-1}$; $^1$H NMR (400 MHz, Acetone-d6) δ (ppm) 8.71 (s, 1H), 8.57 (s, 1H), 8.20 (s, 1H), 8.11 (br d, J=7.6 Hz, 2H), 7.63 (m, 1H), 7.56-7.44 (m, 3H), 7.25 (dd, J=3.7, 8.5 Hz, 1H), 6.33 (br d, J=2.2 Hz, 1H), 5.47 (dd, J=2.2, 6.1 Hz, 1H), 5.09 (dd, J=2.5, 6.1 Hz, 1H), 4.48 (m, 1H), 3.70 (dd, J=4, 10.6 Hz, 1H), 3.61 (dd, J=4.4, 10.6 Hz, 1H), 3.52-3.43 (m, 2H), 2.73 (t, J=7.5 Hz, 2H), 1.89 (p, J=7.5 Hz, 2H), 1.59 (s, 3H), 1.38 (s, 3H); $^{13}$C NMR (100 MHz, Acetone-d6) δ (ppm) 166.57, 166.53, 158.57, *158.53, 158.48, *155.88, 152.85, 151.06, 146.61, *146.55, 143.64, 143.59, 139.87, *139.77, 136.51, 136.50, 134.93, 133.41, 130.53, 129.76, 129.46, 129.27, 127.49, 126.67, 126.48, 125.45, *125.41, 125.22, *125.19, 114.34, 92.14, 92.08, 87.19, 85.71, 82.93, 82.88, 71.75, 71.62, 71.31, 71.06, 34.40, 33.94, 32.06, 30.67, 27.57, 25.62 (* doubling of the peaks were observed due to the coupling of carbons with fluorine atom); $^{19}$F NMR (400 MHz, Acetone-d6) δ (ppm) −128.36, −129.16 { 1:3 ratio of cis-trans isomers observed (italic)}; HRMS (ESI$^+$) m/z calcd for $C_{29}H_{31}F_1N_7O_6^+$ 592.2281 found 592.2314.

3-fluoro-6-((E)-6-hydroxyhex-1-en-1-yl)picolinaldehyde oxime (Compound 21)

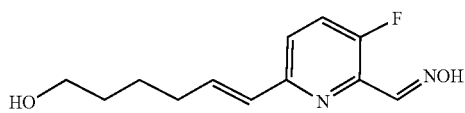

To a degassed solution of fluorooxime 3d (45 mg, 0.190 mmol, 1 equiv) in dry EtOAc (3 mL), 10% Pd/C (5 mg, 0.048 mmol, 0.25 equiv) was added. After flushing with $H_2$ three times, the reaction mixture was stirred at room temperature under $H_2$ (1 atm.) for 4 h. Upon completion (monitored by TLC), the catalyst was removed by filtration through a short column of celite, the solvent was evaporated, and the residue was purified by column chromatography (EtOAc/PE 4:6) to afford oxime 21 as a white solid (40 mg, 88%); $R_f$ (pure EA) 0.75; IR (neat) $v_{max}$ 3275, 2929, 2857, 1644, 1587, 1468, 1252, 1210, 1056, 976, 845, 726, 639, 534 cm$^{-1}$; $^1$H NMR (400 MHz, CDCl$_3$) δ (ppm) 10.61 (br s, 1H, OH), 8.37 (s, 1H), 7.35 (t, J=8.8 Hz, 1H), 7.16 (dd, J=3.8, 8.8 Hz, 1H), 6.38 (br d, J=11.8 Hz, 1H), 5.87 (dt, J=7.6, 11.8 Hz, 1H), 3.66 (t, J=6.0 Hz, 2H), 2.61 (q, J=7.6 Hz, 2H), 1.64-1.49 (m, 4H); $^{13}$C NMR (100 MHz, CDCl$_3$) δ (ppm) 157.40, *154.77, 153.21, 153.16, 144.74, 138.35, *138.26, 138.02, 126.66, 125.74, 125.70, 124.06, *123.87, 67.91, 31.76, 28.00, 25.14 (* doubling of the peaks were observed due to the coupling of carbons with fluorine atom); $^{19}$F NMR (400 MHz, CDCl$_3$) δ (ppm) −127.77; [** There is some impurity observed in the NMR spectra along with compound, which is unable to separate.]; HRMS (ESI$^+$) m/z calcd for $C_{12}H_{16}F_1N_2O_2^+$ 239.1199 found 239.1190.

Methyl (E)-6-(5-fluoro-6-((hydroxyimino)methyl)pyridin-2-yl)hex-5-enoate (Compound 22)

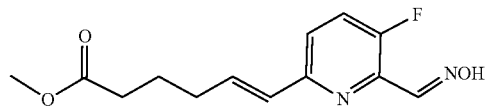

To a degassed solution of fluorooxime 3e (34 mg, 0.128 mmol, 1 equiv) in dry EtOAc (3 mL), 10% Pd/C (3.4 mg, 0.032 mmol, 0.25 equiv) was added. After flushing with $H_2$ three times, the reaction mixture was stirred at room temperature under $H_2$ (1 atm.) for 4 h. Upon completion (monitored by TLC), the catalyst was removed by filtration through a short column of celite, the solvent was evaporated, and the residue was purified by column chromatography (EtOAc/PE 1:3) to afford oxime 22 as a white solid (30 mg, 87%); $R_f$ (20% EA+PE) 0.65; IR (neat) $v_{max}$ 3256, 2937, 1727, 1582, 1466, 1249, 1189, 1169, 1005, 973, 865, 844, 733, 710, 629, 611, 520 cm$^{-1}$; $^1$H NMR (400 MHz, CDCl$_3$) δ (ppm) 9.62 (br s, 1H, OH), 8.33 (s, 1H), 7.34 (dd, J=8.6, 10.0 Hz, 1H), 7.19 (dd, J=3.8, 8.6 Hz, 1H), 6.43 (dt, J=1.6, 11.7 Hz, 1H), 5.86 (dt, J=7.5, 11.7 Hz, 1H), 3.60 (s, 3H), 2.62 (qd, J=1.6, 7.6 Hz, 2H), 2.62 (t, J=7.6 Hz, 2H), 1.82 (p, J=7.6 Hz, 2H); $^{13}$C NMR (100 MHz, CDCl$_3$) δ (ppm) 174.18, 157.45, *154.81, 152.92, 152.88, 146.09, *146.04, 138.39, *138.29, 136.79, 127.42, 125.56, 125.51, 124.23, *124.04, 51.52, 33.62, 28.10, 24.72 (* doubling of the peaks were observed due to the coupling of carbons with fluorine atom); $^{19}$F NMR (400 MHz, CDCl$_3$) δ (ppm) −126.11; HRMS (ESI$^+$) m/z calcd for $C_{13}H_{16}F_1N_2O_3^+$ 267.1114 found 267.1139.

3-fluoro-6-((E)-2-(pyren-4-yl)vinyl)picolinaldehyde oxime (Compound 23)

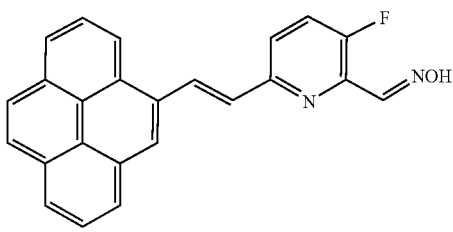

To a degassed solution of fluorooxime 3j (45 mg, 0.123 mmol, 1 equiv) in dry EtOAc (3 mL), 10% Pd/C (6.5 mg, 0.061 mmol, 0.5 equiv) was added in two portions. After flushing with $H_2$ three times, the reaction mixture was stirred at room temperature under $H_2$ (1 atm.) for 12 min. Upon completion (monitored by TLC), the catalyst was removed by filtration through a short column of celite, the solvent was evaporated, and the residue was purified by washings with DCM and EtoAc to afford oxime 23 as a yellowish solid (30 mg, 66%); $R_f$(30% EA+PE) 0.50; IR (neat) $v_{max}$ 2958, 2926, 2856, 1721, 1585, 1461, 1266, 1248, 1117, 1102, 974, 955, 839, 729, 694, 540 $cm^{-1}$; $^1H$ NMR (500 MHz, DMSO) δ (ppm) 12.00 (s, 1H), 8.73 (d, J=16 Hz, 1H), 8.67 (d, J=9.4 Hz, 1H), 8.56 (d, J=8.2 Hz, 1H), 8.36-8.29 (m, 5H), 8.21 (s, 2H), 8.10 (t, J=7.7 Hz, 1H), 7.95 (dd, J=3.8, 8.6 Hz, 1H), 7.87 (dd, J=8.6, 10.3 Hz, 1H), 7.63 (d, J=16 Hz, 1H); $^{13}C$ NMR (125 MHz, DMSO) δ (ppm) 157.30, *155.20, 151.66, *151.64, 145.65, *145.60, 139.32, *139.24, 130.99, 130.90, 130.38, 130.34, 129.57, 128.84, 128.24, 127.99, 127.65, 127.41, 126.47, 125.66, 125.38, 125.30, *125.14, 124.25, *124.00, 123.90, 123.87, 123.74, 122.87 (* doubling of the peaks were observed due to the coupling of carbons with fluorine atom); $^{19}F$ NMR (400 MHz, DMSO) δ (ppm) −123.84; HRMS (ESI$^+$) m/z calcd for $C_{24}H_{16}F_1N_2O_1^+$ 367.1229 found 367.1241.

3-fluoro-6-(4-((1,2,3,4-tetrahydroacridin-9-yl)amino)butyl)picolinaldehyde oxime (Compound 24)

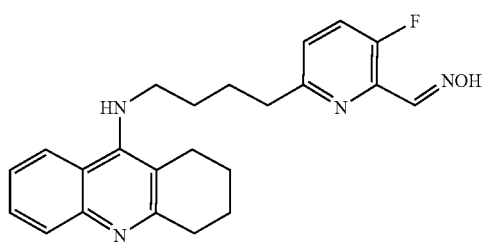

24

To a degassed solution of fluorooxime 3z (20 mg, 0.052 mmol, 1 equiv) in dry EtOAc/MeOH (2/1 mL), 10% Pd/C (5.5 mg, 0.052 mmol, 1 equiv) was added. After flushing with $H_2$ three times, the reaction mixture was stirred at room temperature under $H_2$ (1 atm.) for 20 h. Upon completion (monitored by TLC), the catalyst was removed by filtration through a short column of celite, the solvent was evaporated, and the residue was purified by preparative TLC (EtOAc/PE 4:1) to afford oxime 24 as a white solid (20 mg, quant. yield); $R_f$ (20% MeOH+EA) 0.20; IR (neat) $v_{max}$ 2923, 2857, 1562, 1503, 1467, 1434, 1299, 1244, 1166, 1114, 986, 832, 749, 678, 621, 543 $cm^{-1}$; *$^1H$ NMR (400 MHz, $CD_3OD$) δ (ppm) 8.19 (s, 1H, oxime), 8.09 (brd, J=8.6 Hz, 1H, Ar), 7.73 (brd, J=8.6 Hz, 1H, Ar), 7.62-7.57 (m, 1H, Ar), 7.44-7.34 (m, 2H, Ar), 7.14 (dd, J=3.8, 8.6 Hz, 1H, Ar), 3.62 (t, J=6.9 Hz, 2H), 2.95 (br t, J=5.9 Hz, 2H), 2.75 (t, J=7.0 Hz, 2H), 2.67 (t, J=5.9 Hz, 2H), 1.92-1.85 (m, 4H) 1.77-1.65 (m, 4H); *$^{13}C$ NMR (100 MHz, $CD_3OD$) δ (ppm) 159.62, 159.57, 159.11, 157.80, 157.75, 157.44, 156.52, 154.27, 154.06, 146.04, 145.32, 145.29, 140.11, 140.01, 130.85, 126.60, 126.53, 126.41, 126.23, 126.16, 126.05, 126.02, 125.97, 125.86, 125.22, 124.95, 124.88, 120.54, 120.40, 116.22, 116.03 (Ar), 148.94, 37.48, 37.20, 33.27, 33.21, 31.38, 31.24, 28.12, 27.52, 26.09, 26.02, 23.99, 23.93, 23.46, 23.37 (* doubling of the peaks were observed due to the coupling of carbons with fluorine atom); *$^{19}F$ NMR (400 MHz, $CD_3OD$) δ (ppm) −123.32, −130.21 (*cis-trans isomers); HRMS (ESI$^+$) m/z calcd for $C_{23}H_{26}F_1N_4O^+$ 393.2085 found 393.2118.

9-((4-(5-fluoro-6-((hydroxyimino)methyl)pyridin-2-yl)butyl)amino)-1,2,3,4-tetrahydroacridin-10-ium chloride (Compound 25)

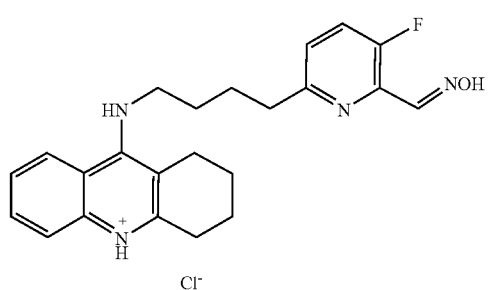

25

To a compound 24 (1 equiv) in methanol (0.5 mL), was added 1.2 N HCl (0.5 mL) and agitated for 2 min and kept it for 10 min at rt. The reaction mixture was concentrated under reduced pressure to get the HCl salt 25 as a white solid in quantitative yield. IR (neat) $v_{max}$ 2937, 2866, 1633, 1571, 1523, 1439, 1359, 1295, 1176, 990, 757, 678, 534 $cm^{-1}$; $^1H$ NMR (400 MHz, $D_2O$) δ (ppm) 8.02 (s, 1H, oxime), 7.88, 7.83 (2d, J=8.8 Hz, 1H, Ar), 7.72 (m, 1.3H, Ar), 7.57 (t, J=9.0 Hz, 1.3H, Ar), 7.47 (m, 1.3H, Ar), 7.42-7.33 (m, 2.6H, Ar), 3.72, 3.67 (2t, J=5.9 Hz, 2.6H), 2.88-2.65 (m, 5.2H), 2.36 (m, 2.6H), 1.92-1.63 (m, 11H); $^{19}F$ NMR (400 MHz, $D_2O$) δ (ppm) −119.94, −125.06 (1:2 ratio of cis-trans isomers); HRMS (ESI$^+$) m/z calcd for $C_{23}H_{26}F_1N_4O_1^+$ 393.2085 found 393.2090.

3-fluoro-6-(4-(quinolin-4-ylamino)but-1-yn-1-yl)picolinaldehyde oxime (Compound 26)

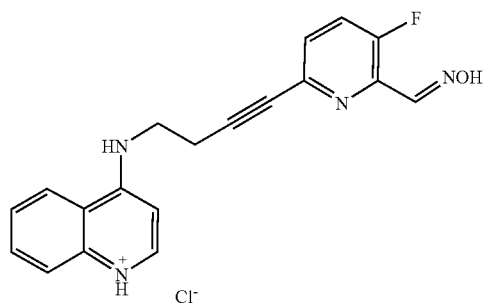

26

To a compound 3y (10 mg) in methanol/water (0.5 mL/0.5 mL), 1.2 N HCl (0.5 mL) and agitated for 2 min and kept it for 10 min at rt. The reaction mixture was concentrated under reduced pressure to get the HCl salt 26 as a white solid in quantitative yield. IR (neat) $v_{max}$ 226, 3089, 2913, 2239, 1605, 1590, 1565, 1466, 1436, 1230, 970, 961, 834, 799, 755, 681, 636, 493 $cm^{-1}$; **$^1H$ NMR (500 MHz, $CD_3OD$) δ (ppm) 8.48-8.36 (m, 2.7H), 8.23, 8.18 (2s, 1.2H), 7.95 (m, 1.4H), 7.87 (m, 1.4H), 7.84-7.62 (m, 2.7H), 7.58-7.47 (m, 1.3H), 7.06, 6.94 (2d, J=7.2 Hz, 1.3H), 3.95, 3.78 (2t, J=7.7

Hz, 2.7H), 2.99, 2.80 (2t, J=7.7 Hz, 2H); **$^{13}$C NMR (120 MHz, CD$_3$OD) δ (ppm) 159.50, 158.10, 157.38, 144.55, 144.52, 143.83, 143.81, 143.39, 139.88, 139.84, 139.47, 135.16, 133.93, 131.07, 131.03, 130.36, 130.32, 128.96, 128.79, 128.49, 127.49, 127.33, 124.03, 123.92, 121.27, 118.56, 118.47, 99.76, 99.60, 90.29, 80.93, 75.48, 67.91, 43.15, 43.08, 20.18, 19.83 (* doubling of the peaks were observed due to the coupling of carbons with fluorine atom); $^{19}$F NMR (400 MHz, CD$_3$OD) δ (ppm) −124.00, −127.87 (1:3 ratio cis-trans isomers); HRMS (ESI$^+$) m/z calcd for C$_{19}$H$_{16}$F$_1$N$_4$O$_1$$^+$ 335.1303 found 335.1311.

3-fluoro-6-(4-(quinolin-4-ylamino)butyl)picolinaldehyde oxime (Compound 27)

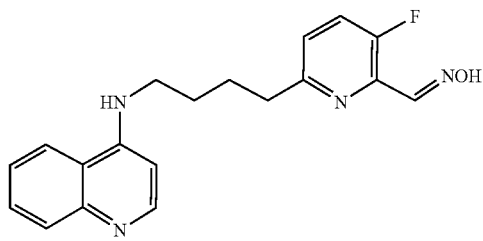

27

To a degassed solution of fluorooxime 3y (40 mg, 0.120 mmol, 1 equiv) in dry EtOAc/MeOH (2/1 mL), 10% Pd/C (6.4 mg, 0.060 mmol, 0.5 equiv) was added as thrice as portions for every 24 hours. After flushing with H$_2$ three times, the reaction mixture was stirred at room temperature under H$_2$ (1 atm.) for 64 h. Upon completion (monitored by TLC), the catalyst was removed by filtration through a short column of celite, the solvent was evaporated, and the residue was purified by preparative TLC (EtOAc/PE 4:1) to afford oxime 27 as a white solid (36 mg, 89%). R$_f$ (30% MeOH+ EA) 0.20; IR (neat) v$_{max}$ 3326, 2918, 2851, 1581, 1456, 1442, 1351, 996, 803, 775, 704, 614, 545, 473 cm$^{-1}$; $^1$H NMR (500 MHz, DMSO-d6) δ (ppm) 11.85 (s, 1H, OH), 8.36 (d, J=5.3 Hz, 1H, Ar), 8.20 (dd, J=1.2, 8.4 Hz, 1H, Ar), 8.14 (s, 1H, Oxime), 7.76 (dd, J=1.0, 8.4 Hz, 1H, Ar), 7.68 (dd, J=8.5, 10.7 Hz, 1H, Ar), 7.59 (m, 1H, Ar), 7.39 (m, 1H, Ar), 7.35 (dd, J=3.8, 8.6 Hz, 1H, Ar), 7.17 (t, J=5.1 Hz, 1H), 6.53 (d, J=5.5 Hz, 1H), 3.30 (t, J=7.5 Hz, 2H), 2.80 (t, J=7.5 Hz, 2H), 1.79 (m, 2H) 1.69 (m, 2H); *$^{13}$C NMR (125 MHz, DMSO-d6) δ (ppm) 158.19, *158.16, 157.24, *155.17, 150.99, 150.44, 148.60, 145.98, *145.93, 138.98, *138.91, 129.31, 129.21, 125.35, 125.20, 124.75, *124.72, 124.22, 124.18, 119.27, 98.60, 42.66, 36.69, 27.81, 27.27 (* doubling of the peaks were observed due to the coupling of carbons with fluorine atom); $^{19}$F NMR (400 MHz, CD$_3$OD) δ (ppm) −126.78.

4-((4-(5-fluoro-6-((hydroxyimino)methyl)pyridin-2-yl)butyl)ammonio)quinolin-1-ium chloride (Compound 28)

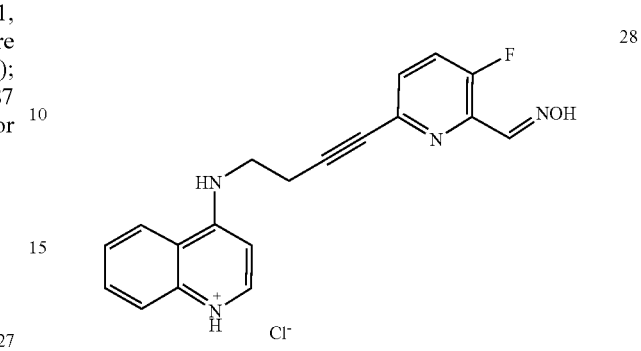

28

To a compound 27 (6 mg) in methanol/water (0.5 mL/0.5 mL), was added 1.2 N HCl (25 μL) and agitated for 2 min and kept it for 10 min at rt. The reaction mixture was concentrated under reduced pressure to get the HCl salt 28 as a white solid in quantitative yield. **$^1$H NMR (500 MHz, CD$_3$OD) δ (ppm) 8.19-8.11 (m, 2H), 8.00 (d, J=8.6 Hz, 1H), 7.89-7.81 (m, 2H), 7.71 (d, J=8.6 Hz, 1H), 7.64-7.57 (m, 2H), 6.59 (d, J=7.2 Hz, 1.3H), 3.51 (t, J=6.8 Hz, 2.7H), 2.96 (2t, J=7.7 Hz, 2H), 1.92-1.75 (m, 4H); $^{19}$F NMR (400 MHz, CD$_3$OD) δ (ppm) −125.24; HRMS (ESI) m/z calcd for C$_{19}$H$_{20}$F$_1$N$_4$O$_1$$^+$ 339.1616 found 339.1604.

3-((5-fluoro-6-((hydroxyimino)methyl)pyridin-2-yl)ethynyl)pyridin-1-ium chloride (Compound 29)

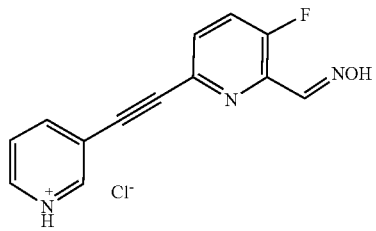

29

To a compound 3r (8 mg) in water (0.5 mL), was added 1.2 N HCl (0.5 mL) and agitated for 2 min and kept it for 10 min at rt. The reaction mixture was concentrated under reduced pressure to get the HCl salt 29 as a white solid in quantitative yield. IR (neat) v$_{max}$ 3453, 3376, 3008, 2911, 1634, 1532, 1458, 1248, 1205, 1109, 996, 934, 844, 800, 764, 671, 628, 525 cm$^{-1}$; H NMR (400 MHz, D$_2$O) δ (ppm) 9.03 (br s, 1H), 8.81 (dt, J=1.1, 5.8 Hz, 1H), 8.74 (dt, J=1.6, 8.3 Hz, 1H), 8.35 (s, 1H), 8.12 (m, 1H), 7.79-7.71 (m, 2H); $^{13}$C NMR (100 MHz, D$_2$O) δ (ppm) 159.61, *156.96, 149.54, 144.95, 144.32, 141.42, 140.16, *140.30, 137.35, *137.30, 131.29, *131.23, 127.90, 126.71, *126.51, 123.08, 93.23, 82.28 (* doubling of the peaks were observed due to the coupling of carbons with fluorine atom); $^{19}$F NMR (400 MHz, D$_2$O) δ (ppm) −120.57; HRMS (ESI$^+$) m/z calcd for C$_{13}$H$_9$F$_1$N$_3$O$_1$$^+$ 242.0724 found 242.0700.

3-(2-(5-fluoro-6-((hydroxyimino)methyl)pyridin-2-yl)ethyl)pyridin-1-ium-chloride (Compound 30)

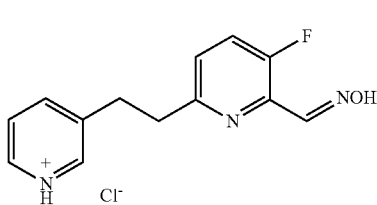

To a compound 16 (10 mg) in methanol (0.5 mL), was added 1.2 N HCl (0.5 mL) and agitated for 2 min and kept it for 10 min at rt. The reaction mixture was concentrated under reduced pressure to get the HCl salt 30 as a white solid in quantitative yield. IR (neat) $v_{max}$ 2925, 2594, 2399, 1651, 1557, 1471, 1443, 1281, 1193, 1009, 990, 882, 799, 783, 685, 632, 526, 489 cm$^{-1}$; $^1$H NMR (400 MHz, D$_2$O) δ (ppm) 8.66-8.62 (m, 2H), 8.47-8.39 (m, 2H), 8.01-7.94 (m, 2H), 7.62 (dd, J=4.2, 8.8 Hz, 1H), 3.38-3.30 (m, 4H); $^{13}$C NMR (100 MHz, D$_2$O) δ (ppm) 158.78, *156.20, 155.15, *155.11, 147.89, 142.05, 141.27, 141.10, 139.89, 136.97, *1136.78, 131.08, *130.89, 128.31, *128.25, 127.80, 35.18, 32.17 (* doubling of the peaks were observed due to the coupling of carbons with fluorine atom); $^{19}$F NMR (400 MHz, D$_2$O) δ (ppm) −119.42, −124.91 (cis-trans isomers); HRMS (ESI$^+$) m/z calcd for C$_{13}$H$_{13}$F$_1$N$_3$O$_1^+$ 246.1037 found 246.1019.

5-bromo-3-fluoropicolinaldehyde oxime (Compound 31)

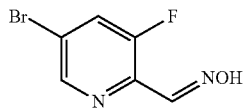

A solution of commercially available 5-bromo-3-fluoropicolinaldehyde (85 mg, 0.42 mmol, 1 equiv), hydroxylamine hydrochloride (58 mg, 0.83 mmol, 2 equiv), and CH$_3$CO$_2$Na (103 mg, 1.26 mmol, 3 equiv) in dry ethanol (4 mL) was stirred at reflux during 16 h. After completion (checked by TLC), the reaction mixture was filtered through a small celite pad. The filtrate was concentrated under reduced pressure and the residue was purified by column chromatography (EtOAc/PE 1:9) to afford the oxime 31 as a white solid (80 mg, 88%). R$_f$ (20% EA+PE) 0.50; $^1$H NMR (400 MHz, Acetone-d6) δ (ppm) 11.13 (br s, 1H, OH), 8.58 (br t, J=1.2 Hz, 1H, H$_6$), 8.21 (s, 1H, H$_7$), 8.01 (dd, J=1.8, 10.0 Hz, 1H, H$_4$); *$^{13}$C NMR (100 MHz, Acetone-d6) δ (ppm) 159.13, *156.43 (C3), 147.49, *147.45 (C6), 146.49, *146.42 (C7), 141.0, *140.10 (C2), 128.23, *128.02 (C4), 120.46, *120.44 (C5) (* doubling of the peaks were observed due to the coupling of carbons with fluorine atom); $^{19}$F NMR (400 MHz, Acetone-d6) δ (ppm) −119.20; HRMS (ESI$^+$) m/z calcd for C$_6$H$_5$Br$_1$F$_1$N$_2$O$_1^+$ 218.9564 found 218.9558.

3-fluoro-5-(5-phenylpent-1-yn-1-yl)picolinaldehyde oxime (Compound 32)

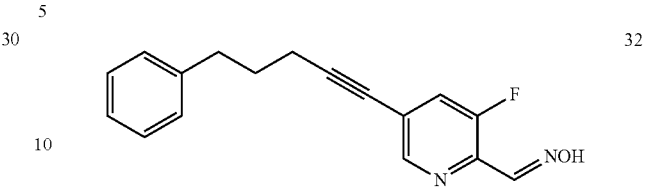

To a degassed solution of 5-bromo-3-fluoropicolinaldehyde oxime 31 (61 mg, 028 mmol, 1 equiv) in THF/Et$_3$N (4 mL/2 mL), Pd[PPh$_3$]$_4$ (49 mg, 0.042 mmol, 0.15 equiv) and CuI (16 mg, 0.084 mmol, 0.3 equiv) were added. After degassing the reaction mixture for 5 min at room temperature, the alkyne 1a (5-phenyl-1-pentyne, 40 mg, 0.28 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 32 as a white solid (25 mg, 32%). R$_f$ (20% EA+PE) 0.40; IR (neat) 3270, 2922, 2226, 1600, 1401, 1313, 1159, 1079, 983, 872, 696, 621, 578 cm$^{-1}$; $^1$H NMR (400 MHz, CDCl$_3$) δ (ppm) 8.44 (s, H, H$_6$), 8.35 (s, 1H, H$_{18}$), 7.42 (d, J=10.5 Hz, 1H, H$_4$), 7.32-7.1 (m, 5H, Ar), 2.76 (t, J=7. Hz, 2H, H$_{11}$), 2.4 (t, J=7.1 Hz, 2H, H$_9$), 1.93 (quintet, J=7.1, 7.4 Hz, 2H, H$_{10}$); *$^{13}$C NMR (100 MHz, CDCl$_3$) δ (ppm) 158.20, *156.08 (C3), 140.46 (C6), 145.01, *144.97 (C18), 142.32 (C12), 137.62, *137.57 (C2), 128.50 (C14, C16), 128.44, (C13, C17), 126.08 (C15), 124.45 (C4), 123.26 (C5), 96.88 (C8), 69.17 (C7), 34.87 (C11), 29.70 (C10), 18.96 (C9) (* doubling of the peaks were observed due to the coupling of carbons with fluorine atom); $^{19}$F NMR (400 MHz, CDCl$_3$) δ (ppm) −124.70; HRMS (ESI$^+$) m/z calcd for C$_{17}$H$_{16}$F$_1$N$_2$O$_1^+$ 283.1241 found 283.1210.

5-bromo-2-fluoronicotinaldehyde oxime (Compound 33)

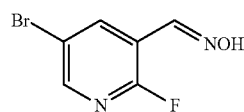

A solution of commercially available 5-bromo-2-fluoronicotinaldehyde (1 g, 4.902 mmol, 1 equiv), hydroxylamine hydrochloride (681 mg, 9.804 mmol, 2 equiv), and CH$_3$CO$_2$Na (1.2 g, 14.706 mmol, 3 equiv) in dry ethanol (40 mL) was stirred at reflux during 16 h. After completion (checked by TLC), the reaction mixture was filtered through a small celite pad. The filtrate was concentrated under reduced pressure and the residue was purified by column chromatography (EtOAc/PE 1:9) to afford the oxime 33 as a white solid (1.05 g, quant. yield). R$_f$ (20% EA+PE) 0.50; IR (neat) 3218, 3004, 2921, 1618, 1559, 1479, 1427, 1312, 1249, 1159, 995, 939, 898, 834, 753, 642, 564, 478 cm$^{-1}$; *$^1$H NMR (400 MHz, Acetone-d6) δ (ppm) 11.17 (br s, 1H, OH), 8.37-8.32 (m, 2H, H$_4$, H$_5$), 8.17 (s, 1H, H$_7$); $^{13}$C NMR (100 MHz, Acetone-d6) δ (ppm) 160.62, *159.22 (C2), 149.55, *149.40 (C6), 141.22, *141.19 (C7), 139.99, *139.96 (C4), 118.97, *118.68 (C3), 117.5, *117.55 (C5) (* doubling of the peaks were observed due to the coupling of carbons with fluorine atom); $^{19}$F NMR (400 MHz, Acetone-d6) δ (ppm) −74.02, −77.27 (cis-trans); HRMS (ESI$^+$) m/z calcd for $C_6H_5Br_1F_1N_2O_1^+$ 218.9564 found 218.9551.

2-fluoro-5-(5-phenylpent-1-yn-1-yl)nicotinaldehyde oxime (Compound 34)

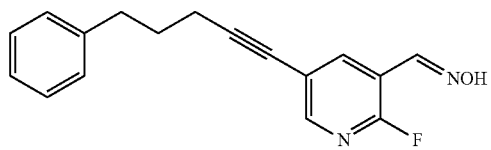

To a degassed solution of 5-bromo-2-fluoronicotinaldehyde oxime 33 (133 mg, 0.610 mmol, 1.1 equiv) in THF/Et$_3$N (6 mL/3 mL), Pd[PPh$_3$]$_4$ (96 mg, 0.083 mmol, 0.15 equiv) and CuI (32 mg, 0.167 mmol, 0.3 equiv) were added. After degassing the reaction mixture for 5 min at room temperature, the alkyne 1a (5-phenyl-1-pentyne, 80 mg, 0.555 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 34 as a white solid (70 mg, 45%). R$_f$ (20% EA+PE) 0.40; IR (neat) 3210, 3085, 2923, 2855, 2233, 1575, 1448, 1317, 1254, 1143, 980, 911, 830, 748, 702, 646, 582, 485 cm$^{-1}$; $^1$H NMR (400 MHz, CDCl$_3$) δ (ppm) 8.36 (br s, 1H, OH), 8.24-8.21 (m, 2H, H$_6$,H$_{18}$), 8.15 (dd, J=2.3, 8.8 Hz, 1H, H$_4$), 7.31-7.16 (m, 5H, Ar), 2.76 (t, J=7.4 Hz, 2H, H$_{11}$), 2.41 (t, J=7.1 Hz, 2H, H$_9$), 1.92 (quintet, J=7.1, 7.4 Hz, 2H, H$_{10}$); $^{13}$C NMR (100 MHz, CDCl$_3$) δ (ppm) 160.61, *158.18 (C2), 151.04, *150.89 (C18), 142.42, *142.39 (C6), 141.23 (C12), 139.68, *139.65 (C4), 128.48, 128.41 (C13, C14, C16, C17), 126.02 (C15), *119.64, 119.59 (C5), 114.86, *114.60 (C3), 93.95 (C8), 76.06 (C7), 34.83 (C11), 29.92 (C10), 18.76 (C9) (* doubling of the peaks were observed due to the coupling of carbons with fluorine atom); $^{19}$F NMR (400 MHz, CDCl$_3$) δ (ppm) −73.52; HRMS (ESI$^+$) m/z calcd for $C_{17}H_{16}F_1N_2O_1^+$ 283.1241 found 283.1242.

3-bromo-6-chloropicolinaldehyde oxime (Compound 35)

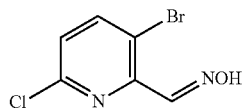

A solution of commercially available 3-bromo-6-chloropicolinaldehyde (220 mg, 1 mmol, 1 equiv), hydroxylamine hydrochloride (139 mg, 2 mmol, 2 equiv), and CH$_3$CO$_2$Na (246 mg, 3 mmol, 3 equiv) in dry ethanol (8 mL) was stirred at reflux during 16 h. After completion (checked by TLC), the reaction mixture was filtered through a small celite pad. The filtrate was concentrated under reduced pressure and the residue was purified by column chromatography (EtOAc/Pentane 1:9) to afford the oxime 35 as a white solid (225 mg, 96%). R$_f$ (20% EA+PE) 0.70; IR (neat) 3003, 2325, 2148, 1568, 1442, 1358, 1344, 1257, 1103, 1054, 997, 927, 885, 763, 643, 542, 478 cm$^{-1}$; $^1$H NMR (400 MHz, Acetone-d6) δ (ppm) 8.39 (s, 1H), 8.32 (s, 1H), 7.94 (s, 1H); HRMS (ESI$^+$) m/z calcd for $C_6H_5Br_1Cl_1N_2O_1^+$ 234.9268 found 234.9259.

6-chloro-3-(5-phenylpent-1-yn-1-yl)picolinaldehyde oxime (Compound 36)

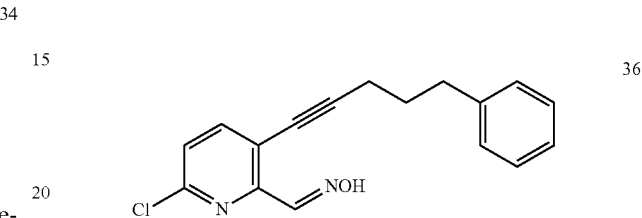

To a degassed solution of oxime 35 (135 mg, 0.572 mmol, 1.1 equiv) in THF/Et$_3$N (6 mL/3 mL), Pd[PPh$_3$]$_4$ (90 mg, 0.078 mmol, 0.15 equiv) and CuI (30 mg, 0.156 mmol, 0.3 equiv) were added. After degassing the reaction mixture for 5 min at room temperature, the alkyne 1a (5-phenyl-1-pentyne 75 mg, 0.520 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/Pentane 1:9) to afford the desired coupled fluoro oxime 36 as a white solid (140 mg, 90%). R$_f$ (20% EA+PE) 0.60; IR (neat) 3024, 2921, 2852, 2234, 1582, 1494, 1458, 1377, 1287, 1180, 1077, 996, 922, 746, 696, 660, 579, 479 cm$^{-1}$; $^1$H NMR (400 MHz, CDCl$_3$) δ (ppm) 10.04-9.44 (br s, H, OH), 8.52 (s, 1H), 8.42 (s, 1H), 7.82 (br s, 1H), 7.28-7.14 (m, 5H, Ar), 2.76 (t, J=7.5 Hz, 2H, H$_{11}$), 2.42 (t, J=7.0 Hz, 2H, H$_9$), 1.92 (quintet, J=7.0, 7.5 Hz, 2H, H$_{10}$); $^{13}$C NMR (100 MHz, CDCl$_3$) δ (ppm) 149.97, 144.35, 141.72, 141.23, 138.07, 129.19, 128.48, 128.35, 125.95, 123.39, 92.58, 79.47, 34.77, 29.73, 18.73; HRMS (ESI$^+$) m/z calcd for $C_{17}H_{16}Cl_1N_2O_1^+$ 299.0946 found 299.0945.

6-bromo-4-chloronicotinaldehyde oxime (Compound 37)

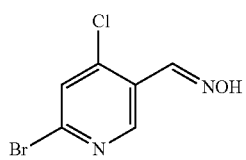

A solution of commercially available 6-bromo-4-chloronicotinaldehyde (240 mg, 1.089 mmol, 1 equiv), hydroxylamine hydrochloride (151 mg, 2.18 mmol, 2 equiv), and CH$_3$CO$_2$Na (268 mg, 3.27 mmol, 3 equiv) in dry ethanol (8 mL) was stirred at reflux during 16 h. After completion (checked by TLC), the reaction mixture was filtered through a small celite pad. The filtrate was concentrated under reduced pressure and the residue was purified by column chromatography (EtOAc/Pentane 1:9) to afford the oxime 37 as a white solid (255 mg, quantitative yield). $R_f$ (20% EA+PE) 0.60; IR (neat) 3223, 3089, 2414, 1602, 1563, 1527, 1442, 1323, 1115, 1056, 984, 939, 879, 766, 680, 517, 453 cm$^{-1}$; $^1$H NMR (400 MHz, CD$_3$OD) δ (ppm) 8.71 (s, 1H), 8.33 (s, 1H), 7.77 (s, 1H); $^{13}$C NMR (100 MHz, CD$_3$OD) δ (ppm) 149.06, 145.10, 143.36, 142.85, 129.69, 128.61; HRMS (ESI$^+$) m/z calcd for $C_6H_5Br_1Cl_1N_2O_1{}^+$ 234.9268 found 234.9270.

4-chloro-6-(5-phenylpent-1-yn-1-yl)nicotinaldehyde oxime (Compound 38)

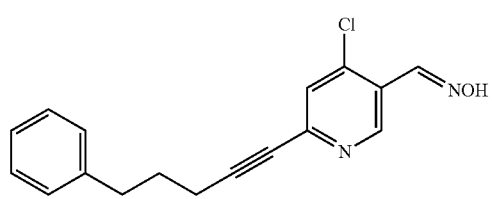

To a degassed solution of oxime 37 (72 mg, 0.305 mmol, 1.1 equiv) in THF/Et$_3$N (4 mL/2 mL), Pd[PPh$_3$]$_4$ (48 mg, 0.042 mmol, 0.15 equiv) and CuI (16 mg, 0.083 mmol, 0.3 equiv) were added. After degassing the reaction mixture for 5 min at room temperature, the alkyne 1a (5-phenyl-1-pentyne, 40 mg, 0.28 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled fluoro oxime 38 as a white solid (74 mg, 89%). $R_f$ (20% EA+PE) 0.40; IR (neat) 3028, 2924, 2854, 2746, 2227, 1578, 1494, 1456, 1306, 1288, 1068, 992, 874, 781, 745, 696, 581, 475 cm$^{-1}$; $^1$H NMR (400 MHz, CDCl$_3$) δ (ppm) 10.99 (br s, H, OH), 9.07 (br s, 1H), 8.43 (s, 1H), 7.38 (br s, 1H), 7.29-7.12 (m, 5H, Ar), 2.76 (t, J=7.4 Hz, 2H, H$_{11}$), 2.44 (t, J=7.1 Hz, 2H, H$_9$), 1.92 (quintet, J=7.1, 7.4 Hz, 2H, H$_{10}$); *$^{13}$C NMR (100 MHz, CDCl$_3$) δ (ppm) 147.99, 143.76, 143.56, 142.77, 141.19, 128.50, 128.35, 127.52, 125.95, 94.44, 79.37, 34.74, 29.65, 18.81; HRMS (ESI$^+$) m/z calcd for $C_{17}H_{16}Cl_1N_2O_1{}^+$ 299.0946 found 299.0945.

3-fluoro-6-(pentadec-yn-1-yl)picolinonitrile (Compound 39)

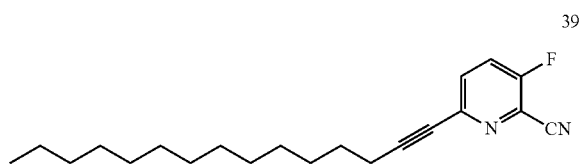 [SMILES: CCCCCCCCCCCCCC#Cc1ccc(F)c(C#N)n1]

To a degassed solution of picolinonitrile 6 (43 mg, 0.216 mmol, 1.0 equiv) in THF/Et$_3$N (4 mL/2 mL), Pd[PPh$_3$]$_4$ (37.5 mg, 0.032 mmol, 0.15 equiv) and CuI (12.4 mg, 0.065 mmol, 0.3 equiv) were added. After degassing the reaction mixture for 5 min at room temperature, the alkyne 1b (45 mg, 0.216 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled picolinonitrile 39 as a yellowish solid (60 mg, 85%). $R_f$ (20% EtOAc+PE) 0.60; $^1$H NMR (400 MHz, CDCl$_3$) δ (ppm) 7.60-7.47 (m, 2H), 2.41 (t, J=7.2 Hz, 2H), 1.61 (m, 2H) 1.41 (m, 2H), 1.30-1.20 (m, 18H), 0.85 (t, J=6.8 Hz, 3H); $^{13}$C NMR (100 MHz, CDCl$_3$) δ (ppm) 161.26, 158.56, 141.72, 141.68, 131.91, 131.86, 125.00, 124.83, 122.71, 122.55, 112.38, 112.33, 93.94, 78.01, 31.91, 29.63, 29.60, 29.46, 29.34, 29.08, 28.96, 28.07, 22.68, 19.28, 14.11; $^{19}$F NMR (400 MHz, CDCl$_3$) δ (ppm) −116.14.

6-((4-ethylphenyl)ethynyl)-3-fluoropicolinonitrile (Compound 40)

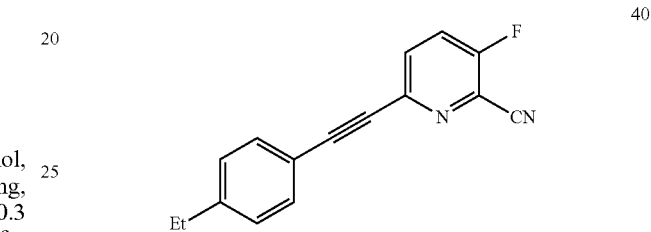

To a degassed solution of picolinonitrile 6 (68 mg, 0.337 mmol, 1.1 equiv) in THF/Et$_3$N (4 mL/2 mL), Pd[PPh$_3$]$_4$ (53 mg, 0.046 mmol, 0.15 equiv) and CuI (18 mg, 0.092 mmol, 0.3 equiv) were added. After degassing the reaction mixture for 5 min at room temperature, the alkyne 1h (40 mg, 0.307 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 1:9) to afford the desired coupled picolinonitrile 40 as a yellowish solid (71 mg, 92%). $R_f$ (10% EtOAc+PE) 0.50; $^1$H NMR (400 MHz, CDCl$_3$) δ (ppm) 7.71 (m, 1H), 7.57 (dd, J=7.7, 8.9 Hz, 1H), 7.49 (m, 2H), 7.21 (m, 2H), 2.66 (q, J=7.6 Hz, 2H), 1.23 (t, J=7.6 Hz, 3H); $^{19}$F NMR (400 MHz, CDCl$_3$) δ (ppm) −115.72.

3-fluoro-6-(4-morpholinobut-1-yn-1-yl)picolinonitrile (Compound 42)

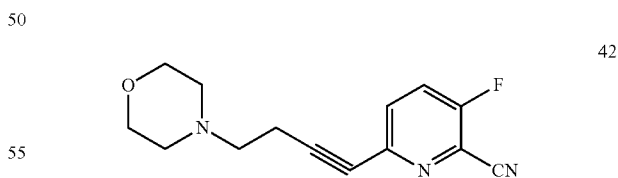

To a degassed solution of picolinonitrile 6 (75 mg, 0.375 mmol, 1 equiv) in THF/Et$_3$N (4 mL/2 mL), Pd[PPh$_3$]$_4$ (65 mg, 0.056 mmol, 0.15 equiv) and CuI (21 mg, 0.113 mmol, 0.3 equiv) were added. After degassing the reaction mixture for 5 min at room temperature, 4-(but-3-yn-1-yl)morpholine 41 (commercially available from Enamine LTd) (47 mg, 0.395 mmol, 1 equiv) was added dropwise and the reaction mixture was stirred at the room temperature for 16 h. After completion (checked by TLC), the reaction mixture was concentrated under reduced pressure and the residue was purified by column chromatography (MeOH/EtOAc 5:95) to afford the desired coupled picolinonitrile 42 as a yellowish solid (62.4 mg, 64%). R$_f$ (100% EtOAc) 0.30; $^1$H NMR (400 MHz, CDCl$_3$) δ (ppm) ) 7.59-7.48 (m, 2H), 3.69 (m, 4H), 2.69-2.58 (m, 4H), 2.48 (m, 4H); $^{13}$C NMR (100 MHz, CDCl$_3$) δ (ppm) 161.32, *158.62, 141.31, *141.26, 131.93, *131.89, 125.11, *124.92, 122.75, *122.58, 112.29, *112.25, 91.42, 78.69, 66.82, 56.70, 53.23, 17.40 (* doubling of the peaks were observed due to the coupling of carbons with fluorine atom); $^{19}$F NMR (400 MHz, CDCl$_3$) δ (ppm) −118.86; HRMS (ESI$^+$) m/z calcd for C$_{14}$H$_{15}$F$_1$N$_3^+$ 260.1194 found 260.1196.

3-fluoro-6-((3-hydroxyoxetan-3-yl)ethynyl)picolinonitrile (Compound 43)

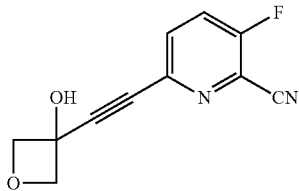

To a degassed solution of picolinonitrile 6 (51 mg, 0.254 mmol, 1 equiv) in THF/Et$_3$N (4 mL/2 mL), Pd[PPh$_3$]$_4$ (44 mg, 0.038 mmol, 0.15 equiv) and CuI (14.5 mg, 0.076 mmol, 0.3 equiv) were added. After degassing the reaction mixture for 5 min at room temperature, the alkyne 1p (25 mg, 0.254 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 7:3) to afford the desired coupled picolinonitrile 43 as a white solid (50 mg, 90%). R$_f$ (80% EtOAc+PE) 0.30; $^1$H NMR (400 MHz, CDCl$_3$) δ (ppm)) 7.69 (dd, J=4.1, 8.8 Hz, 1H), 7.60 (dd, J=7.6, 8.8 Hz, 1H), 4.93 (dd, J=0.7, 6.8 Hz, 2H), 4.78 (dd, J=0.7, 6.8 Hz, 2H); $^{19}$F NMR (400 MHz, CDCl$_3$) δ (ppm) −113.76.

6-((1-aminocyclohexyl)ethynyl)-3-fluoropicolinonitrile (Compound 44)

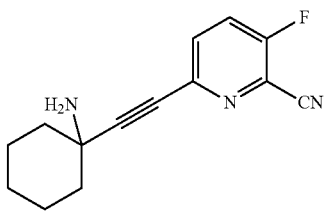

To a degassed solution of picolinonitrile 6 (62 mg, 0.309 mmol, 1.0 equiv) in THF/Et$_3$N (4 mL/2 mL), Pd[PPh$_3$]$_4$ (53 mg, 0.046 mmol, 0.15 equiv) and CuI (17.5 mg, 0.092 mmol, 0.3 equiv) were added. After degassing the reaction mixture for 5 min at room temperature, the alkyne 1f (40 mg, 0.309 mmol, 1 equiv) was added dropwise and the reaction mixture was stirred at the room temperature for 16 h. After completion (checked by TLC), the reaction mixture was concentrated under reduced pressure and the residue was purified by column chromatography (EtOAc/PE 95:5) to afford the desired coupled picolinonitrile 44 as a yellowish solid (68 mg, 90%). R$_f$ (10% MeOH+EtOAc) 0.50; $^1$H NMR (400 MHz, CDCl$_3$) δ (ppm) ) 7.65-7.46 (m, 2H), 1.88 (m, 1H), 1.72-7.10 (m, 10H); $^{13}$C NMR (100 MHz, CDCl$_3$) δ (ppm) 161.29, *158.60, 141.24, *141.19, 132.19, *132.15, 125.05, *124.86, 122.62, *122.46, 112.27, *112.22, 98.18, 79.98, 39.78, 29.56, 25.09, 23.15 (* doubling of the peaks were observed due to the coupling of carbons with fluorine atom); $^{19}$F NMR (400 MHz, CDCl$_3$) δ (ppm) −115.89; HRMS (ESI$^+$) m/z calcd for C$_{14}$H$_{15}$F$_1$N$_3^+$ 244.1245 found 244.1245.

(3aS,4S,6R,6aR)-6-(6-amino-9H-purin-9-yl)-N-(4-(6-cyano-5-fluoropyridin-2-yl)but-3-yn-1-yl)-2,2-dimethyltetrahydrofuro[3,4-d][1,3]dioxole-4-carboxamide (Compound 45)

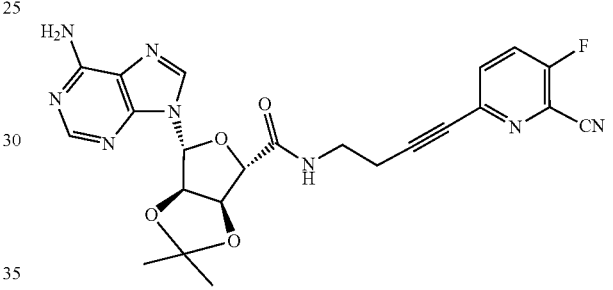

To a degassed solution of picolinonitrile 6 (50.5 mg, 0.251 mmol, 1.1 equiv) in THF/Et$_3$N (6 mL/3 mL), Pd[PPh$_3$]$_4$ (40 mg, 0.034 mmol, 0.15 equiv) and CuI (13 mg, 0.068 mmol, 0.3 equiv) were added. After degassing the reaction mixture for 5 min at room temperature, the alkyne 1v (85 mg, 0.228 mmol, 1 equiv) was added dropwise and the reaction mixture was stirred at the room temperature for 16 h. After completion (checked by TLC), the reaction mixture was concentrated under reduced pressure and the residue was purified by column chromatography (MeOH/EtOAc 5:95) to afford the desired coupled picolinonitrile 45 as a yellowish solid (106 mg, 94%). R$_f$ (100% EtOAc) 0.20; $^1$H NMR (400 MHz, Acetone-d6) δ (ppm) ) 8.27-8.14 (2s, 2H), 7.90 (t, J=8.8, 1H), 7.78-7.71 (m, 2H), 6.98 (br s, 2H), 6.35 (d, J=2 Hz, 1H), 5.52 (dd, J=2, 6.1 Hz, 1H), 5.46 (dd, J=2, 6.1 Hz, 1H), 4.66 (d, J=2.0 Hz, 1H), 3.27 (m, 2H), 2.46 (m, 1H), 2.31 (m, 1H), 1.58 (s, 3H), 1.38 (s, 3H); $^{13}$C NMR (100 MHz, Acetone-d6) δ (ppm) 170.04, 162.57, *159.91, 157.27, 153.82, 150.07, 141.88, *141.84, 141.44, 133.97, *133.92, 126.71, *126.52, 123.10, *122.93, 120.74, 114.50, 113.60, *113.55, 90.88, 90.62, 87.56, 84.81, 84.33, 79.86, 38.09, 27.31, 25.50, 20.23 (* doubling of the peaks were observed due to the coupling of carbons with fluorine atom); $^{19}$F NMR (400 MHz, Acetone-d6) δ (ppm) −118.50; HRMS (ESI$^+$) m/z calcd for C$_{23}$H$_{22}$F$_1$N$_8$O$_4^+$ 493.1743 found 493.1741.

Amidoxime Derivatives 3-fluoro-N'-hydroxy-6-(pentadec-1-yn-1-yl)picolinimidamide (Compound 46)

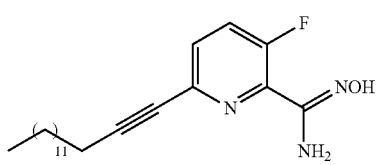

A solution of coupled picolinonitrile 39 (40 mg, 0.122 mmol, 1 equiv), hydroxylamine hydrochloride (13 mg, 0.183 mmol, 1.5 equiv), and Na$_2$CO$_3$ (19 g, 0.183 mmol, 1.5 equiv) in dry ethanol (4 mL) was stirred at reflux during 16 h. After completion (checked by TLC), the reaction mixture was filtered through a small celite pad. The filtrate was concentrated under reduced pressure and the residue was purified by column chromatography (EtOAc/PE 2:3) to afford the amidoxime 46 as a white solid (40 mg, 91%). R$_f$ (80% EtOAc+PE) 0.60; $^1$H NMR (400 MHz, CDCl$_3$) δ (ppm) 9.54 (br s, 1H, OH), 7.44-7.32 (m, 2H, Ar), 5.67 (br s, 2H), 2.41 (t, J=7.1 Hz, 2H), 1.61 (quintet, J=7.1, 7.4 Hz, 2H), 1.42 (m, 2H), 1.23 (s, 18H), 0.86 (t, J=6.5 Hz, 3H); $^{13}$C NMR (100 MHz, CDCl$_3$) δ (ppm) 157.85, *155.176, 148.85, *148.75, 138.72, *138.67, 136.69, *136.60, 128.58, *128.53, 125.29, *125.07, 91.43, 79.10, 31.91, 29.64, 29.50, 29.34, 29.14, 28.99, 28.30, 22.68, 19.29, 14.11 (* doubling of the peaks were observed due to the coupling of carbons with fluorine atom); $^{19}$F NMR (400 MHz, CDCl$_3$) δ (ppm) −116.71; HRMS (ESI$^+$) m/z calcd for C$_{21}$H$_{33}$F$_1$N$_3$O$_1^+$ 362.2602 found 362.2605.

6-((4-ethylphenyl)ethynyl)-3-fluoro-N'-hydroxypicolinimidamide (Compound 47)

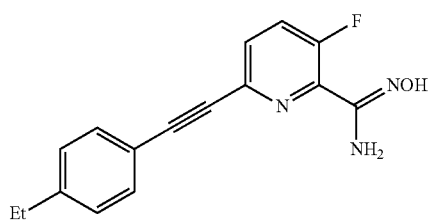

A solution of coupled picolinonitrile 40 (50 mg, 0.20 mmol, 1 equiv), hydroxylamine hydrochloride (21 mg, 0.30 mmol, 1.5 equiv), and Na$_2$CO$_3$ (32 g, 0.30 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (EtOAc/PE 1:3) to afford the amidoxime 47 as a white solid (72 mg, 91%). R$_f$ (30% EtOAc+PE) 0.30; $^1$H NMR (400 MHz, DMSO-d6) δ (ppm) 10.21 (br s, 1H, OH), 7.83 (dd, J=8.6, 10.5 Hz), 7.74 (dd, J=2.8, 8.6 Hz, 1H), 7.54 (d, J=7.9 Hz, 2H), 7.31 (d, J=7.9 Hz, 2H), 5.86 (br s, 2H), 2.65 (q, J=7.6 Hz, 2H), 1.19 (t, J=7.6 Hz, 3H); $^{13}$C NMR (100 MHz, DMSO-d6) δ (ppm) 157.49, *154.83, 145.66, 137.32, *137.28, 131.73, 131.51, *131.42, 128.79, *128.68, 128.33, 125.77, *125.77, 118.35, 88.78, 87.28, 28.11, 15.19 (* doubling of the peaks were observed due to the coupling of carbons with fluorine atom); $^{19}$F NMR (400 MHz, DMSO-d6) δ (ppm) −116.08; HRMS (ESI$^+$) m/z calcd for C$_{16}$H$_{15}$F$_1$N$_3$O$_1^+$ 284.1194 found 284.1197.

3-fluoro-N'-hydroxy-6-(4-morpholinobut-1-yn-1-yl)picolinimidamide (Compound 48)

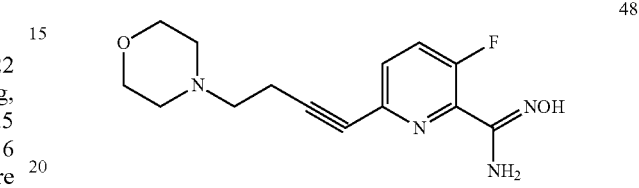

A solution of coupled picolinonitrile 42 (55 mg, 0.212 mmol, 1 equiv), hydroxylamine hydrochloride (22 mg, 0.318 mmol, 1.5 equiv), and Na$_2$CO$_3$ (34 g, 0.318 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (MeOH/EtOAc 5:95) to afford the amidoxime 48 as a white solid (38 mg, 61%). R$_f$ (5% MeOH+EtOAc) 0.30; $^1$H NMR (400 MHz, DMSO-d6) δ (ppm)) 10.17 (s, 1H), 7.75 (dd, J=8.6, 10.5 Hz, 1H), 7.54 (dd, J=3.4, 8.6 Hz, 1H), 5.78 (br s, 2H), 3.58 (br t, J=4.5 Hz, 4H), 2.68-2.56 (m, 4H), 2.47-2.40 (m, 4H); $^{13}$C NMR (100 MHz, DMSO-d6) δ (ppm) 156.99, *154.87, 147.88, *147.81, 138.68, *138.59, 137.70, *137.66, 128.21, *128.47, 125.85, *125.68, 89.33, 79.85, 66.11, 56.45, 52.85, 16.61 (* doubling of the peaks were observed due to the coupling of carbons with fluorine atom); $^{19}$F NMR (400 MHz, DMSO-d6) δ (ppm) −116.87; HRMS (ESI$^+$) m/z calcd for C$_{14}$H$_{18}$F$_1$N$_4$O$_2^+$ 293.1408 found 293.1409.

3-fluoro-N'-hydroxy-6-((3-hydroxyoxetan-3-yl)ethynyl)picolinimidamide (Compound 49)

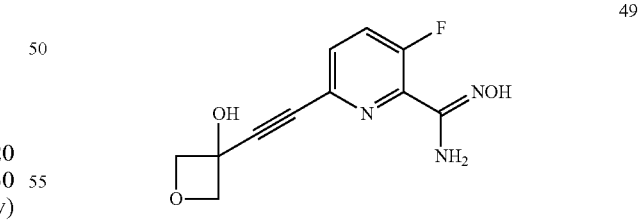

A solution of coupled picolinonitrile 43 (30 mg, 0.137 mmol, 1 equiv), hydroxylamine hydrochloride (14 mg, 0.206 mmol, 1.5 equiv), and Na$_2$CO$_3$ (22 g, 0.206 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (EtOAc/PE 4:1) to afford the amidoxime 49 as a white solid (27.6 mg, 88%). R$_f$ (100% EtOAc) 0.30; $^1$H NMR (400 MHz, Acetone-d6) δ

(ppm)) 9.49 (s, 1H), 7.69 (dd, J=8.5, 10.4 Hz, 1H), 7.62 (dd, J=3.5, 8.5 Hz, 1H), 5.72 (br s, 2H), 4.84 (dd, J=0.6, 6.4 Hz, 2H), 4.70 (dd, J=0.6, 6.4 Hz, 2H); $^{13}$C NMR (100 MHz, Acetone-d6) δ (ppm) 159.14, *156.46, 149.41, *149.32, 139.75, *139.65, 138.09, *138.04, 129.78, *129.73, 126.64, *126.43, 89.83, 84.92, 83.87, 67.54 (* doubling of the peaks were observed due to the coupling of carbons with fluorine atom); $^{19}$F NMR (400 MHz, Acetone-d6) δ (ppm) −115.44; HRMS (ESI$^+$) m/z calcd for $C_{11}H_{11}F_1N_3O_3$ 252.0779 found 252.0781.

6-((1-aminocyclohexyl)ethynyl)-3-fluoro-N'-hydroxypicolinimidamide (Compound 50)

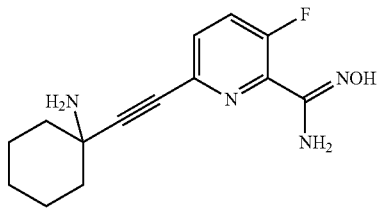

A solution of coupled picolinonitrile 44 (60 mg, 0.247 mmol, 1 equiv), hydroxylamine hydrochloride (26 mg, 0.370 mmol, 1.5 equiv), and Na$_2$CO$_3$ (39 mg, 0.370 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (MeOH/EtOAc 1:9) to afford the amidoxime 50 as a white solid (54 mg, 79%). R$_f$ (10% MeOH+EtOAc) 0.20; $^1$H NMR (400 MHz, CD$_3$OD) δ (ppm) ) 7.62 (dd, J=8.7, 10.1 Hz, 1H), 7.54 (dd, J=3.5, 8.7 Hz, 1H), 2.02-1.94 (m, 2H), 1.76-1.64 (m, 5H), 1.54-1.45 (m, 2H), 1.32-1.26 (m, 2H); $^{13}$C NMR (100 MHz, CD$_3$OD) δ (ppm) 159.50, *156.84, 150.87, *150.76, 139.99, *139.87, 139.81, *139.76, 130.42, *130.38, 126.91, *126.70, 95.25, 83.13, 51.49, 40.63, 26.48, 24.60 (* doubling of the peaks were observed due to the coupling of carbons with fluorine atom); $^{19}$F NMR (400 MHz, CD$_3$OD) δ (ppm) −118.88; HRMS (ESI$^+$) m/z calcd for $C_{14}H_{18}F_1N_4O^+$ 277.1459 found 277.1460.

(3aS,4S,6R,6aR)-6-(6-amino-9H-purin-9-yl)-N-(4-(5-fluoro-6-((E)-N'-hydroxycarbam-imidoyl)pyridin-2-yl)but-3-yn-1-yl)-2,2-di methyltetrahydrofuro[3,4-d][1,3]dioxole-4-carboxamide (Compound 51)

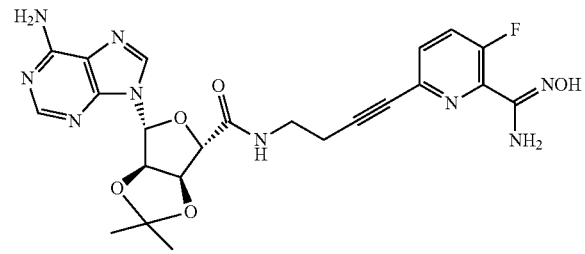

A solution of coupled picolinonitrile 45 (85 mg, 0.173 mmol, 1 equiv), hydroxylamine hydrochloride (18 mg, 0.256 mmol, 1.5 equiv), and Na$_2$CO$_3$ (27 mg, 0.256 mmol, 1.5 equiv) in dry ethanol (5 mL) was stirred at reflux during 16 h. After completion (checked by TLC), the reaction mixture was filtered through a small celite pad. The filtrate was concentrated under reduced pressure and the residue was purified by column chromatography (MeOH/EtOAc 1:9) to afford the amidoxime 51 as a white solid (70.5 mg, 78%). R$_f$ (5% MeOH+EtOAc) 0.30; $^1$H NMR (400 MHz, CD$_3$OD) δ (ppm) ) 8.11 (s, 1H), 8.08 (s, 1H), 7.44 (dd, J=8.6, 10.2 Hz, 1H), 7.25 (dd, J=3.5, 8.6 Hz, 1H), 6.23 (d, J=1.3 Hz, 1H), 5.48 (dd, J=2.0, 6.1 Hz, 1H), 5.31 (dd, J=2.0, 6.1 Hz, 1H), 4.59 (d, J=2.0 Hz, 1H), 3.13 (m, 1H), 3.02 (m, 1H), 2.22 (m, 1H), 2.05 (m, 1H), 1.27 (s, 3H), 1.17 (s, 3H); $^{13}$C NMR (100 MHz, CD$_3$OD) δ (ppm) 172.12, 159.31, *156.66, 157.40, 124.06, 150.30, 142.52, 139.64, *139.55, 130.21, *130.16, 126.82, *126.61, 120.58, 115.23, 92.61, 88.64, 88.60, 85.29, 81.13, 38.71, 27.30, 25.53, 20.38 (* doubling of the peaks were observed due to the coupling of carbons with fluorine atom); $^{19}$F NMR (400 MHz, CD$_3$OD) δ (ppm) −118.89; HRMS (ESI$^+$) m/z calcd for $C_{23}H_{25}F_1N_9O_5^+$ 526.1957 found 526.1970.

Example 2: In Vitro Reactivation of Human Acetylcholinesterase (hAChE) by Compound 30

Compound 30 above, i.e. 3-(2-(5-fluoro-6-((hydroxyimino)methyl)pyridin-2-yl)ethyl)pyridin-1-ium-chloride

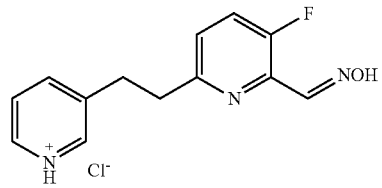

was tested for its reactivation properties of hAChE inhibited by O-ethyl S-[2-(diisopropylamino)ethyl] methylphosphonothioate (VX), tabun or sarin. 2-PAM (pralidoxime or 2-[(E)-(hydroxyimino)methyl]-1-methylpyridinium) and H16 (asoxime chloride or [1-[(4-carbamoylpyridin-1-ium-1-yl)methoxymethyl]pyridin-2-ylidene]methyl-oxoazanium dichloride) were used as comparative compounds.

The protocol was as follows:

Materials and methods are already described in WO2017021319, in *European Journal of Medicinal Chemistry* 2014, 78, 455-467, and in *J. Med. Chem.* 2018, 61, 7630-7639.

IC$_{50}$ measurements. Recombinant hAChE was produced and purified as previously described (Carletti et al 2008 J Am Chem Soc 130(47): 1601 1-20). Oximes were dissolved in MeOH to make 5 mM or 10 mM stock solution and further diluted in phosphate buffer (sodium phosphate 0.1 M, pH 7.4). Recombinant hAChE activity was measured spectrophotometrically (absorbance at 412 nm) in the presence of various concentrations of oximes in 1 mL Ellman's buffer (sodium phosphate 0.1 M, pH 7.4, 0.1% BSA, 0.5 mM DTNB, 25° C.). Measurements were performed at least in duplicate for each concentration tested. The concentration of oxime producing 50% of enzyme inhibition was determined by non-linear fitting using ProFit (Quantumsoft) using the standard IC$_{50}$ equation:

% Activity=100*IC$_{50}$/(IC$_{50}$+[Ox]).

Inhibition of hAChE by OPNAs. Recombinant hAChE was produced and purified as previously described (see reference: http://www.ncbi.nlm.nih.gov/pubmed/18975951). VX and tabun were from DGA maitrise NRBC (Vert le Petit, France). Stock solution of VX, sarin and tabun were 5 mM in isopropanol. The inhibition of 120 μM hAChE was carried out with a 5-fold excess of OPNAs and was performed in tris buffer (20 mM, pH 7.4, 0.1% BSA) at 25° C. After a 20-minute incubation, inhibited hAChE was desalted on PD-10 column (GE Healthcare).

Reactivation of hAChE inhibited by OPNAs. OPNA-inhibited hAChE was incubated at 37° C. with at least 4 or 5 concentrations of oxime in phosphate buffer (0.1 M, pH 7.4, 0.1% BSA). The final concentration of MeOH in the incubation mix was below 2% and had no influence on the enzyme stability. At time intervals ranging from 1 to 10 minutes depending on the reactivation rate, 10 aliquots of each solution containing the different concentrations of oxime were transferred to cuvettes containing 1 mM acetyl-thiocholine in 1 mL Ellman's buffer (phosphate 0.1 M, pH 7.4, 0.1% BSA, 0.5 mM DTNB, 25° C.) for measurement of hAChE activity.

The enzyme activity in the control remained constant during the experiment. The percentage of reactivated enzyme (% E$_{react}$) was calculated as the ratio of the recovered enzyme activity and activity in the control. The apparent reactivation rate kobs for each oxime concentration, the dissociation constant KO of inhibited enzyme-oxime complex (E-POx) and the maximal reactivation rate constant ki, were calculated by non-linear fit with ProFit (Quantumsoft) using the standard oxime concentration-dependent reactivation equation derived from the following scheme:

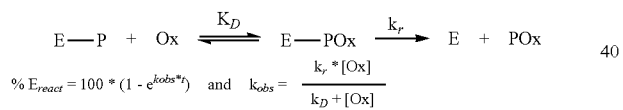

The results are as follows (Table 1):

TABLE 1

Reactivation of OP-inhibited human hAChE by oximes 2-PAM, HI6 and 30

| OP | Oxime (μM) | k$_r$ (min$^{-1}$) | K$_D$ (μM) | kr$_2$ (mM$^{-1}$ min$^{-1}$) |
|---|---|---|---|---|
| VX | 2-PAM | 0.19 ± 0.013 | 26 ± 7 | 7.3 |
|  | HI6 | 0.38 ± 0.02 | 19 ± 4 | 20 |
|  | 30.HCl | 0.04 ± 0.001 | 8.2 ± 1.6 | 4.8 |
| Sarin | 2-PAM | 0.27 ± 0.02 | 24.8 ± 7.12 | 10.8 |
|  | HI6 | 0.76 ± 0.06 | 57 ± 11 | 13.3 |
|  | 30.HCl | 0.15 ± 0.006 | 1.8 ± 0.4 | 82.6 |
| Tabun | 2-PAM | 0.47 ± 0.19 | 211 ± 113 | 2.24 |
|  | HI6 | 0 | 0 | 0 |
|  | 30.HCl | 0 | 0 | 0 |

IC$_{50}$ of 30: 628 +/− 124 μM

They showed that the compound 30 of the invention has the best affinity for the various OP agents, and specifically for VX and Sarin.

The invention claimed is:
1. A compound of formula (II), or one of its pharmaceutically acceptable salts:

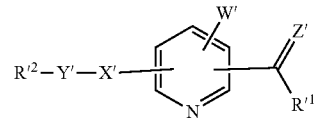

(II)

wherein:

W' is F or Cl;

—X'—Y'— is —C≡C— or —X'—Y'— is Br and R2 does not exist;

R'1 is H;

Z' is =N—OH;

R'2 is a group chosen from aralkyl;

or a compound of formula (I), or one of its pharmaceutically acceptable salts:

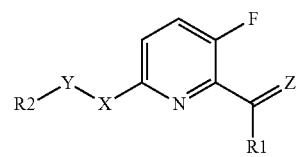

(I)

wherein:

—X—Y— is —CH2-CH2-, —C≡C—, —CH=CH—, or —X—Y— is Br and R2 does not exist;

R1 is H, NHOH or —NH2;

Z is O or =N—OH;

R2 is selected from the group consisting of alkyl, haloalkyl, hydroxyalkyl, aryl, aralkyl, heteroaryl, heterocyclyl, halogen, cyano, R—O—CO—R'— wherein R and R' are each independently alkyl groups, —R3-N(R4)(R5), alkylsulfonamide, alkenyl, a biomolecule, a fluorescent probe, radical A and radical B, wherein radical A or radical B may be linked to —Y—X— by an alkyl group:

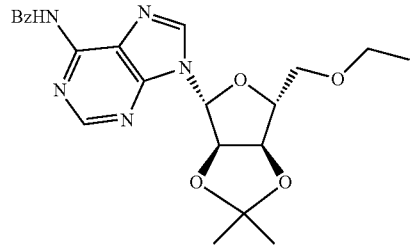

A

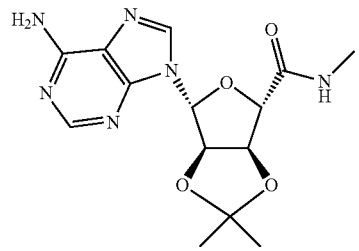

B or R2 is an alkyl group linked to the following radical:

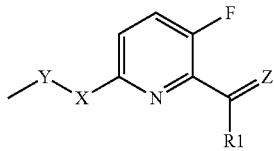

R3 is an alkyl group, and
R4 and R5 are identical or different and each independently represent H, R6-O—CO— with R6 being an alkyl group, a carboxybenzyl group, a pyridine group, a 7-chloro-2,3-dihydro-1H-cyclopenta[b]quinolin-9-yl radical, a quinolin-4-yl radical, an acridin-9-yl radical or
R4 and R5 form together with the nitrogen atom a 1,3-dioxoisoindolin-2-yl,
with the exception of 6-bromo-3-fluoro-2-pyridine hydroxamic acid, of 6-bromo-3-fluoropicolinaldehyde and of 6-bromo-3-fluoro-2-pyridinecarboxamide.

2. The compound of claim 1 wherein in formula (I):
—X—Y— is —CH2-CH2-, —C≡C— or —CH═CH;
R1 is H;
Z is ═N—OH;
R2 is selected from the group consisting of alkyl, haloalkyl, hydroxyalkyl, aryl, aralkyl, heteroaryl, heterocyclyl, halogen, cyano, —R—O—CO—R'— wherein R and R' are both independently alkyl groups, —R3-N(R4)(R5), alkylsulfonamide, alkenyl, radical A and radical B, wherein radical A or radical B may be linked to —Y—X— by an alkyl group:

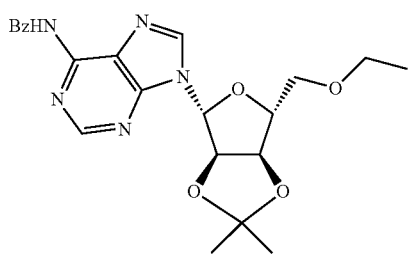

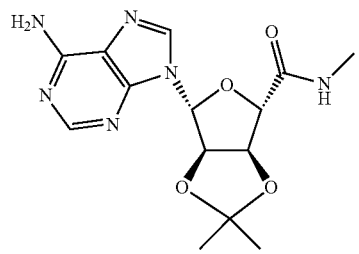

or R2 is an alkyl group linked to the following radical:

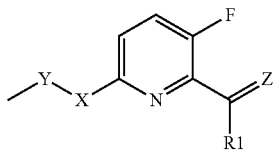

R3 is an alkyl group, and
R4 and R5 are identical or different and each independently represent H, R6-O—CO— with R6 being an alkyl group, a carboxybenzyl group, a pyridine group, a 7-chloro-2,3-dihydro-1H-cyclopenta[b]quinolin-9-yl radical, a quinolin-4-yl radical, an acridin-9-yl radical or
R4 and R5 form together with the nitrogen atom a 1,3-dioxoisoindolin-2-yl.

3. The compound of claim 1, having scaffold 1 below:

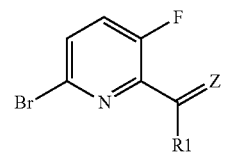

Scaffold 1 wherein R1 and Z are as defined in claim 1, with the exception of 6-bromo-3-fluoro-2-pyridine hydroxamic acid.

4. The compound of claim 1, wherein in formula (I) R1 is H and Z is ═N—OH.

5. The compound of claim 1, wherein in formula (I) R1 is —NHOH and Z is O, with the exception of 6-bromo-3-fluoro-2-pyridine hydroxamic acid.

6. The compound of claim 1, wherein in formula (I) R1 is —NH2 and Z is ═N—OH.

7. The compound of claim 1, wherein in formula (I):
—X—Y— is —CH2-CH2-, —C≡C— or —CH═CH;
R1 is —NHOH;
Z is O; and
R2 is a group chosen from alkyl, haloalkyl, hydroxyalkyl, aryl or aralkyl.

8. The compound of claim 1, wherein in formula (I):
—X—Y— is —CH2-CH2-, —C≡C— or —CH═CH;
R1 is —NH2;
Z is ═N—OH; and
R2 is a group chosen from alkyl, haloalkyl, hydroxyalkyl, aryl or aralkyl.

9. The compound of claim 1, which is chosen among the following:

(Z)-6-bromo-3-fluoropicolinaldehyde oxime 2:

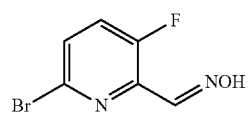

3-fluoro-6-(5-phenylpent-1-yn-1-yl)picolinaldehyde oxime 3a:

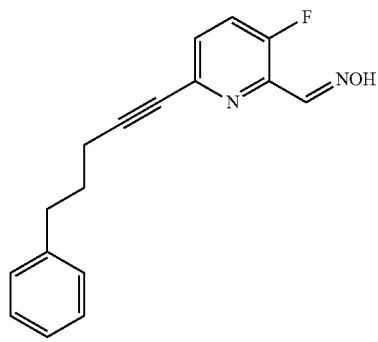

3-fluoro-6-(pentadec-1-yn-1-yl)picolinaldehyde oxime 3b:

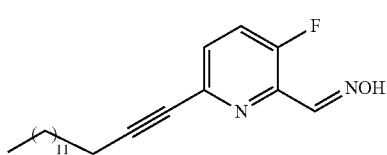

6-(3-cyclohexylprop-1-yn-1-yl)-3-fluoropicolinaldehyde oxime 3c:

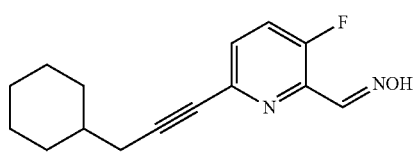

3-fluoro-6-(6-hydroxyhex-1-yn-1-yl)picolinaldehyde oxime 3d:

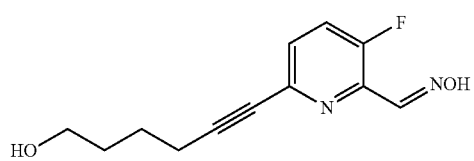

Methyl 6-(5-fluoro-6-((hydroxyimino)methyl)pyridin-2-yl)hex-5-ynoate 3e:

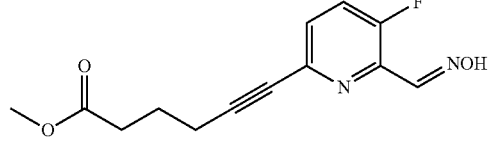

6-((1-aminocyclohexyl)ethynyl)-3-fluoropicolinaldehyde oxime 3f:

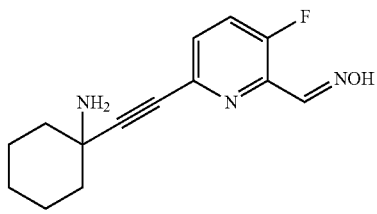

3-fluoro-6-(hex-5-en-1-yn-1-yl)picolinaldehyde oxime 3g:

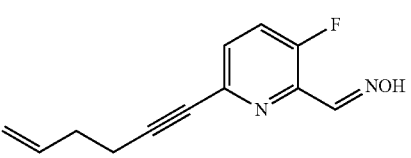

6-((4-ethylphenyl)ethynyl)-3-fluoropicolinaldehyde oxime 3h:

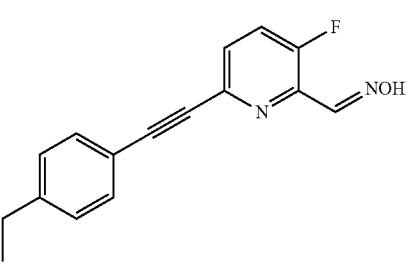

6-(4-chlorobut-1-yn-1-yl)-3-fluoropicolinaldehyde oxime 3i:

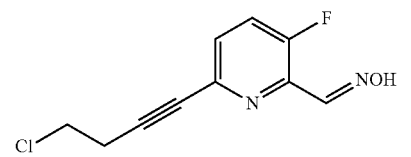

6-((3,6-dihydropyren-4-yl)ethynyl)-3-fluoropicolinaldehyde oxime 3j:

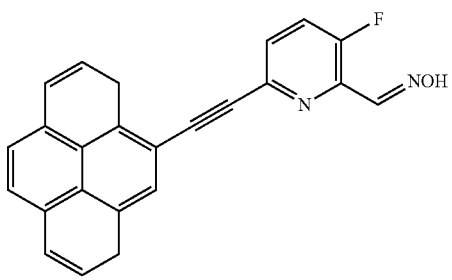

4-(5-fluoro-6-((hydroxyimino)methyl)pyridin-2-yl)but-3-yne-1-sulfonamide 3k:

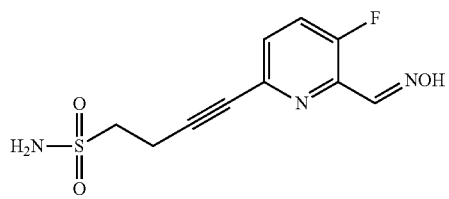

tert-butyl (4-(5-fluoro-6-((hydroxyimino)methyl)pyridin-2-yl)but-3-yn-1-yl)carbam-ate 3l:

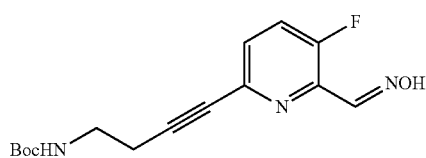

4-((5-fluoro-6-((hydroxyimino)methyl)pyridin-2-yl)ethynyl)benzonitrile 3m:

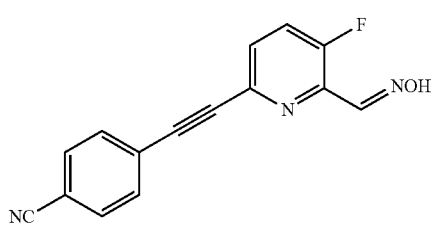

6-(5-(1,3-dioxoisoindolin-2-yl)pent-1-yn-1-yl)-3-fluoropicolinaldehyde oxime 3n:

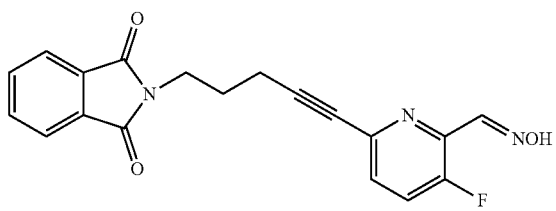

3-fluoro-6-((4-hydroxytetrahydro-2H-pyran-4-yl)ethynyl)picolinaldehyde oxime 3o:

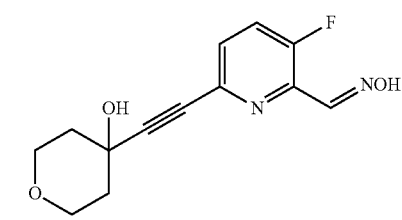

3-fluoro-6-((3-hydroxyoxetan-3-yl)ethynyl)picolinaldehyde oxime 3p:

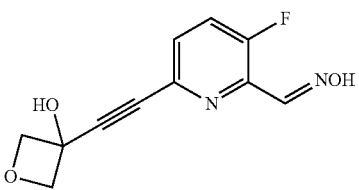

Benzyl 3-((5-fluoro-6-((hydroxyimino)methyl)pyridin-2-yl)ethynyl)azetidine-1-carb-oxylate 3q:

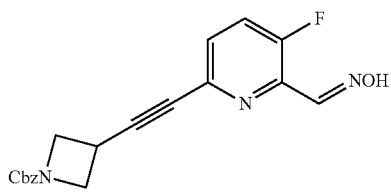

3-fluoro-6-(pyridin-3-ylethynyl)picolinaldehyde oxime 3r:

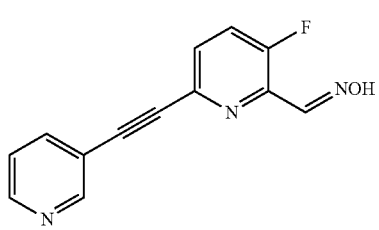

Benzyl (3-(5-fluoro-6-((hydroxyimino)methyl)pyridin-2-yl)prop-2-yn-1-yl)(pyridin-4-yl)carbamate 3s:

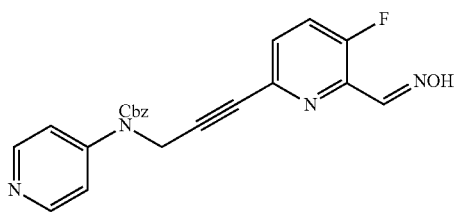

Methyl (S)-2-((tert-butoxycarbonyl)amino)-5-(5-fluoro-6-((hydroxyimino)methyl)pyri-din-2-yl)pent-4-ynoate 3t:

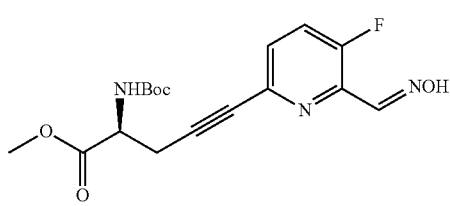

N-(9-((3aR,4R,6R,6aR)-6-(((3-(5-fluoro-6-((hydroxy-imino)methyl)pyridin-2-yl)prop-2-yn-1-yl)oxy)methyl)-2,2-dimethyltetrahydrofuro[3,4-d][1,3]dioxol-4-yl)-9H-purin-6-yl)benzamide 3u:

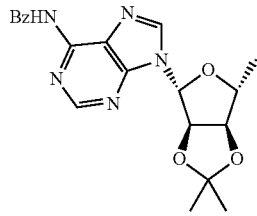

(3aS,4S,6R,6aR)-6-(6-amino-9H-purin-9-yl)-N-(4-(5-fluoro-6-((hydroxyimino)methyl)pyridin-2-yl)but-3-yn-1-yl)-2,2-dimethyltetrahydrofuro[3,4-d][1,3]dioxole-4-carboxamide 3v:

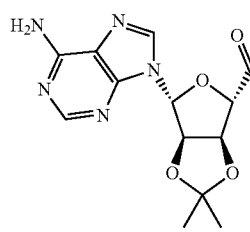

3-fluoro-6-(10-(5-fluoro-6-((E)-(hydroxyimino)methyl)pyridin-2-yl)deca-1,9-diyn-1-yl)picolinaldehyde oxime 3w:

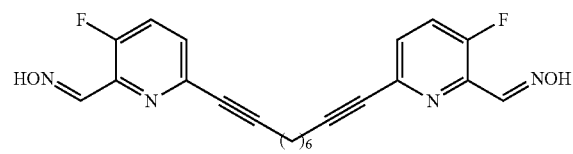

6-(4-((7-chloro-2,3-dihydro-1H-cyclopenta[b]quinolin-9-yl)amino)but-1-yn-1-yl)-3-fluoropicolinaldehyde oxime 3x:

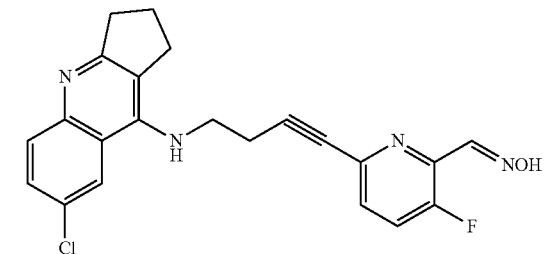

3-fluoro-6-(4-(quinolin-4-ylamino)but-1-yn-1-yl)picolinaldehyde oxime 3y:

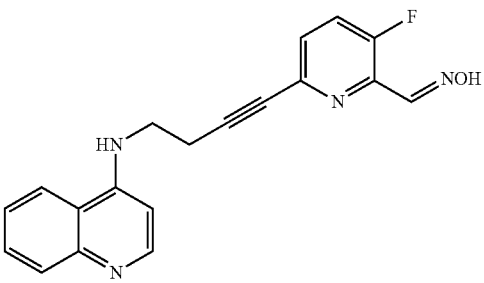

6-(4-(1,2,3,4-tetrahydroacridin-9-ylamino)but-1-yn-1-yl)-3-fluoropicolinaldehyde oxime 3z:

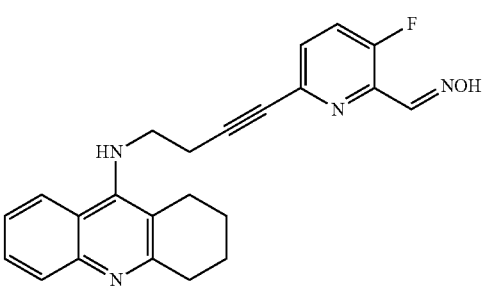

6-bromo-3-fluoropicolinaldehyde oxime (Labelled) 4:

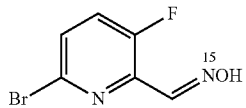

3-fluoro-6-(5-phenylpent-1-yn-1-yl)picolinaldehyde oxime 5:

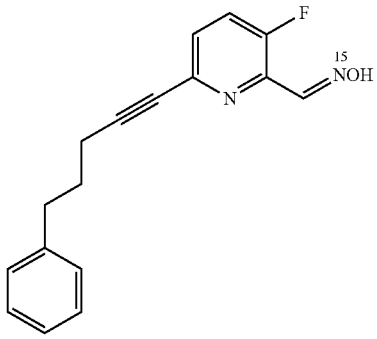

6-bromo-3-fluoro-N'-hydroxypicolinimidamide 7:

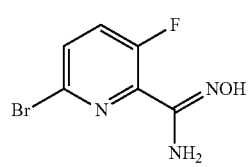

6-bromo-3-fluoro-N'-hydroxypicolinimidamide (Labelled) 8:

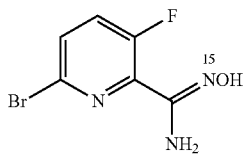

3-fluoro-N'-hydroxy-6-(5-phenylpent-1-yn-1-yl)picolinimidamide 10:

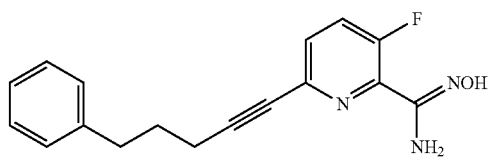

3-fluoro-N-hydroxy-6-(5-phenylpent-1-yn-1-yl)picolinamide 12:

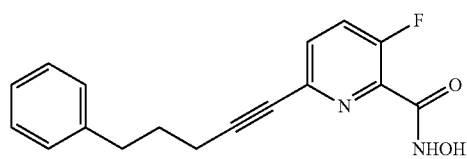

3-fluoro-6-(5-phenylpentyl)picolinaldehyde oxime 13:

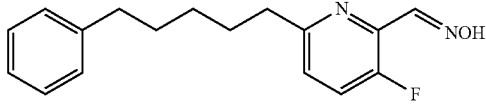

6-(3-cyclohexylpropyl)-3-fluoropicolinaldehyde oxime 14:

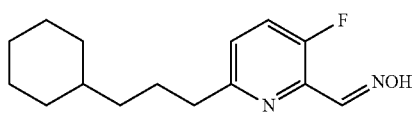

6-(4-ethylphenethyl)-3-fluoropicolinaldehyde oxime 15:

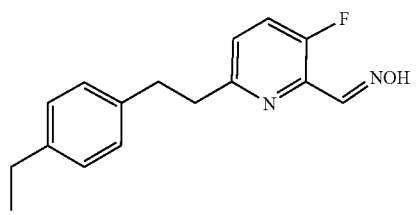

3-fluoro-6-(2-(pyridin-3-yl)ethyl)picolinaldehyde oxime 16:

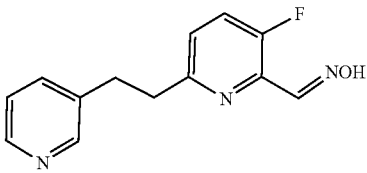

3-fluoro-6-(2-(3-hydroxyoxetan-3-yl)ethyl)picolinaldehyde oxime 17:

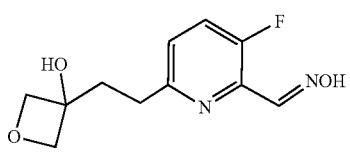

3-fluoro-6-(2-(4-hydroxytetrahydro-2H-pyran-4-yl)ethyl)picolinaldehyde oxime 18:

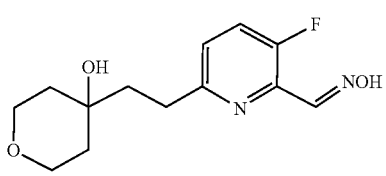

3-fluoro-6-(10-(5-fluoro-6-((E)-(hydroxyimino)methyl)pyridin-2-yl)decyl)picolin-aldehyde oxime 19:

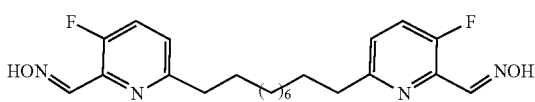

N-(9-((3aR,4R,6R,6aR)-6-((3-(5-fluoro-6-((hydroxyimino)methyl)pyridin-2-yl)propoxy)methyl)-2,2-dimethyltetrahydrofuro[3,4-d][1,3]dioxol-4-yl)-9H-purin-6-yl)benzamide 20:

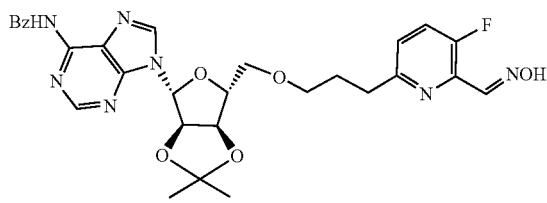

3-fluoro-6-((E)-6-hydroxyhex-1-en-1-yl)picolinaldehyde oxime 21:

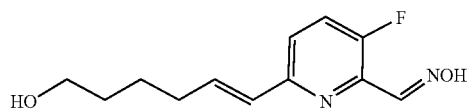

Methyl (E)-6-(5-fluoro-6-((hydroxyimino)methyl)pyridin-2-yl)hex-5-enoate 22:

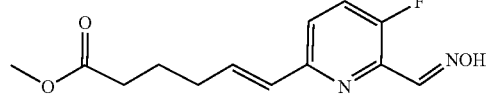

3-fluoro-6-((E)-2-(pyren-4-yl)vinyl)picolinaldehyde oxime 23:

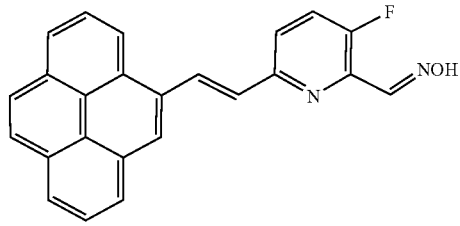

3-fluoro-6-(4-((1,2,3,4-tetrahydroacridin-9-yl)amino)butyl)picolinaldehyde oxime 24:

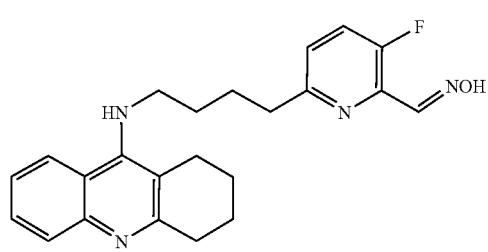

9-((4-(5-fluoro-6-((hydroxyimino)methyl)pyridin-2-yl)butyl)amino)-1,2,3,4-tetrahydroacridin-10-ium chloride 25:

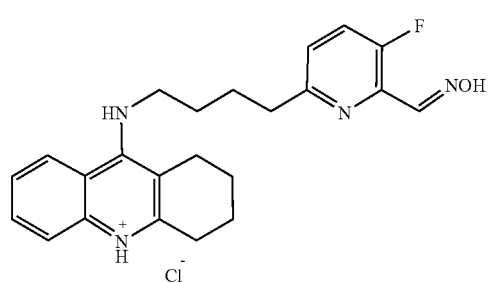

3-fluoro-6-(4-(quinolin-4-ylamino)but-1-yn-1-yl)picolinaldehyde oxime 26:

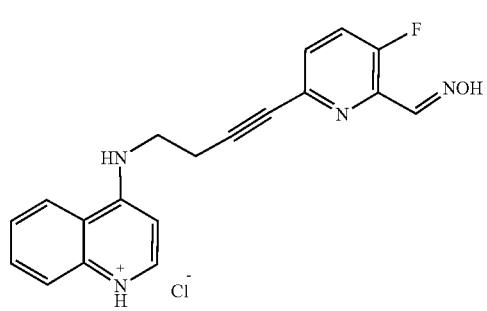

3-fluoro-6-(4-(quinolin-4-ylamino)butyl)picolinaldehyde oxime 27:

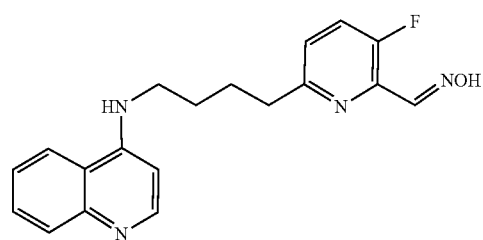

4-((4-(5-fluoro-6-((hydroxyimino)methyl)pyridin-2-yl)butyl)ammonio)quinolin-1-ium chloride 28:

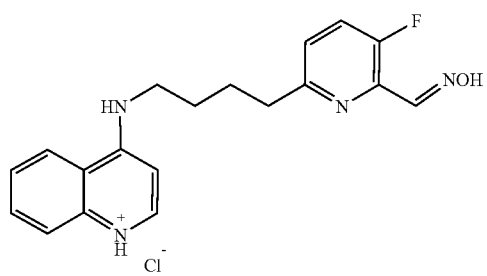

3-((5-fluoro-6-((hydroxyimino)methyl)pyridin-2-yl)ethynyl)pyridin-1-ium chloride 29:

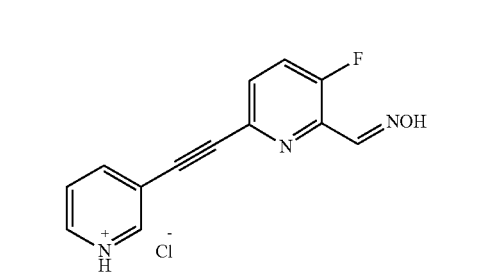

3-(2-(5-fluoro-6-((hydroxyimino)methyl)pyridin-2-yl)ethyl)pyridin-1-ium- chloride 30:

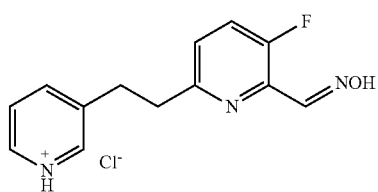

5-bromo-3-fluoropicolinaldehyde oxime 31:

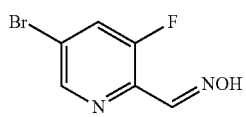

3-fluoro-5-(5-phenylpent-1-yn-1-yl)picolinaldehyde oxime 32:

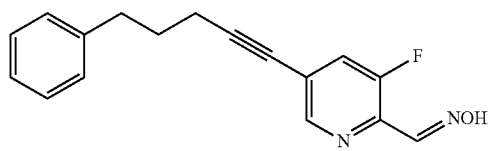

5-bromo-2-fluoronicotinaldehyde oxime 33:

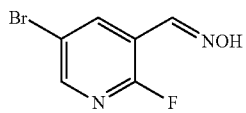

2-fluoro-5-(5-phenylpent-1-yn-1-yl)nicotinaldehyde oxime 34:

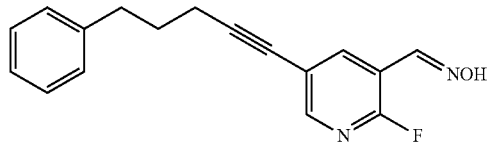

3-bromo-6-chloropicolinaldehyde oxime 35:

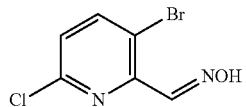

6-chloro-3-(5-phenylpent-1-yn-1-yl)picolinaldehyde oxime 36:

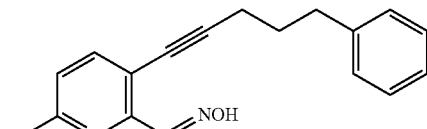

6-bromo-4-chloronicotinaldehyde oxime 37:

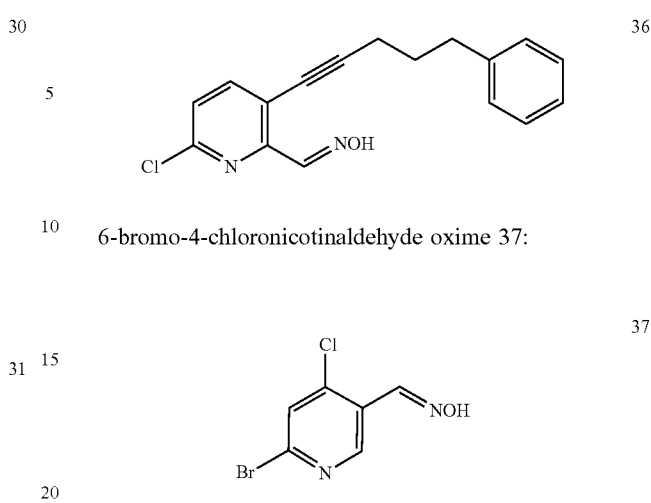

4-chloro-6-(5-phenylpent-1-yn-1-yl)nicotinaldehyde oxime 38:

3-fluoro-N'-hydroxy-6-(pentadec-1-yn-1-yl)picolinimidamide 46:

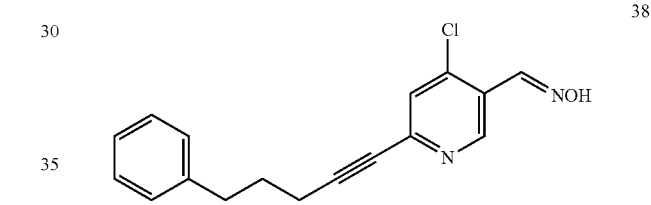

6-((4-ethylphenyl)ethynyl)-3-fluoro-N'-hydroxypicolinimidamide 47:

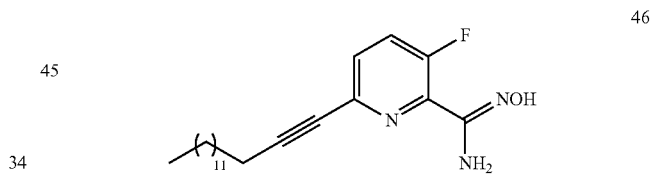

3-fluoro-N'-hydroxy-6-(4-morpholinobut-1-yn-1-yl)picolinimidamide 48:

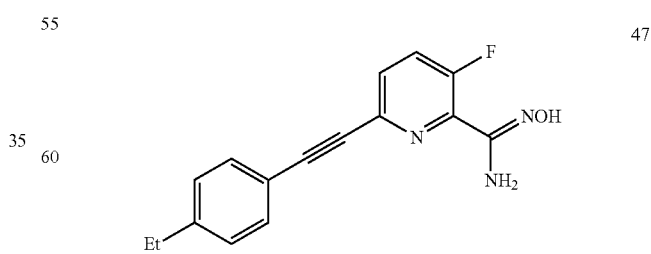

48

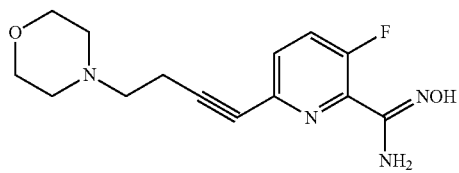

3-fluoro-N'-hydroxy-6-((3-hydroxyoxetan-3-yl)ethynyl) picolinimidamide 49:

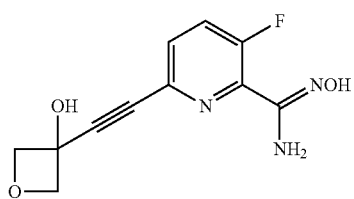

6-((1-aminocyclohexyl)ethynyl)-3-fluoro-N'-hydroxypicolinimidamide 50:

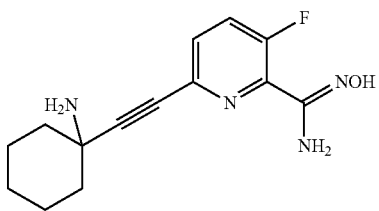

(3aS,4S,6R,6aR)-6-(6-amino-9H-purin-9-yl)-N-(4-(5-fluoro-6-((E)-N'-hydroxycarbam-imidoyl)pyridin-2-yl) but-3-yn-1-yl)-2,2-dimethyltetrahydrofuro[3,4-d][1,3] dioxole-4-carboxamide 51:

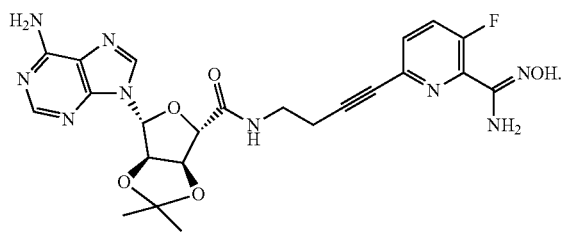

10. A process for preparing a compound of formula (I) of claim 1, comprising a Sonogashira coupling reaction between a 6-bromo-3-fluoro-2-pyridinaldoxime, a 6-bromo-3-fluoro-2-pyridinhydroxamic acid or a 6-bromo-3-fluoro-2-pyridinamidoxime and a compound comprising a terminal alkyne or a dialkyne compound having two terminal alkyne groups.

11. A pharmaceutical composition comprising at least one compound of formula (II) or (I) according to claim 1, and at least one pharmaceutically acceptable support.

12. The compound of claim 1, wherein radical A or radical B may be linked to —Y—X— by an ethyl group, and R6 is a 4-pyridino.

13. The compound of claim 2, wherein radical A or radical B may be linked to —Y—X— by an ethyl group, and R6 is a 4-pyridino.

14. The process of claim 10, further comprising a reduction step by reaction with hydrogen.

* * * * *